(12) United States Patent
Bandi et al.

(10) Patent No.: US 9,868,758 B2
(45) Date of Patent: Jan. 16, 2018

(54) BETULINIC PROLINE IMIDAZOLE DERIVATIVES AS HIV INHIBITORS

(71) Applicant: HETERO LABS LIMITED, Hyderabad (IN)

(72) Inventors: Parthasaradhi Reddy Bandi, Hyderabad (IN); Rathnakar Reddy Kura, Hyderabad (IN); Panduranga Reddy Adulla, Hyderabad (IN); David Krupadanam Gazula Levi, Hyderabad (IN); Eswara Rao Bammidi, Hyderabad (IN); Ranga Reddy, Hyderabad (IN); Carl Thomas Wild, Gaithersburg, MD (US); David Eugene Martin, Shawnee, OK (US); Theodore John Nitz, Boyds, MD (US)

(73) Assignee: HETERO LABS LIMITED, Hyderabad (IN)

( * ) Notice: Subject to any disclaimer, the term of this patent is extended or adjusted under 35 U.S.C. 154(b) by 0 days.

(21) Appl. No.: 15/322,581

(22) PCT Filed: Jun. 29, 2015

(86) PCT No.: PCT/IB2015/054864
§ 371 (c)(1),
(2) Date: Dec. 28, 2016

(87) PCT Pub. No.: WO2016/001820
PCT Pub. Date: Jan. 7, 2016

(65) Prior Publication Data
US 2017/0129917 A1    May 11, 2017

(30) Foreign Application Priority Data
Jun. 30, 2014 (IN) .......................... 3163/CHE/2014

(51) Int. Cl.
*C07J 63/00* (2006.01)

(52) U.S. Cl.
CPC .................................. *C07J 63/008* (2013.01)

(58) Field of Classification Search
None
See application file for complete search history.

(56) References Cited

U.S. PATENT DOCUMENTS

| | | | |
|---|---|---|---|
| 4,598,095 A | 7/1986 | Nishimura et al. | |
| 5,679,828 A | 10/1997 | Lee et al. | |
| 6,451,851 B1 | 9/2002 | Sumegi | |
| 6,670,345 B1 | 10/2003 | Ramadoss et al. | |
| 7,923,573 B2 | 4/2011 | Tamaki et al. | |
| 8,802,727 B2 | 8/2014 | Reddy et al. | |
| 9,067,966 B2 | 6/2015 | Reddy et al. | |
| 9,637,516 B2 | 5/2017 | Parthasaradhi Reddy et al. | |
| 2002/0068757 A1 | 6/2002 | Lin et al. | |
| 2004/0204389 A1 | 10/2004 | Chen et al. | |
| 2006/0205697 A1 | 9/2006 | Robinson et al. | |
| 2008/0207573 A1 | 8/2008 | Yager et al. | |
| 2008/0214516 A1 | 9/2008 | Selzer et al. | |
| 2009/0023698 A1 | 1/2009 | Krasutsky et al. | |
| 2011/0015196 A1 | 1/2011 | Parthasaradhi Reddy et al. | |
| 2011/0152229 A1 | 6/2011 | Chen et al. | |
| 2011/0218204 A1 | 9/2011 | Parthasaradhi Reddy et al. | |
| 2014/0221328 A1 | 8/2014 | Reddy et al. | |
| 2015/0119373 A1 | 4/2015 | Reddy et al. | |
| 2015/0337004 A1 | 11/2015 | Reddy et al. | |
| 2017/0008921 A1 | 1/2017 | Reddy et al. | |
| 2017/0129916 A1 | 5/2017 | Parthasaradhi Reddy et al. | |

FOREIGN PATENT DOCUMENTS

| | | |
|---|---|---|
| CA | 2223513 A1 | 12/1996 |
| CA | 2767642 C | 1/2011 |
| CN | 1861627 A | 11/2006 |
| CN | 10128774 A | 10/2008 |
| EP | 1218402 B1 | 5/2004 |
| WO | 9502071 A1 | 1/1995 |

(Continued)

OTHER PUBLICATIONS

The Organic Chemistry of Drug Design and Drug Action, Silverman, Academic Press, 1992, pp. 352-355, see pp. 354-355.*
Aguado et al., "Enantiodivergent synthesis of cyclobutyl-(Z)-a,β-dehydro-a-amino acid derivatives from (−)-cis-pinononic acid", Tetrahedron: Asymmetry 14, 2003, pp. 217-223.
Aguilera et al., "Stereodivergent synthesis of the first bis(cyciobutane) y-dipeptides and mixed y-oligomers", Tetrahedron: Asymmetry 19, 2008, pp. 302-308.
Antimonova et al., "Synthesis of Betulonic Acid Amindes", Chemistry of Natural Compounds, 2008, vol. 44, No. 3, pp. 327-333.
Dang et al. "Betulinic Acid Derivatives as Human Immunodeficiency Virus Type 2 (HIV-2) Inhibitors" J. Med. Chem., 2009, 52 (23), pp. 7887-7891.

(Continued)

*Primary Examiner* — Karl J Puttlitz
(74) *Attorney, Agent, or Firm* — Cantor Colburn LLP

(57) ABSTRACT

The present invention relates to novel betulinic proline imidazole derivatives and related compounds, compositions useful for therapeutic treatment of viral diseases and particularly HIV mediated diseases.

(1)

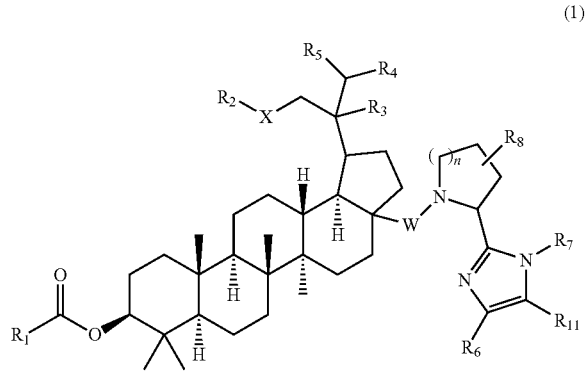

13 Claims, No Drawings

(56) References Cited

FOREIGN PATENT DOCUMENTS

| WO | 9858675 | | 12/1998 |
|---|---|---|---|
| WO | 0046235 | A1 | 8/2000 |
| WO | 0107646 | A2 | 2/2001 |
| WO | 0165957 | A2 | 9/2001 |
| WO | 02091858 | A1 | 11/2002 |
| WO | 03037908 | A1 | 5/2003 |
| WO | 2005090380 | A1 | 9/2005 |
| WO | 2006053255 | A2 | 5/2006 |
| WO | 2006105356 | A2 | 10/2006 |
| WO | 2007002411 | A1 | 1/2007 |
| WO | 2007141383 | A1 | 12/2007 |
| WO | 2007141389 | A1 | 12/2007 |
| WO | 2007141390 | A1 | 12/2007 |
| WO | 2007141391 | A1 | 12/2007 |
| WO | 2007141392 | A2 | 12/2007 |
| WO | 2008057420 | A2 | 5/2008 |
| WO | 2008091532 | A1 | 7/2008 |
| WO | 2008127364 | A2 | 10/2008 |
| WO | 2009082818 | A1 | 7/2009 |
| WO | 2009082819 | A1 | 7/2009 |
| WO | 2009100532 | A1 | 8/2009 |
| WO | 2010132334 | * | 11/2010 |
| WO | 2010132334 | A1 | 11/2010 |
| WO | 2011007230 | A2 | 1/2011 |
| WO | 2011100308 | A1 | 8/2011 |
| WO | 2011153315 | A1 | 12/2011 |
| WO | 2011153319 | A1 | 12/2011 |
| WO | 2012095705 | A1 | 7/2012 |
| WO | 2013020245 | A1 | 2/2013 |
| WO | 2013090664 | A1 | 6/2013 |
| WO | 2013090683 | A1 | 6/2013 |
| WO | 2013117137 | A1 | 8/2013 |
| WO | 2013160810 | A2 | 10/2013 |
| WO | 2014105926 | * | 3/2014 |
| WO | 2014093941 | A1 | 6/2014 |
| WO | 2014105926 | A1 | 7/2014 |
| WO | 2015198263 | A2 | 12/2015 |
| WO | 2016178092 | A2 | 11/2016 |
| WO | 2017017630 | A1 | 2/2017 |

OTHER PUBLICATIONS

Flekhter et al, "Synthesis and Antiinflammatory Activity of New Acylated Betulin Derivatives", Pharmaceutical Chemistry Journal, 2002, vol. 36, No. 9, pp. 488-491.
Greene, T. W. and P. G. M. Wuts, "Protective Groups in Organic Synthesis", 3rd edition, John Wiley & Sons, Inc., New York, 1999.
Hashimoto, F., et al., "Anti-AIDS Agents—XXVIL. Synthesis and Anti-HIV Activity of Betulinic Acid and Dihydrobetulinic Acid Derivatives", Bioorganic & Medicinal Chemistry, 1997, vol. 5, No. 12, pp. 2133-2143.
Jeong H-J et al: "Preparation of amino acid conjugates of betulinic acid with activity against human melanoma", Bioorganic & Medicinal Chemistry Letters, Pergamon, Amsterdam, NL, vol. 9, No. 8, Apr. 19, 1999, pp. 1201-1204.
Moglioni et al.; "Divergent Routes to Chiral Cyclobutane Synthons from (−)-a-Pinene and Their Use in the Steroselective Synthesis of Dehydro Amino Acids", J. Org. Chem. 2000, 65, pp. 3934-3940.
Nair et al., "A Facile and Efficient Synthesis of 3,3-Dimethyl Isopropylidene Proline From (+)-3-Carene", J. Org. Chem 2010, vol. 75, No, 4, pp. 1285-1288.
Pau et al., Antiretroviral Therapy, Infect. Dis. Clin. N. Am., 2014, 28, 371-402.
Qian Keduo et al: "Anti-AIDS agents 81. Design, synthesis, and structure-activity relationship study of betulinic acid and moronic acid derivatives as potent HIV maturation inhibitors.", Journal of Medicinal Chemistry Apr. 22, 2010, vol. 53, No. 8, pages.
Sun, I., et al., "Anti-AIDS Agents, 34. Synthesis and Structure-Activity Relationships of Betulin Derivatives as Anti-HIV Agents", J. Med. Chem. 1998, vol. 41, pp. 4648-4657.

Taiwo et al., "Unmet therapeutic needs in the new era of combination antiretroviral therapy for HIV-1", J. antimicrob Chemother 2010; 65: 1100-1107.
Zhu, YM., et al., "Synthesis and Anti-HIV Activity Oleanolic Acid Derivatives", Bioorganic & Medicinal Chemistry Letters, 2001, vol. 11, pp. 3115-3118.
Averett, D. "Anti-HIV compound assessment by two novel high capacity assays", Journal of Virological Methods, 1989, vol. 23, pp. 263-276.
Balzarini et al., "9-(2phosphonylmethoxyethyl)adenine (PMEA) effectively inhibits retrovirus replication in vitro and simian immunodeficiency virus infection in rhesus monkeys", AIDS, 1991, 5, pp. 21-28.
Barre-Sinoussi et al., "Isolation of a T-Lymphotropic Retrovirus from a Patient at Risk for Acquired Immune Deficiency Syndrome (AIDS)", Science, 1983, vol. 220, pp. 868-871.
Broder et al., "A Pathogenic Retrovirus (HTLV-III) Linked to AIDS", The New England Journal of Medicine, 1984, vol. 311, No. 20, pp. 1292-1297.
Cecilia et al., "Neutralization Profiles of Primary Human Immunodeficiency Virus Type 1 Isolates in the Context of Coreceptor Usage", Journal of Virology, Sep. 1998, vol. 72, No. 9, pp. 6988-6996.
Clark et al., "Synthesis and antiviral activity of 2'-deoxy-2'-fluoro-2'-C-methyl purine nucleosides as inhibitors of hepatitis C virus RNA replication", Bioorganic & Medicinal Chemistry Letters 16 2006, pp. 1712-1715.
Cole, S.P.C., "Rapid chemosensitivity testing of human lung tumor cells using the MTT assay", Cancer Chemotherapy and Pharmacology, 1986, 17, pp. 259-263.
Connor et al., "Characterization of the Functional Properties of env Genes from Long-Term Survivors of Human Immunodeficiency Virus Type 1 Infection", Journal of Virology, 1996, vol. 70, No. 8, pp. 5306-5311.
Daluge et al., "5-Chloro-2',3'-Dideoxy-3'-Fluorouridine (935U83), a Selective Anti-Human Immonudeficiency Virus Agent with an Improved Metabolic and Toxicological Profile", Antimicrobial Agents and Chemotherapy, 1994, vol. 38, No. 7, pp. 1590-1603.
Erice et al., "Anti-Human Immunodeficiency Virus Type 1 Activity of an Anti-CD4 Immunoconjugate Containing Pokeweed Antiviral Protein", Antimicrobial Agents and Chemotherapy, Apr. 1993, vol. 37, No. 4, pp. 835-838.
Fedyuk N. V. et al., Problems of Virology 1992, (3) 135, Abstract Only, 1 page.
Flekhter et al. "Synthesis and Antiinflammatory Activity of New Acylated Betulin Derivatives," Pharmaceutical Chemistry Journal 2002, vol. 36, Issue 9, pp. 29-32.
Fujioka et al. "Anti-AIDS Agents, 11. Betulinic Acid and Platanic Acid as anti-HIV Principles from Syzigium Claviflorum, and the Anti-HIV Activity of Structurally Related Triterpenoids", Journal of Natural Products, 1994, vol. 57, No. 2, pp. 243-247.
Gerrish et al., "Triterpene based compounds with potent antimaturation activity against HIV-1," Bioorganic & Medicinal Chemistry Letters, 2008, vol. 18, Issue 24, pp. 6377-6380.
Harrington et al., "Direct detection of Infectious HIV_1 in blood using a centrifugation-indicator cell assay", Journal of Virological Methods, 2000, vol. 88, pp. 111-115.
International Search Report, International Application No. PCT/IB25015/054864; International Filing Date: Jun. 29, 2015; dated Oct. 16, 2015; 4 Pages.
Kanamoto et al., "Anti-Human Immunodeficiency Virus Activity of YK-FH312 (a Betulinic Acid Derivative), a Novel Compound Blocking Viral Maturation", Antimicrobial Agents and Chemotherapy, 2001, pp. 1225-1230.
Kashiwada et al., "Betulinic Acid and Dihydrobetulinic Acid Derivatives as Potent Anti-HIV Agents", J. Med. Chem. 1996, 39, pp. 1016-1017.
Koyanagi et al., "Selective Cytotoxicity of AIDS Virus Infection Towards HTLV-I-Transformed Cell Lines", Int. J. Cancer, 1985, vol. 36, pp. 445-451.
Li et al.; "PA-457: A Potent HIV Inhibitor that Disrupts Core Condensation by Targeting a Late Step in Gag Processing"; PNAS; 100(23); pp. 13555-13560; (2003).

(56) References Cited

OTHER PUBLICATIONS

Meek et al., "Inhibition of HIV-1 protease in infected T-lymphocytes by synthetic peptide analogues", Nature, 1990, vol. 343, pp, 90-92.
Mimoto et al., "Structure-Activity Relationship of Small-Sized HIV Protease Inhibitors Containing Allophenylnorstatine", J. Med. Chem., 1999, vol. 42, No, 10, pp. 1789-1802.
Mitsuya et al., "Inhibition of the in vitro infectivity and cytopathic effect of human T-lymphotrophic virus type III/lymphadenopathy-associated virus (HTLV-III/LAV) by 2',3'-dideoxynucleosides", Proc. Natl. Acad. Sci. USA, 1986, vol. 83, pp. 1911-1915.
Mosmann, T., Rapid Colorimetric Assay for Cellular Growth and Survival: Application to Proliferation and Cytotoxicity Assays. Journal of Immunological Methods, 65 (1983) 55-63.
Popik et al., "Human Immunodeficiency Virus Type 1 Uses Lipid Raft-Colocalized CD4 and Chemokine Receptors for Productive Entry into CD4+ T Cells", J. of Virology, 2002, pp. 4709-4722.
Qian et al., "Anti-AIDS Agents 90. Novel C-28 Modified Bevirimat Analogues as Potent HIV Maturation Inhibitors," Journal of Medicinal Chemistry, 2012, vol. 55, Issue 18, pp. 8128-8136.
Qian et al., "Anti-AIDS Agents, Synthesis, Metabolic Stability Assessment, and Antiviral Evaluation," Journal of Medicinal Chemistry, 2009, vol. 52, Issue 10, pp. 3248-3258.
Ravi et al, "HIV-1 long terminal repeat promoter regulated dual reporter: Potential use in screening of transcription modulators", Analytical Biochemistry, 2007, vol. 360, pp. 315-317.
Roda Rani et al., "A conserved molecular action of native and recombinant Epap-1 In Inhibition of HIV-1 gp120 mediated viral entry", Archives of Biochemistry and Biophysics, 2006, vol. 456, pp. 79-92.
Roos et al., "LuSIV Cells: A Reporter Cell Line for the Detection and Quantation of a Single Cycle of HIV and SIV Replication", Virology, 2000, vol. 273, pp. 307-315.
Sakalian et al., "3-O-(3',3'-Dimethysuccinyl) Betulinic Acid Inhibits Maturation of the Human Immunodeficiency Virus Type 1 Gag Precursor Assemble In Vitro", J. of Virology, 2006, pp. 5716-5722.
Schwartz et al., "A Rapid Colorimetric Test for the Study of Anti-HIV Agents", AIDS Research and Human Retroviruses, 1988, vol. 4, No. 6, pp. 441-448.
Uckun et al., "TXU (Anti-CD7)-Pokeweed Antiviral Protein as a Potent Inhibitor of Human Immunodeficiency Virus", Antimicrobial Agents and Chemotherapy, Feb. 1998, vol. 42, No. 2, pp. 383-388.
Weislow et al., New Soluble-Formazan Assay for HIV-1 Cytopathic Effects: Application to High-Flux Screening of Synthetic and Natural Products for AIDS—Antiviral Activity, J. Natl. Cancer Inst., 1989, 81, pp. 577-586.
Written Opinion, International Application No. PCT/IB25015/054864; International Filing Date: Jun. 29, 2015; dated Oct. 16, 2015; 5 Pages.
Zhou et al., "Inhibition of HIV-1 Maturation via Drug Association with the Viral Gag Protein in Immature HIV-1 Particles", J. of Bio. Chem., 2005, vol. 280, No. 51, pp. 42149-42155.
Zhou et al., "Small-Molecule Inhibition of Human Immunodeficiency Virus Type 1 Replication by Specific Targeting of the Final Step of Virion Maturation", J. of Virology, 2004, pp. 922-929.

* cited by examiner

BETULINIC PROLINE IMIDAZOLE DERIVATIVES AS HIV INHIBITORS

CROSS-REFERENCE TO RELATED APPLICATIONS

This application is a National Stage application of PCT/IB2015/054864, filed 29 Jun. 2015, which claims the benefit of Indian provisional application no 3163/CHE/2014 filed on 30 Jun. 2014 which are hereby incorporated by reference in their entirety.

FIELD OF THE INVENTION

The present invention relates to novel betulinic proline imidazole derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220, 868-871; N. Eng. J. Med. 1984, 311, 1292-1297). AIDS is characterized by the destruction of the immune system, particularly of CD4+T-cells. HIV is a retrovirus, and the HIV life cycle encompasses several crucial steps, starting from the attachment of the virus to the host cell membrane and finishing with the release of progeny virons from the cell.

The natural compound betulinic acid, isolated from *Syzygium clavifolium* and several other plant species was found to possess anti-HIV activity. Chemical modifications were undertaken by several research groups in an attempt to identify potent anti-HIV agents by making semi-synthetic analogs of betulinic acid, leading to the discovery of bevirimat as a compound with a novel mechanism of action (J. Nat. Prod. 199457(2):243-7; J. Med. Chem. 1996, 39(5), 1016). Further studies shown that bevirimat acts by disrupting Gag processing (Proc. Natl. Acad. Sci. USA 2003, 100(23):13555-60; Antimicrob. Agents. Chemother. 2001, 45(4), 1225-30; J. Virol. 2004, 78(2): 922-9; J. Biol. Chem. 2005, 280(51):42149-55; J. Virol. 2006, 80(12): 5716-22) and to be a first-in-class maturation inhibitor with a potent activity against HIV-1. Bevirimat went up to phase 2 clinical trials, in clinic despite optimal plasma concentrations, not all patients given bevirimat have a robust viral load reduction. It was reported that non-respondent patients had more frequent base line Gag polymorphisms near the capsid SP-1 cleavage site than responders. (HIV gag polymorphism determines treatment response to bevirimat. XVII international HIV drug resistance work shop Jun. 10-14, 2008, Sitges, Spain).

Encouraged by these developments, medicinal chemists started exploring betulinic acid derivatives and related compounds intensively for their therapeutic activities. For example, WO 2014/105926 describes novel betulinic acid proline derivatives as HIV inhibitors; WO 2013/160810 describes novel betulinic acid derivatives as HIV inhibitors; Journal of Medicinal Chemistry (2012), 55(18), 8128-8136 describes Novel C-28 modified bevirimat analogues as potent HIV maturation inhibitors; WO 2011/153319 describes C-28 amides of modified C-3 betulinic acid derivatives as HIV maturation inhibitors; WO 2011/153315 describes modified C-3 betulinic acid derivatives as HIV maturation inhibitors; WO 2011/007230 describes lupeol-type triterpene derivatives as antivirals; WO 2010/132334 describes 3, 28-disubstituted betulinic acid derivatives as anti-HIV agents; Journal of Medicinal Chemistry (2009), 52(10), 3248-3258 describes Design, Synthesis, Metabolic Stability Assessment, and Antiviral Evaluation of Novel Betulinic Acid Derivatives as Potent Anti-Human Immunodeficiency Virus (HIV) Agents; WO 2009/082819 describes novel lupane derivatives; WO 2009/100532 discloses novel 17 β lupine derivatives as anti-HIV agents; Bioorganic & Medicinal Chemistry Letters Volume 18, Issue 24, 15 Dec. 2008, Pages 6377-6380 describes triterpene based compounds with potent anti-maturation activity against HIV-1; The patent publication WO 2008/057420 describes extended triterpene derivatives as antiretroviral agents; WO 2007/141391 describes betulin derived compounds useful as antiprotozoal agents; WO 2007/141390 describes preparation of betulin derived compounds as antiviral agents; WO 2008/127364 describes preparation of betulinic acid derivatives for use in antiviral and anticancer pharmaceutical compositions; US 2008/0207573 describes preparation of triterpene derivatives for therapeutic use in the treatment of viral infections; WO 2007/141389 describes preparation of betulin derived compounds as antibacterial agents; US 2004/0204389 describes anti-HIV agents with dual sites of action; WO 2007/002411 describes antiviral compounds; CN 1861627 describes antitumor agents; WO 2006/053255 describes novel betulin derivatives, preparation and use thereof; WO 2009/082818 describes novel C-21 keto lupine derivatives preparation and use thereof; and WO 2006/105356 describes methods of manufacturing bioactive 3-esters of betulinic aldehyde and betulinic acid.

Some additional references disclose betulinic acid related compounds. For example, WO 2007/141383 describes betulin derivatives as antifeedants for plant pests; U.S. Pat. No. 6,670,345 describes use of betulinic acid and its derivatives for inhibiting cancer growth and process for the manufacture of betulinic acid; WO 2002/091858 describes anxiolytic marcgraviaceae compositions containing betulinic acid, betulinic acid derivatives, and methods of preparation and use; WO 2000/046235 describes preparation of novel betulinic acid derivatives for use as cancer growth inhibitors; WO 2007/141392 describes cosmetic and pharmaceutical compositions comprising betulonic acid and betulin derivatives; and *Pharmaceutical Chemistry Journal*, 2002, 36(9), 29-32 describes synthesis and anti-inflammatory activity of new acylated betulin derivatives.

Given the fact of the world wide epidemic level of AIDS, there is a strong continued need for new effective drugs for treatment of HIV infected patients, disease conditions and/or disorders mediated by HIV by discovering new compounds with novel structures and/or mechanism of action(s).

SUMMARY OF THE INVENTION

The present invention relates to the compounds of the formula (1):

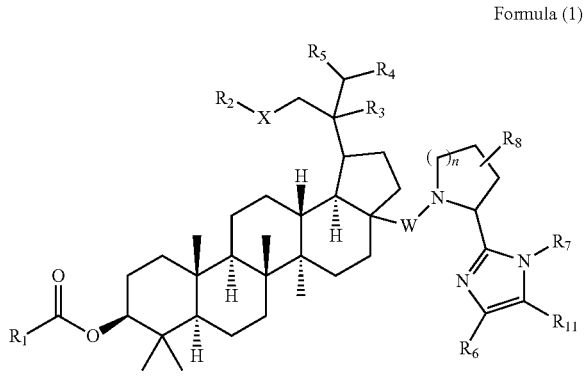

Formula (1)

wherein,

R$_1$ can be substituted or unsubstituted alkyl,

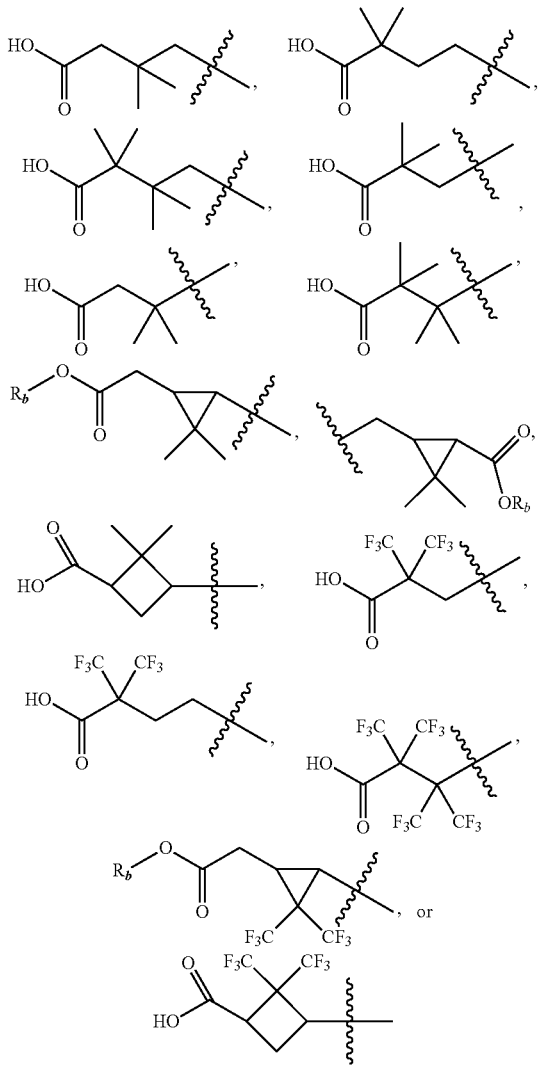

(wherein R$_b$ can be H, substituted or unsubstituted alkyl, or substituted or unsubstituted cycloalkyl);

R$_2$ can be H, substituted or unsubstituted alkyl, substituted or unsubstituted aminoacids, substituted or unsubstituted alkoxy or substituted or unsubstituted cycloalkyl;

X can be absent, O, S, CH$_2$ or NR$_a$ (wherein R$_a$ can be H, substituted or unsubstituted alkyl, substituted or unsubstituted cycloalkyl, or R$_a$ can be with their adjacent N and Carbon together form N-contained heterocycle (Preferably, pyrrolidine, piperdine, piperzine, or morpholine);

R$_3$ and R$_4$ can be independently selected from H, OH, substituted or unsubstituted alkyl, substituted or unsubstituted alkoxy, substituted or unsubstituted alkoxylalkoxy, or substituted or unsubstituted aminoacids and preferably amino acids are substituted by substituted or unsubstituted alkyl, phosphoric acid, or phosphorus prodrugs or R$_3$ and R$_4$ can be together with their adjacent carbons to form a bond or R$_3$ and R$_4$ can be together with their adjacent carbons to form cyclopropyl or R$_3$ and R$_4$ can be together with their adjacent carbons to form epoxide;

W can be C(O), C(S), or CR$_9$R$_{10}$;

R$_6$ can be substituted or unsubstituted alkyl, substituted or unsubstituted cycloalkyl, substituted or unsubstituted aryl, substituted or unsubstituted heterocyclyl, or substituted or unsubstituted heteroaryl and R$_6$ can be preferably substituted or unsubstituted isopropyl, substituted or unsubstituted butyl, substituted or unsubstituted phenyl, substituted or unsubstituted pyridine, substituted or unsubstituted pyrazine, substituted or unsubstituted pyrimidine, or substituted or unsubstituted chromene;

R$_7$ can be independently selected from substituted or unsubstituted alkyl and substituted or unsubstituted alkoxy;

R$_8$ can be independently selected from H, hydroxy, substituted or unsubstituted alkyl, or substituted or unsubstituted alkoxy;

R$_5$, R$_9$ and R$_{10}$ can be independently selected from H, CO$_2$R$_d$ (wherein R$_d$ can be H, substituted or unsubstituted alkyl, or substituted or unsubstituted cycloalkyl), or substituted or unsubstituted alkyl;

R$_{11}$ can be H or substituted or unsubstituted alkyl;

alternatively R$_6$ and R$_{11}$ can be taken together with carbon atoms to which they are attached to form a substituted or unsubstituted aryl;

n can be an integer from 1 to 3.

Pharmaceutically acceptable salts of the compounds of the formula (1) are also contemplated. Likewise, pharmaceutically acceptable solvates, including hydrates, of the compounds of the formula (1) are contemplated.

It should be understood that the formula (1) structurally encompasses all stereoisomers, including enantiomers, diastereomers, racemates, and combinations thereof which may be contemplated from the chemical structure of the genus described herein.

It should be understood that the formula (1) structurally encompasses all tautomers.

Also contemplated are prodrugs of the compounds of the formula (1), including ester prodrugs.

According to one embodiment, there is provided a compound of formula (1), wherein R$_3$ and R$_4$ are together with their adjacent carbons form cyclopropyl.

According to one embodiment, there is provided a compound of formula (1), wherein R$_3$ and R$_4$ are together with their adjacent carbons form a bond.

According to one embodiment, there is provided a compound of formula (1), wherein R$_3$ and R$_4$ is hydrogen.

According to one embodiment, there is provided a compound of formula (1), wherein R$_5$ is H.

According to one embodiment, there is provided a compound of formula (1), wherein R$_2$ is H.

According to one embodiment, there is provided a compound of formula (1), wherein X is absent.

According to one embodiment, there is provided a compound of formula (1), wherein W is C(O).

According to one embodiment, there is provided a compound of formula (1), wherein R$_6$ is substituted or unsubstituted oxadiazole, substituted or unsubstituted oxazole, substituted or unsubstituted imidazole and substituted or unsubstituted triazole. Most specifically the substituents are isopropyl, t-butyl, substituted or unsubstituted phenyl, pyridine, and thiophene.

According to one embodiment, there is provided a compound of formula (1), wherein R$_7$ is substituted or unsubstituted alkyl, substituted or unsubstituted alkoxy, and substituted or unsubstituted amino alkyl;

According to one embodiment, there is provided a compound of formula (1), wherein R$_8$ is independently selected from H, substituted or unsubstituted alkyl, or substituted or unsubstituted alkoxy;

According to one embodiment, there is provided a compound of formula (1), wherein R₁ is

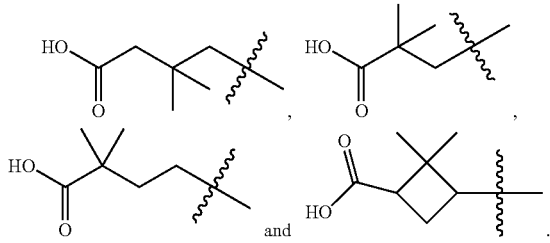

According to one embodiment, there is provided a compound of formula (1), wherein n is 1.

Below are the representative compounds, which are illustrative in nature only and are not intended to limit to the scope of the invention (Nomenclature has been generated from ChemBioDraw Ultra 13.0 version):

(1R,3S)-2,2-dimethyl-3-((((1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid (Compound 1), (1R,3S)-3-((((1R,3aS,5aR,5bR,7aR,9S,11aR,11bR,13aR,13bR)-3a-((S)-2-(1-(2-(2-methoxyethoxy)ethyl)-4-phenyl-1H-imidazol-2-yl)pyrrolidine-1-carbonyl)-5a,5b,8,8,11a-penta methyl-1-(prop-1-en-2-yl)icosahydro-1H-cyclopenta[a]chrysen-9-yl)oxy)carbonyl)-2,2-dimethyl cyclobutane-1-carboxylic acid (Compound 2), (1R,3S)-2,2-dimethyl-3-((((1R,3aS,5aR,5bR,7aR,9S,11aR,11bR,13aR,13bR)-5a,5b,8,8,11a-pentamethyl-3a-((S)-2-(1-(2-morpholinoethyl)-4-phenyl-1H-imidazol-2-yl) pyrrolidine-1-carbonyl)-1-(prop-1-en-2-yl)icosahydro-1H-cyclopenta[a]chrysen-9-yl)oxy) carbonyl)cyclo butane-1-carboxylic acid (Compound 3), (1R,3S)-3-((((1R,3aS,5aR,5bR,7aR,9S,11aR,11bR,13aR,13bR)-3a-((S)-2-(1-(2-methoxyethyl)-4-phenyl-1H-imidazol-2-yl)pyrrolidine-1-carbonyl)-5a,5b,8,8,11a-penta methyl-1-(prop-1-en-2-yl)icosahydro-1H-cyclopenta[a]chrysen-9-yl)oxy)carbonyl)-2,2-dimethylcyclobutane-1-carboxylic acid (Compound 4), (1R,3S)-3-((((1R,3aS,5aR,5bR,7aR,9S,11aR,11bR,13aR,13bR)-3a-((S)-2-(1-(2-(dimethylamino)ethyl)-4-phenyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Compound 5), (1R,3S)-3-((((1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid (Compound 6), (1R,3S)-3-((((1R,3aS,5aR,5bR,7aR,9S,11aR,11bR,13aR,13bR)-3a-((S)-2-(1-(2-(dimethylamino)ethyl)-4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid (Compound 7), (1R,3S)-3-((((1R,3aS,5aR,5bR,7aR,9S,11aR,11bR,13aR,13bR)-3a-((S)-2-(1-(2-(dimethylamino)ethyl)-4-(pyridin-4-yl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid (Compound 8), (1R,3S)-2,2-dimethyl-3-((((1R,3aS,5aR,5bR,7aR,9S,11aR,11bR,13aR,13bR)-5a,5b,8,8,11a-pentamethyl-1-(prop-1-en-2-yl)-3a-((S)-2-(4-(pyridin-4-yl)-1-(2-(pyrrolidin-1-yl) ethyl)-1H-imidazol-2-yl)pyrrolidine-1-carbonyl) icosahydro-1H-cyclopenta[a]chrysen-9-yl)oxy)carbonyl) cyclobutane-1-carboxylic acid (Compound 9), (1R,3S)-2,2-dimethyl-3-((((1R,3aS,5aR,5bR,7aR,9S,11aR,11bR,13aR,13bR)-5a,5b,8,8,11a-pentamethyl-3a-((S)-2-(4-phenyl-1-(2-(pyrrolidin-1-yl)ethyl)-1H-imidazol-2-yl) pyrrolidine-1-carbonyl)-1-(prop-1-en-2-yl)icosahydro-1H-cyclopenta[a]chrysen-9-yl)oxy) carbonyl)cyclo butane-1-carboxylic acid (Compound 10), (1R,3S)-3-((((1R,3aS,5aR,5bR,7aR,9S,11aR,11bR,13aR,13bR)-3a-((S)-2-(4-(tert-butyl)-1-(2-(dimethylamino)ethyl)-1H-imidazol-2-yl)pyrrolidine-1-carbonyl)-5a,5b,8,8,11a-penta methyl-1-(prop-1-en-2-yl)icosahydro-1H-cyclopenta[a]chrysen-9-yl)oxy)carbonyl)-2,2-dimethyl cyclobutane-1-carboxylic acid (Compound 11), (1R,3S)-3-((((1R,3aS,5aR,5bR,7aR,9S,11aR,11bR,13aR,13bR)-3a-((S)-2-(1-(2-(dimethylamino)ethyl)-4-(3-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid (Compound 12), (1R,3S)-3-((((1R,3aS,5aR,5bR,7aR,9S,11aR,11bR,13aR,13bR)-3a-((S)-2-(1-(2-(dimethylamino)ethyl)-4-isopropyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Compound 13), (1R,3S)-3-((((1R,3aS,5aR,5bR,7aR,9S,11aR,11bR,13aR,13bR)-3a-((S)-2-(1-(2-(dimethylamino)ethyl)-4,5-dimethyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid (Compound 14), 2,2-dimethyl-4-oxo-4-(((1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl)oxy)butanoic acid (Compound 15), 4-(((1R,3aS,5aR,5bR,7aR,9S,11aR,11bR,13aR,13bR)-3a-((S)-2-(1-(2-(dimethyl amino)ethyl)-4-phenyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxo butanoic acid (Compound 16), 4-(((1R,3aS,5aR,5bR,7aR,9S,11aR,11bR,13aR,13bR)-3a-((S)-2-(1-(2-methoxyethyl)-4-phenyl-1H-imidazol-2-yl) pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid (Compound 17), 4-(((1R,3aS,5aR,5bR,7aR,9S,11aR,11bR,13aR,13bR)-3a-((S)-2-(1-(2-(dimethyl amino)ethyl)-4-(pyridin-3-yl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid (Compound 18), (1R,3S)-3-((((1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid (Compound 19), (1R,3S)-3-((((1R,3aS,5aR,5bR,7aR,9S,11aR,11bR,13aR, 13bR)-3a-((S)-2-(4-(tert-butyl)-1-(2-(dimethylamino) ethyl)-1H-imidazol-2-yl)pyrrolidine-1-carbonyl)-5a,5b,8, 8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid (Compound 20), (1R,3S)-3-((((1R,3aS,5aR,5bR,7aR,9S,11aR,11bR,13aR, 13bR)-3a-((S)-2-(1-(2-(dimethylamino)ethyl)-4,5-dimethyl-1H-imidazol-2-yl)pyrrolidine-1-carbonyl)-5a,5b,8, 8,11a-pentamethyl-1-(1-methylcyclopropyl)icosahydro-1H-cyclopenta[a]chrysen-9-yl)oxy) carbonyl)-2,2-dimethyl cyclobutane-1-carboxylic acid (Compound 21), (1R,3S)-3-((((1R,3aS,5aR,5bR,7aR,9S,11aR,11bR,13aR, 13bR)-3a-((S)-2-(1-(2-(diethoxyphosphoryl)ethyl)-4-phenyl-1H-imidazol-2-yl)pyrrolidine-1-carbonyl)-5a,5b, 8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid (Compound 22), (1R,3S)-2,2-dimethyl-3-((((1R,3aS,5aR,5bR,7aR,9S,11aR, 11bR,13aR,13bR)-5a,5b,8,8,11a-pentamethyl-3a-((S)-2-(4-phenyl-1-(2-phosphonoethyl)-1H-imidazol-2-yl) pyrrolidine-1-carbonyl)-1-(prop-1-en-2-yl)icosahydro-1H-cyclopenta[a]chrysen-9-yl)oxy) carbonyl)cyclo butane-1-carboxylic acid (Compound 23), (1R,3S)-3-((((1R,3aS,5aR,5bR,7aR,9S,11aR,11bR,13aR, 13bR)-3a-((S)-2-(1-(2-(diethoxyphosphoryl)ethyl)-4-(4-fluorophenyl)-1H-imidazol-2-yl)pyrrolidine-1-carbonyl)-5a,5b,8,8,11a-pentamethyl-1-(prop-1-en-2-yl) icosahydro-1H-cyclopenta[a]chrysen-9-yl)oxy) carbonyl)-2,2-dimethylcyclobutane-1-carboxylic acid (Compound 24), (1R,3S)-3-((((1R,3aS,5aR,5bR,7aR,9S,11aR,11bR,13aR, 13bR)-3a-((2S,4R)-2-(1-(2-(dimethylamino)ethyl)-4-phenyl-1H-imidazol-2-yl)-4-(2-methoxyethoxy)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethylcyclobutane-1-carboxylic acid (Compound 25), (1R,3S)-3-((((1R,3aS,5aR,5bR,7aR,9S,11aR,11bR,13aR, 13bR)-3a-((2S,4R)-2-(1-isopentyl-4-phenyl-1H-imidazol-2-yl)-4-(2-methoxyethoxy)pyrrolidine-1-carbonyl)-5a,5b,8,8,11a-pentamethyl-1-(prop-1-en-2-yl) icosahydro-1H-cyclopenta[a]chrysen-9-yl)oxy) carbonyl)-2,2-dimethylcyclobutane-1-carboxylic acid (Compound 26), (1R,3S)-3-((((1R,3aS,5aR,5bR,7aR,9S,11aR,11bR,13aR, 13bR)-3a-((2S,4R)-4-(2-methoxyethoxy)-2-(4-phenyl-1-(2-(pyrrolidin-1-yl)ethyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethylcyclobutane-1-carboxylic acid (Compound 27), (1R,3S)-3-((((1R,3aS,5aR,5bR,7aR,9S,11aR,11bR,13aR, 13bR)-3a-((2S,4R)-2-(4-(3-fluorophenyl)-1-(2-(pyrrolidin-1-yl)ethyl)-1H-imidazol-2-yl)-4-(2-methoxyethoxy) pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Compound 28), (1R,3S)-3-((((1R,3aS,5aR,5bR,7aR,9S,11aR,11bR,13aR, 13bR)-3a-((S)-2-(1-(2-(dimethylamino)ethyl)-1H-benzo [d]imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Compound 29), (1R,3S)-2,2-dimethyl-3-((((1R,3aS,5aR,5bR,7aR,9S,11aR, 11bR,13aR,13bR)-5a,5b,8,8,11a-pentamethyl-1-(prop-1-en-2-yl)-3a-((S)-2-(1-(2-(pyrrolidin-1-yl)ethyl)-1H-benzo[d]imidazol-2-yl)pyrrolidine-1-carbonyl) icosahydro-1H-cyclopenta[a]chrysen-9-yl)oxy) carbonyl) cyclobutane-1-carboxylic acid (Compound 30), or pharmaceutically acceptable salts, solvates, including hydrates and prodrugs of compounds are also contemplated.

The present invention also provides a pharmaceutical composition that includes at least one compound of described herein and at least one pharmaceutically acceptable excipient (such as a pharmaceutically acceptable carrier or diluent). Preferably, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in a therapeutically effective amount to cause that infection Also provided herein are processes for preparing compounds described herein.

The invention provides a method for preventing; ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as persistent generalized lymphadenopathy, fever and weight loss, or an etroviral infection genetically related to AIDS.

Anti HIV inhibitory potential of the compounds of present invention may be demonstrated by any one or more methodologies known in the art, such as by using the assays described in Mosmann T, December 1983, *Journal of immunological methods*, 65 (1-2), 55-63 and S P C Cole, *cancer chemotherapy and Pharmacology*, 1986, 17, 259-263.

DETAILED DESCRIPTION OF THE INVENTION

The present invention provides betulinic acid proline imidazole derivatives and related compounds, which may be used as antiviral particularly as anti-HIV compounds and processes for the synthesis of these compounds. Pharmaceutically acceptable salts, pharmaceutically acceptable solvates, enantiomers, diastereomers of the derivatives, together with pharmaceutically acceptable carriers, excipients or diluents, which can be used for the treatment of diseases, condition and/or disorders mediated by viral infections, are also provided.

The Following Definitions Apply to the Terms as Used Herein

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkoxy" refers to a straight or branched hydrocarbon chain with oxygen radical consisting carbon and hydrogen atoms, containing saturation or unsaturation, having from one to eight carbon atoms, and which is attached through oxygen atom to the rest of the molecule by a single bond, e.g., methyloxy, ethyloxy, n-propyloxy, 1-methylethyloxy (isopropyloxy), n-butyloxy, n-pentyloxy, and 1,1-dimethylethyloxy (t-butyloxy).

The term "alkoxylalkoxy" refers to a straight or branched hydrocarbon chain with oxygen radical consisting carbon atom, hydrogen atom and alkoxy groups, containing saturation or unsaturation, having from one to eight carbon atoms, and which is attached through oxygen atom to the rest of the molecule by a single bond, e.g., 2-(methyloxy) ethyloxy, 2-(ethyloxy)ethyloxy, 2-(n-propyloxy)ethyloxy, and 3-(isopropyloxy)butyloxy.

The term "amino acid" refers to a straight or branched hydrocarbon chain containing an amine group, a carboxylic acid group, and a side-chain that is specific to each amino acid and which is attached through the nitrogen atom of the amine group to the rest of the molecule by a single bond, e.g., alanine, valine, isoleucine, leucine, phenylalanine, or tyrosine.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronaphthyl, adamantyl and norbornyl groups, bridged cyclic groups and spirobicyclic groups, e.g., spiro (4,4) non-2-yl.

The term "aryl" refers to an aromatic radical having from 6 to 14 carbon atoms such as phenyl, naphthyl, tetrahydronaphthyl, indanyl, and biphenyl.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, tetrazoyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl. The heterocyclic ring radical may be attached to the main structure at any heteroatom or carbon atom that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

"Substituted" refers to 1-3 substituents on the same position or on different positions with the same groups or different groups. Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —COOR$'''$, —C(O)R$^x$, —C(S)R$'''$, —C(O)NR$'''$R$^y$, —C(O)ONR$'''$R$^y$, —NR$'''$CONR$^y$R$^z$, —N(R$'''$)SOR$^y$, —N(R$'''$)SO$_2$R$^y$, —(=N—N(R$'''$)R$^y$), —NR$'''$C(O)OR$^y$, —NR$'''$R$^y$, —NR$'''$C(O)R$^y$, —NR$'''$(S)R$^y$, —NR$'''$(S)NR$^y$R$^z$, —SONR$'''$R$^y$, —SO$_2$NR$'''$R$^y$, —OR$'''$, —OR$'''$C(O)NR$^y$R$^z$, —OR$'''$C(O)OR$^y$, —OC(O)R$'''$, —OC(O)NR$'''$R$^y$, —P(O)(OR$'''$)$_2$, —R$'''$NR$^y$C(O)R$^z$, —R$'''$OR$^y$, —R$'''$C(O)OR$^y$, —R$'''$C(O)NR$^y$R$^z$, —R$'''$C(O)R$^y$, —R$'''$OC(O)R$^y$, SR$'''$, SOR$'''$, —SO$_2$R$'''$, and —ONO$_2$, wherein R$'''$, R$^y$ and R$^z$ are independently selected from hydrogen, substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "prodrug" means a compound that is transformed in vivo to yield a compound of Formula (1), or a pharmaceutically acceptable salt, hydrate or solvate, or metabolite of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:
  (1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;
  (2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

Pharmaceutically acceptable solvates includes hydrates and other solvents of crystallization (such as alcohols). The compounds of the present invention may form solvates with low molecular weight solvents by methods known in the art.

Pharmaceutical Compositions

The pharmaceutical compositions provided in the present invention include at least one compound described herein and at least one pharmaceutically acceptable excipient (such as a pharmaceutically acceptable carrier or diluent). Preferably, the contemplated pharmaceutical compositions include a compound(s) described herein in an amount sufficient to treat viral infection in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared, e.g., as described in Remington: *The Science and Practice of Pharmacy*, 20th Ed., 2003 (Lippincott Williams & Wilkins). For example, the active compound can be mixed with a carrier, or diluted by a carrier, or enclosed within a carrier, which may be in the form of an ampule, capsule, or sachet. When the carrier serves as a diluent, it may be a solid, semisolid, or liquid material that acts as a vehicle, excipient, or medium for the active compound.

The pharmaceutical compositions may be, for example, capsules, tablets, aerosols, solutions, suspensions, liquids, gels, or products for topical application.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Screening

Antiviral HIV activity and cytotoxicity of compounds present invention can be measured in parallel by following the methods published in the literature.

The cytotoxic effect of compounds can be analyzed by measuring the proliferation of cells using the 3-(4,5-Dimethylthiazol-2-yl)-2,5-diphenyl tetrazolium bromide (MTT) staining. Cells ($5 \times 10^3$ cells/well) will be incubated in 96 well plates in the presence or absence of compounds. At the end of treatment, 20 µl of MTT (5 mg/ml in PBS) will be added to each well and incubated for an additional 4 hours at 37° C. The purple-blue MTT formazan precipitate will be dissolved in a triplex reagent containing 10% SDS, 5% isobutanol and 10 mmol/lit HCl. The activity of mitochondria, reflecting cellular growth and viability, will be evaluated by measuring the optical density at 570 nm on micro titer plate.

Action of compounds on replication of HIV in Sup-T1 cells can be determined by the method published by Roda Rani et al., 2006 (Archives of Biochemistry and Biophysics, Volume 456, Issue 1, 1 Dec. 2006, Pages 79-92).

Briefly, $1 \times 10^6$ Sup-T1 cells with 100% cell viability will be seeded in RPMI 1640, 0.1% FBS four 12 well plates. Increasing concentrations of Epap-1 peptides will be added to the cells and will be infected with HIV $1_{93\ IN\ 101}$ each at final concentration of virus equivalent to 2 ng of p24 per ml. The infected cells will be incubated at 37 C and 5% CO2 incubator for 2 hours. After 2 hrs the cells will be pelleted at 350 g for 10 min, supernatant will be discarded and cell will be held with RPMI 1640 containing 10% FBS. The cells will be resuspended in the same medium with increasing concentrations of Epap-1 peptides and will be incubated for 96 hours. The cells will be supplemented with peptides at every 24 hours. The supernatants will be collected after 96 hours and analyzed using P24 antigen capture assay kit (SAIC Fredrick). The infection in the absence of Epap-1 will be considered to be 0% inhibition Azidothymidine (AZT) will be taken as positive control.

Action of compound on virus entry and quantification of virus entered can be done in terms of GFP expression by the following the methods published J. Virol. 72, 6988 (1998) by in Cecilia et al., and Analytical Biochemistry Volume 360, Issue 2, 15 Jan. 2007, Pages 315-317 (Dyavar S. Ravi and Debashis Mitra).

Briefly, cells will be seeded in to wells of 24 well plates 1 day prior to the experiment. The cells will be transfected with Tat-reporter. The virus inoculum will be adjusted to 1,000-4,000 TCID 50/ml in assay medium (DMEM, 10% FCS, glutamine and antibiotics), 50 µl aliquots will be incubated with serial dilutions of compounds (50 µl) for 1 hr at 37° C. The reporter expression will be quantified at appropriate time calculated inhibitory doses referrers to the concentration of these agents in this preincubation mixture.

Other relevant references useful for screening antiviral HIV activity are: Averett, D. R. 1989. Anti-HIV compound assessment by two novel high capacity assays. J. Virol. Methods 23: 263-276; Schwartz, O., et al. 1998; A rapid and simple colorimetric test for the study of anti HIV agents. AIDS Res. and Human Retroviruses, 4(6):441-447; Daluge, S. M., et al. 1994. 5-Chloro-2',3'-deoxy-3'fluorouridine (935U83), a selective anti human immunodeficiency virus agent with an improved metabolic and toxicological profile; Antimicro. Agents and Chemotherapy, 38(7): 1590-1603; H. Mitsuya and S. Border, Inhibition of the in vitro infectivity and cytopathic effect of human T-lympho tropic virus type lymphadenopathy-associated virus (HLTV-III/LAV) by 2,3'-dideoxynucleosides, Proc. Natl. Acad. Sci. USA, 83, 1911-15 (1986); Pennington et al., Peptides 1990; Meek T. D et al., Inhibition of HIV-1 protease in infected T-lymphocytes by synthetic peptide analogues, Nature, 343, p 90 (1990); Weislow et al., J. Natl. Cancer Inst. 81, 577-586, 1989; T. Mimoto et al., J. Med. Chem., 42, 1789-1802, 1999; Uckun et al 1998, Antimicrobial Agents and Chemotherapy 42:383; for P24 antigen assay Erice et al., 1993, Antimicrob. Ag. Chemotherapy 37: 835-838; Koyanagi et al., Int. J. Cancer, 36, 445-451, 1985; Balzarini et al. AIDS (1991), 5, 21-28; Connor et al., Journal of virology, 1996, 70, 5306-5311; Popik et al., Journal of virology, 2002, 76, 4709-4722; Harrigton et al., Journal of Virology Methods, 2000, 88, 111-115; Roos et al., Virology 2000, 273, 307-315; Fedyuk N. V. et al; Problems of Virology 1992, (3)P135; Mosmann T, December 1983, Journal of immunological methods, 65 (1-2), 55-63; S P C Cole, cancer chemotherapy and Pharmacology, 1986, 17, 259-263.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01/07646, WO 01/65957, or WO 03/037908; US publication Nos. U.S. Pat. No. 4,598,095 or US 2002/0068757; EP publication Nos. EP 0989862 or EP 0724650; *Bioorganic & Medicinal Chemistry Letters,* 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV, HCV, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

Methods of Preparation

The compounds described herein may be prepared by techniques known in the art. In addition, the compounds described herein may be prepared by following the reaction sequence as depicted in Scheme-1 to 2. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereoisomers of the compounds in these schemes, unless otherwise specified, are also encompassed within the scope of this invention.

Compounds of the present invention can be synthesized from naturally occurring Betulinic acid or betulinal. Key intermediates required for synthesizing analogues are either commercially available, or can be prepared by the methods published in the literature.

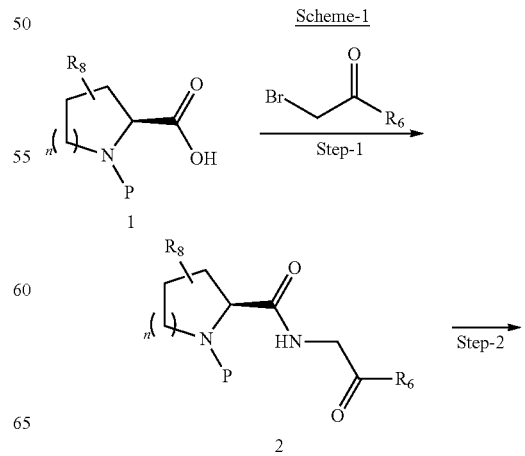

Scheme-1

-continued

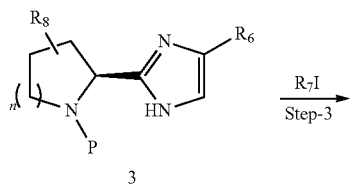

3

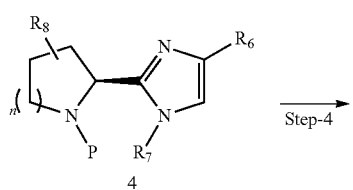

4

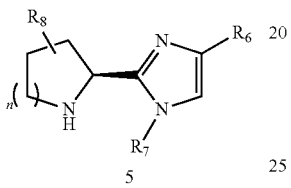

5

-continued

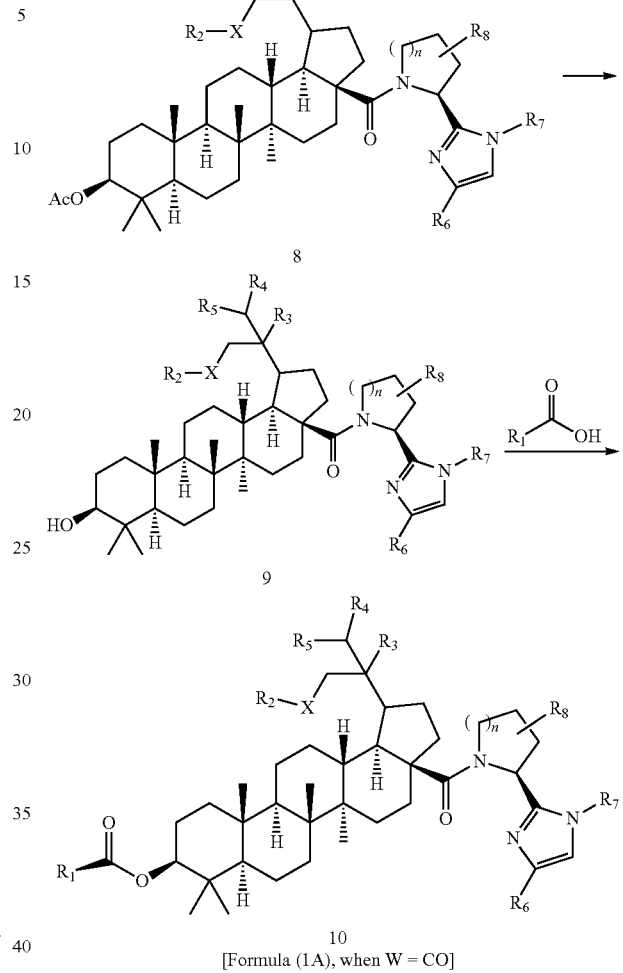

Compounds of formula 5 (n and R$_6$ are same as defined above, R$_6$ is more specifically isopropyl, t-butyl, substituted or unsubstituted phenyl, pyridine, and thiophene) and P can be a protecting group more specifically BOC, benzyl, MOM chloride (chloromethyl methyl ether), tosyl, TBDMS, p-methoxy phenyl (PMP), CBZ chloride, THP, dimethyl acetol, allyl ether, t-butyl ether or phthalimide can be prepared as described in Scheme 1. The substituted proline compounds of formula 1 can be converted to substituted ether compounds of formula 2 in the presence of substituted 2-bromo-1-phenylethanone and DIPEA, or the like in the solvents such as DCM, or the like. The ether compounds of formula 2 can be cyclized in presence of ammonium acetate and toluene or the like to get compounds of formula 3. Compounds of formula 3 in the presence of suitable coupling agents such substituted halides, NaH, or the like in the solvents such as DMF or the like to get compounds of formula 4. Compounds of formula 4 can be deprotected to give NH proline compounds of formula 5 in the presence of TFA, HCl or the like in the solvents such as DCM, ethyl acetate or the like.

Compounds of formula 10 [Formula (1A), when W═CO] (R$_1$, R$_2$, R$_3$, R$_4$, R$_5$, R$_6$, R$_x$, and n are same as defined above & R$_x$ is more specifically substituted or unsubstituted oxadiazole or imidazole or oxazole or triazole and the substituents are more specifically isopropyl, t-butyl, substituted or unsubstituted phenyl, pyridine, and thiophene) can be prepared as described in Scheme 2. Reacting a C-3 alcohol with a suitable ester forming reagents like anhydrides, acid halides or mixed anhydrides in the presence of a base like triethyl amine, diisopropyl ethyl mine, or pyridine in an inert solvent like DCM, toluene, THF or a basic solvent like pyridine with or without addition of a catalyst like DMAP. For example the C-3 acetyl (C-28 acid) compounds of formula 6 can be couple with substituted proline compounds of formula 7 (synthesized as described in Scheme 1) to give the C-28 cyclic amide compounds of formula 8 in the presence of oxylylchloride, TEA or the like in the presence of solvents such as DCM, or the like. The C-28 cyclic amide (C-3 ester) compounds of formula 8 can be hydrolysed to give C-3 hydroxy compounds of formula 9 in the presence of bases such as potassium carbonate, sodium hydroxide, ammonia or the like in the solvents such as methanol:THF, methanol:water, 1,4-dioxane, methanol or the like. The C-3 hydroxy compounds of formula 9 can be reacted with corresponding acid anhydrides, half protected diacids or their mixed anhydrides or acid chlorides to give the corresponding compounds of present invention represented by formula 10 [Formula (1), when W=CO] in the presence a base like triethyl amine, 4-Dimethylaminopyridine, diisopropyl ethyl mine or pyridine or the like in the solvents such as for example, DCM, toluene, EtOAc, THF or the like.

The abbreviations used in the entire specification may be summarized hereinbelow with their particular meaning TBDMS (tert-Butyldimethylsilyl chloride); CB z (Benzyloxy carbamoyl chloride); THP (Tetrahydropyran); DIPEA (N,N-Diisopropylethylamine); ° C. (degree Celsius); δ (delta); % (percentage); DMSO-d$_6$ (Deuteriated DMSO); d (Doublet); dd (Doublet of doublet); dt (Doublet of triplet); EtOH (Ethanol); Et$_2$O (Diethyl ether); EtOAc (Ethyl acetate); g or gr (gram); H or H$_2$ (Hydrogen); HCl (Hydrochloric acid); h or hr (Hours); HATU (2-(1H-7-Azabenzotriazol-1-yl)-1, 1,3,3-tetramethyl uranium hexafluoro phosphate methanaminium); Hz (Hertz); HPLC (High-performance liquid chromatography); LiOH.H$_2$O (Lithium hydroxide mono hydrate); MeOH/CH$_3$OH (Methanol); MP (Melting point); mmol (Millimol); M (Molar); μl (Micro liter); ml (Milliliter); mg (Milli gram); m (Multiplet); mm (Millimeter); MHz (Megahertz); MS (ES) (Mass spectroscopy-electro spray); min (Minutes); mM (milli molar); NaOH (Sodium hydroxide); N$_2$ (Nitrogen); NMR (Nuclear magnetic resonance spectroscopy); NH$_2$OH.HCl (Hydroxylamine hydrochloride; 10% Pd/C (10% palladium activated carbon); S (Singlet); bs: broad singlet; TEA (Triethyl amine); TFA (Trifluoroacetic acid); TLC (Thin Layer Chromatography); THF (Tetrahydrofuran); tert (Tertiary), TFA/CF$_3$COOH (Trifluoro acetic acid); t (Triplet); MHz (Mega Hertz); IC (Inhibitory concentration), nM (Nano molar); pH (Pouvoir hydrogen); BOC (Di-tert-butyl dicarbonate); tosyl (Para toluene sulfonyl chloride); DCM (dichloro methane); DMF (N, N dimethyl formamide); DMAP (N, N dimethyl amino pyridine).

Experimental

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and examples may be further implemented as disclosed by variously altering the following examples, substituents, reagents, or conditions.

Intermediates

Intermediate 1: Preparation of (S)-1-methyl-4-phenyl-2-(pyrrolidin-2-yl)-1H-imidazole

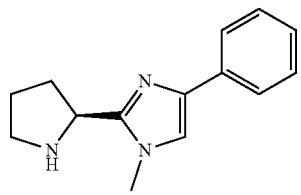 [SMILES: Cn1cc(-c2ccccc2)nc1[C@@H]1CCCN1]

Preparation of Boc-L-Proline:

To a solution of L-proline (10.0 g, 86.85 mmol) in a 1:2 mixture of 1,4-dioxane (50 ml) and H$_2$O (100 ml) was added NaHCO$_3$ (18.24 g, 217.0 mmol). After stirring about 30 minutes at room temperature, the reaction mixture was treated with di-tert-butyldicarbonate (20.85 g, 95.54 mmol). The resulting solution was stirred for overnight (about 18 hours) at room temperature and the solution pH was adjusted 2 to 3 by addition of 4N hydrochloric acid (Note: the temperature of reaction mixture should be 5-10° C.). The aqueous layer was extracted with dichloromethane (2×100 ml), the combined organic layers were washed with water, dried over Na$_2$SO$_4$, filtered and solvent was evaporated under reduced pressure to provide Boc-L-proline as a white solid (17.0 g, yield: 91%).

Step 1: Synthesis of (S)-1-tert-butyl 2-(2-oxo-2-phenylethyl)pyrrolidine-1,2-dicarboxylate

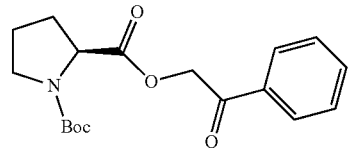 [SMILES: CC(C)(C)OC(=O)N1CCC[C@H]1C(=O)OCC(=O)c1ccccc1]

To a stirred solution of (S)-1-(tert-butoxycarbonyl)pyrrolidine-2-carboxylic acid (10.0 g, 46.45 mmol) in DCM (100 ml) was added DIPEA (16.07 ml, 92.91 mmol) at 0° C. and after 10 minutes 2-bromo-1-phenylethanone (9.24 g, 46.45 mmol) was added and the reaction mixture was allowed to stir at room temperature for about 12 hours. After completion of the reaction (monitored by TLC), the reaction mixture was diluted with dichloromethane (200 ml) and washed with water (200 ml), saturated brine (100 ml) and the organic layer was concentrated under reduced pressure to afford the desired compound (15.48 g, yield: 100%). The crude product was used in the next step without further purification.

Step 2: Synthesis of (S)-tert-butyl 2-(4-phenyl-1H-imidazol-2-yl)pyrrolidine-1-carboxylate

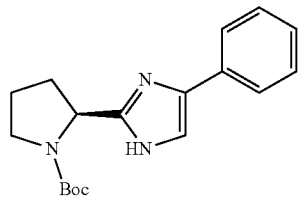 [SMILES: CC(C)(C)OC(=O)N1CCC[C@H]1c1nc(-c2ccccc2)c[nH]1]

To a stirred solution of (S)-1-tert-butyl 2-(2-oxo-2-phenylethyl)pyrrolidine-1,2-dicarboxylate (step 1, 15.40 g, 46.24 mmol) in toluene (180 ml), ammonium acetate (30.29 g, 393.09 mmol) was added at room temperature and refluxed for about 16 hours. After completion of the reaction (monitored by TLC), the reaction mixture was diluted with ethyl acetate (200 ml), water and the organic layer was washed with 0.5N HCl (2×150 ml). Aqueous layer was basified with 2N NaOH (150 ml), the precipitated solid was filtered and dried to afford the desired compound (11.6 g, yield: 80%) as an off white solid. HPLC purity: 99%.

Step 3: Synthesis of (S)-tert-butyl 2-(1-methyl-4-phenyl-1H-imidazol-2-yl)pyrrolidine-1-carboxylate

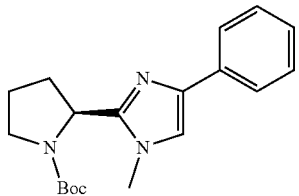 [SMILES: Cn1cc(-c2ccccc2)nc1[C@@H]1CCCN1C(=O)OC(C)(C)C]

A solution of (S)-tert-butyl 2-(4-phenyl-1H-imidazol-2-yl)pyrrolidine-1-carboxylate (step 2, 2.0 g, 6.38 mmol) in DMF (20 ml) was treated with sodium hydride (60% in oil, 0.90 g, 19.16 mmol) at 0° C. After stirring about 15 minutes at 0° C., methyl iodide (0.8 ml, 12.77 mmol) was added and stirred at ambient temperature for about 24 hours. After completion of the reaction (monitored by TLC), the reaction was quenched with ice water, extracted with ethyl acetate (2×100 ml), and washed with brine, dried over $Na_2SO_4$ and concentrated. The residue was purified by silica gel column chromatography using 10% ethyl acetate/hexanes as eluent to afford the desired compound (1.80 g, yield: 86%). $H^1$ NMR (DMSO-$D_6$, 300 MHz): δ 7.68 (d, J=7.5 Hz, 2H), 7.45 (s, 1H), 7.31 (t, J=7.5 Hz, 2H), 7.15 (t, J=7.5 1H), 4.89 (m, 1H), 3.63 & 3.71 (2s, 3H), 3.48 (m, 2H), 2.23 (m, 2H), 1.88 (m, 2H), 1.28 & 1.36 (2s, 9H).

Step 4: Synthesis of (S)-1-methyl-4-phenyl-2-(pyrrolidin-2-yl)-1H-imidazole

To a solution of (S)-tert-butyl 2-(1-methyl-4-phenyl-1H-imidazol-2-yl)pyrrolidine-1-carboxylate (step 3, 1.80 g, 5.50 mmol) in dichloromethane (20 ml) was added trifluoroacetic acid (7 ml) and stirred at room temperature for about 4 hours. After completion the reaction (monitored by TLC), the reaction mixture was quenched with aqueous sodium bicarbonate solution and extracted with dichloromethane (2×100 ml), washed with brine, dried over $Na_2SO_4$ and filtered. The solvents were evaporated under reduced pressure to afford the desired compound (1.20 g, yield: 96%). $H^1$ NMR (DMSO-$D_6$, 300 MHz): δ 7.72 (d, J=7.5 Hz, 2H), 7.58 (s, 1H), 7.33 (t, J=7.5 Hz, 2H), 7.16 (t, J=7.5 1H), 4.34 (t, J=7.2 Hz, 1H), 3.68 (s, 3H), 2.87-3.05 (m, 2H), 2.12 (m, 2H), 1.78-1.93 (2H).

The below intermediates were prepared by the procedure similar to the one described in the synthesis of Intermediate-1 with appropriate variations in reactants and quantities of reagents. The characterization data of the intermediates are summarized herein below table.

| Intermediate no | Starting material | Reagent | Structure | Characterization data |
|---|---|---|---|---|
| 2. | | | 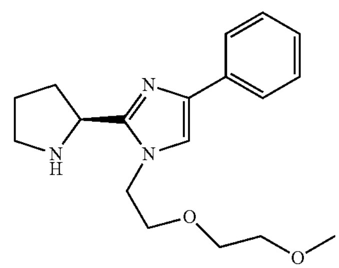 [SMILES: COCCOCCn1cc(-c2ccccc2)nc1[C@@H]1CCCN1] | $H^1$ NMR (DMSO-$D_6$, 300 MHz): δ 7.72 (d, J = 7.5 Hz, 2H), 7.62 (s, 1H), 7.32 (t, J = 7.5 Hz, 2H), 7.15 (t, J = 7.5, 1H), 4.34 (t, J = 7.2 Hz, 1H), 4.20 (m, 2H), 3.72 (m, 2H), 3.4-3.60 (m, 4H), 3.23 (s, 3H), 3.05 (m, 1H), 2.95 (m, 1H), 2.10 (m, 2H), 1.80 (m, 2H). |
| 3. | | | 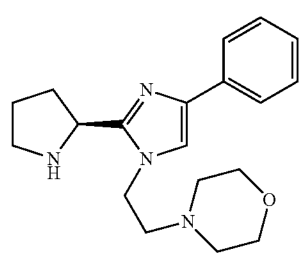 [SMILES: c1ccc(-c2cn(CCN3CCOCC3)c([C@@H]3CCCN3)n2)cc1] | $H^1$ NMR (DMSO-$D_6$, 300 MHz): δ 7.73 (d, J = 7.5 Hz, 2H), 7.66 (s, 1H), 7.33 (t, J = 7.5 Hz, 2H), 7.18 (t, J = 7.5 1H), 4.45 (t, J = 7.2 Hz, 1H), 4.15 (m, 2H), 3.57 (m, 4H), 3.10 (m, 1H), 2.95 (m, 1H), 2.67 (m, 2H), 2.46 (m, 4H), 2.17 (m, 2H), 1.8-2.0 (m, 2H). |

-continued

| Intermediate no | Starting material | Reagent | Structure | Characterization data |
|---|---|---|---|---|
| 4. | (2-phenyl-imidazol-pyrrolidine-Boc) | Br-CH₂CH₂-OMe | (N-(2-methoxyethyl)-imidazole product) | H¹ NMR (DMSO-D₆, 300 MHz): δ 7.74 (d, J = 7.5 Hz, 2H), 7.62 (s, 1H), 7.32 (t, J = 7.5 Hz, 2H), 7.15 (t, J = 7.5 1H), 4.34 (t, J = 7.2 Hz, 1H), 4.22 (m, 2H), 3.65 (m, 2H), 3.25 (s, 3H), 3.10 (m, 1H), 2.95 (m, 1H), 2.15 (m, 2H), 1.8-2.0 (m, 2H). |
| 5. | (2-phenyl-imidazol-pyrrolidine-Boc) | Me₂N-CH₂CH₂-Cl·ClH | (N-(2-dimethylaminoethyl) product) TFA | H¹ NMR (DMSO-D₆, 300 MHz): δ 7.75 (d, J = 7.5 Hz, 2H), 7.32 (t, J = 7.5 Hz, 2H), 7.18 (t, J = 7.5 1H), 7.12 (s, 1H), 4.34 (t, J = 7.2 Hz, 1H), 4.23 (m, 2H), 2.9-3.05 (m, 2H), 2.65 (m, 2H), 2.29 (s, 6H), 2.22 (m, 2H), 1.8.20 (m, 2H). |
| 6. | (2-phenyl-imidazol-pyrrolidine-Boc) | 1-(2-chloroethyl)pyrrolidine·ClH | (N-(2-pyrrolidinylethyl) product) TFA | H¹ NMR (DMSO-D₆, 300 MHz): δ 10.19 (bs, 1H), 7.85 (s, 1H), 7.76 (d, J = 7.5 Hz, 2H), 7.40 (t, J = 7.5 Hz, 2H), 7.25 (t, J = 7.5 1H), 4.94 (m, 1H), 4.40 (m, 2H), 3.65 (m, 4H), 3.3-3.50 (m, 2H), 3.13 (m 2H), 2.15-2.30 (m, 2H), 1.80-2.10 (m, 6H); |
| 7. | (2-(3-fluorophenyl)-imidazol-pyrrolidine-Boc) | Me₂N-CH₂CH₂-Cl·ClH | (product) TFA | H¹ NMR (DMSO-D₆, 300 MHz): δ 8.95 (bs, 1H), 7.93 (s, 1H), 7.56 (m, 2H), 7.42 (m, 1H), 7.06 (m, 1H), 4.96 (m, 1H), 4.46 (m, 2H), 3.55 (m, 2H), 3.32-3.50 (m, 2H), 2.89 (s, 6H), 2.42 (m, 1H), 2.21 (m, 2H), 2.05 (m, 1H). |
| 8. | (2-(4-fluorophenyl)-imidazol-pyrrolidine-Boc) | Me₂N-CH₂CH₂-Cl·ClH | (product) TFA | H¹ NMR (DMSO-D₆, 300 MHz): δ 8.97 (bs, 1H), 7.83 (s, 1H), 7.79 (dd, J = 6.0, 7.5 Hz, 2H), 7.24 (t, J = 9.7 Hz, 2H), 4.96 (m, J = 7.2 Hz, 1H), 4.46 (m, 2H), 3.55 (m, 2H), 3.42 (m, 2H), 2.89 (s, 6H), 2.42 (m, 1H), 2.21 (m, 2H), 2.05 (m, 1H). |

| Intermediate no | Starting material | Reagent | Structure | Characterization data |
|---|---|---|---|---|
| 9. | (structure with Boc-pyrrolidine-imidazole-pyridin-3-yl) | N,N-dimethyl-2-chloroethylamine·HCl | (product with dimethylaminoethyl, TFA salt) | H¹ NMR (DMSO-D$_6$, 300 MHz): δ 9.78 & 10.09 (2 bs, 1H), 9.09 (s, 1H), 8.65 (d, J = 5.0 Hz, 1H), 8.43 (d, J = 9.0 Hz, 1H), 7.95 (s, 1H), 7.76 (dd, J = 6.0, 9.0 Hz, 1H), 4.98 (m, 1H), 4.48 (m, 2H), 3.56 (m, 2H), 3.42 (m, 2H), 2.89 (s, 6H), 2.45 (m, 1H), 2.65 (m, 2H), 2.22 (m, 2H), 2.10 (m, 1H). |
| 10. | (structure with Boc-pyrrolidine-imidazole-pyridin-4-yl) | N,N-dimethyl-2-chloroethylamine·HCl | (product with dimethylaminoethyl, TFA salt) | H¹ NMR (DMSO-D$_6$, 300 MHz): δ 9.86 (bs, 1H), 8.87 (d, J = 7.3 Hz, 2H), 8.57 (s, 1H), 8.25 (d, J = 7.3 Hz, 2H), 5.05 (m, 1H), 4.54 (m, 2H), 3.60 (m, 2H), 3.45 (m, 2H), 2.89 (s, 6H), 2.42 (m, 1H), 2.21 (m, 2H), 2.05 (m, 1H). |
| 11. | (structure with Boc-pyrrolidine-imidazole-pyridin-4-yl) | 1-(2-chloroethyl)pyrrolidine·HCl | (product with pyrrolidinylethyl, TFA salt) | H¹ NMR (DMSO-D6, 300 MHz): δ 10.11 (bs, 1H), 8.90 (d, J = 6.3 Hz, 2H), 8.26 (d, J = 6.3 Hz, 2H), 7.95 (s, 1H), 5.06 (m, 1H), 4.55 (m, 2H), 3.55-3.75 (m, 4H), 3.42 (m, 2H), 3.0-3.25 (m, 2H), 2.05-2.35 (m, 2H), 1.85-2.10 (m, 6H); |

Intermediate 12: Preparation of (S)-2-(4-tert-butyl-2-(pyrrolidin-2-yl)-1H-imidazol-1-yl)-N,N-dimethylethanamine 2,2,2-trifluoroacetate Step 1: Synthesis of (S)-tert-butyl 2-(3,3-dimethyl-2-oxobutylcarbamoyl)pyrrolidine-1-carboxylate

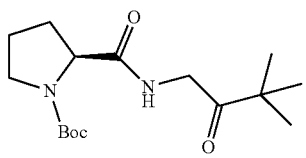 [SMILES: CC(C)(C)OC(=O)N1CCC[C@H]1C(=O)NCC(=O)C(C)(C)C]

To a stirred solution of (S)-1-(tert-butoxycarbonyl)pyrrolidine-2-carboxylic acid (15.40 g, 71.69 mmol) in DMF (100 ml) at 0° C. was added DIPEA (37.40 ml, 220.5 mmol) and HATU (28.0 g, 71.69 mmol). After 20 minutes 1-amino-3,3-dimethylbutan-2-one hydrochloride (7.50 g, 49.66 mmol) was added and the reaction mixture was allowed to stir at room temperature for about 18 hours. After completion of the reaction (monitored by TLC), the reaction mixture was extracted with ethyl acetate (2×250 ml), washed with water (200 ml), saturated brine (100 ml) and the organic layer was concentrated under reduced pressure. The residue was purified by column chromatography (silica gel 100-200 mesh, 15-20% ethyl acetate in hexanes) to afford the title compound (11.3 g, yield: 51%). H¹ NMR (DMSO-d6, 300 MHz): δ 7.90 (broad t, 1H), 4.12 (m, 3H), 3.25-3.45 (m, 2H), 2.10 (m, 1H), 1.75-1.90 (m, 3H), 1.33&1.39 (2s, 9H), 1.11 (s, 9H).

Step 2: Synthesis of (S)-tert-butyl 2-(4-tert-butyl-1H-imidazol-2-yl)pyrrolidine-1-carboxylate

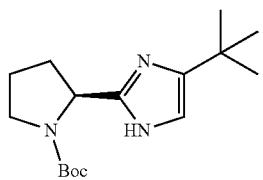 [SMILES: CC(C)(C)OC(=O)N1CCC[C@H]1c1nc(C(C)(C)C)c[nH]1]

To a stirred solution of (S)-tert-butyl 2-(3,3-dimethyl-2-oxobutylcarbamoyl) pyrrolidine-1-carboxylate (step 1, 11.3 g, 36.33 mmol) in xylene (130 ml), ammonium acetate (56.0 g, 726.6 mmol) was added at room temperature and heated at 140° C. for about 48 hours. After completion of the reaction (monitored by TLC), the reaction mixture was cooled to room temperature, the pH was adjusted (pH~7-8) with aq. NaHCO$_3$ solution and extracted with ethyl acetate (2×300 ml). The organic layer was washed with 1 N HCl (2×200 ml) and then the aqueous layer was basified with 2N NaOH (200 ml), product was extracted with ethyl acetate (2×300 ml), washed with brine, dried over Na$_2$SO$_4$, filtered and concentrated to afford the title compound (3.70 g, Yield: 35%) as an off white solid. H$^1$ NMR (DMSO-d6, 300 MHz): δ 7.90 (broad peak, 1H), 6.54 (broad s, 1H), 4.65 (m, 1H), 3.25-3.45 (m, 2H), 2.10 (m, 1H), 1.75-1.90 (m, 3H), 1.33&1.39 (2s, 9H), 1.11 (s, 9H); Mass (ESI): 294.29 [M+H]$^+$.

Step 3: Synthesis of (S)-tert-butyl 2-(4-tert-butyl-1-(2-(dimethylamino)ethyl)-1H-imidazol-2-yl)pyrrolidine-1-carboxylate

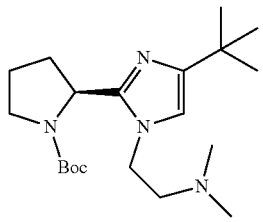 [SMILES: CN(C)CCn1cc(C(C)(C)C)nc1[C@@H]1CCCN1C(=O)OC(C)(C)C]

A solution of (S)-tert-butyl 2-(4-tert-butyl-1H-imidazol-2-yl)pyrrolidine-1-carboxylate (step 2, 2.0 g, 6.87 mmol) in DMF (20 ml) was treated with sodium hydride (60% in oil, 494 mg, 20.61 mmol) at 0° C. After stirring about 15 minutes at 0° C., a solution of 2-(dimethylamino) ethyl chloride hydrochloride (1.90 g, 13.74 mmol), triethyl amine (2.0 ml, 13.74 mmol) in DMF (10 ml) was added and stirred at ambient temperature for about 18 hours. After completion of the reaction (monitored by TLC), the reaction was quenched with ice water, extracted with ethyl acetate (2×100 ml), washed with brine, dried over Na$_2$SO$_4$ and concentrated to afford the title compound (2.3 g, Yield: 92%). H$^1$ NMR (CDCl$_3$, 300 MHz): δ 6.47 (s, 1H), 4.78 (m, 1H), 3.8-4.20 (m, 2H), 3.5-3.70 (m, 2H), 2.50-2.80 (m, 2H), 2.10 (m, 1H), 2.28 (s, 6H), 1.75-1.90 (m, 3H), 1.33&1.39 (2s, 9H), 1.11 (s, 9H).

Step 4: Synthesis of (S)-2-(4-tert-butyl-2-(pyrrolidin-2-yl)-1H-imidazol-1-yl)-N,N-dimethyl ethanamine 2,2,2-trifluoroacetate To a solution of (S)-tert-butyl 2-(4-tert-butyl-1-(2-(dimethylamino)ethyl)-1H-imidazol-2-yl)pyrrolidine-1-carboxylate (step 3, 2.30 g, 6.35 mmol) in dichloromethane (30 ml) was added trifluoroacetic acid (15 ml) and stirred at room temperature for about 3 hours. After completion of the reaction (monitored by TLC), the solvents were evaporated under reduced pressure to afford the title compound (2.10 g, Yield: 87%). H$^1$ NMR (DMSO-D$_6$, 300 MHz): δ 10.10 (broad peak, 1H), 7.29 (s, 1H), 5.0 (m, 1H), 4.46 (m, 2H), 3.55 (m, 2H), 3.35 (m, 2H), 2.86 (s, 6H), 2.0-2.50 (m, 4H), 1.11 (s, 9H); Mass (ESI): 265.20 [M+H]$^+$.

Intermediate 13: Preparation of (S)-2-(4-isopropyl-2-(pyrrolidin-2-yl)-1H-imidazol-1-yl)-N,N-dimethylethanamine 2,2,2-trifluoroacetate

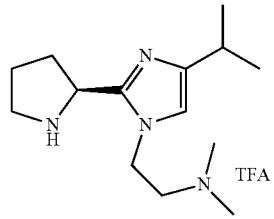 [SMILES: CC(C)c1cn(CCN(C)C)c([C@@H]2CCCN2)n1]

Step 1: Synthesis of (S)-tert-butyl 2-(3-methyl-2-oxobutylcarbamoyl)pyrrolidine-1-carboxylate

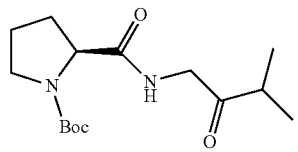 [SMILES: CC(C)C(=O)CNC(=O)[C@@H]1CCCN1C(=O)OC(C)(C)C]

To a stirred solution of (S)-1-(tert-butoxycarbonyl)pyrrolidine-2-carboxylic acid (10.0 g, 46.51 mmol) in DMF (80 ml) at 0° C. was added DIPEA (32.0 ml, 186.0 mmol) and HATU (23.6 g, 60.46 mmol). After 20 minutes 1-amino-3-methylbutan-2-one hydrochloride (5.06 g, 37.2 mmol) was added and the reaction mixture was allowed to stir at room temperature for about 18 hours. After completion of the reaction (monitored by TLC), the reaction mixture was extracted with ethyl acetate (2×250 ml), washed with water (200 ml), saturated brine (100 ml) and the organic layer was concentrated under reduced pressure. The residue was purified by column chromatography (silica gel 100-200 mesh, 30-40% ethyl acetate in hexanes) to afford the title compound (8.10 g, Yield: 58%). H$^1$ NMR (DMSO-d6, 300 MHz): δ 8.02 (broad t, 1H), 4.14 (m, 1H), 3.95 (m, 2H), 3.25-3.50 (m, 2H), 2.72 (m, 1H), 2.10 (m, 1H), 1.75-1.90 (m, 3H), 1.33&1.39 (2s, 9H), 1.01 (d, J=8.0 Hz, 6H).

Step 2: Synthesis of (S)-tert-butyl 2-(4-isopropyl-1H-imidazol-2-yl)pyrrolidine-1-carboxylate

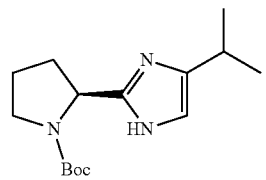 [SMILES: CC(C)c1c[nH]c([C@@H]2CCCN2C(=O)OC(C)(C)C)n1]

To a stirred solution of (S)-tert-butyl 2-(3-methyl-2-oxobutylcarbamoyl)pyrrolidine-1-carboxylate (step 1, 6.0 g, 20.13 mmol) in xylene (100 ml), ammonium acetate (17.0 g, 221.0 mmol) was added at room temperature and heated at 140° C. for about 48 hours. After completion of the reaction (monitored by TLC), the reaction mixture was cooled to room temperature, the pH was adjusted (pH~7-8) with aq. NaHCO$_3$ solution and extracted with ethyl acetate (2×300 ml). The organic layer was washed with 1 N HCl (2×200 ml), the aqueous layer was basified with 2N NaOH (200 ml), product was extracted with ethyl acetate (2×300 ml), washed with brine, dried over Na$_2$SO$_4$, filtered and concentrated to afford the title compound (1.50 g, Yield: 26%) as a solid. H¹ NMR (DMSO-d6, 300 MHz): δ 11.40 (broad peak, 1H), 6.53 (broad s, 1H), 4.65 (m, 1H), 3.45 (m, 2H), 2.73 (m, 1H), 2.10 (m, 1H), 1.75-1.90 (m, 3H), 1.33&1.39 (2s, 9H), 1.18 (d, J=8.0 Hz, 6H); Mass (ESI): 280.11 [M+H]⁺.

Step 3: Synthesis of (S)-tert-butyl 2-(1-(2-(dimethylamino)ethyl)-4-isopropyl-1H-imidazol-2-yl)pyrrolidine-1-carboxylate

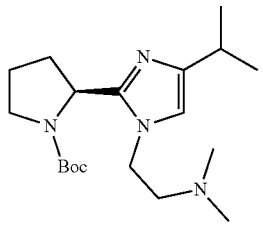 [SMILES: CC(C)c1cn(CCN(C)C)c([C@@H]2CCCN2C(=O)OC(C)(C)C)n1]

A solution of (S)-tert-butyl 2-(4-isopropyl-1H-imidazol-2-yl)pyrrolidine-1-carboxylate (step 2, 1.50 g, 5.37 mmol) in DMF (20 ml) was treated with sodium hydride (60% in oil, 387 mg, 16.12 mmol) at 0° C. After stirring about 15 minutes at 0° C., a solution of 2-(dimethylamino)ethyl chloride hydrochloride (1.54 g, 10.75 mmol), triethyl amine (1.30 ml, 10.75 mmol) in DMF (10 ml) was added and stirred at ambient temperature for about 18 hours. After completion of the reaction (monitored by TLC), the reaction was quenched with ice water, extracted with ethyl acetate (2×100 ml), washed with brine, dried over Na₂SO₄ and concentrated to afford the title compound (1.57 g, Yield: 79%). H¹ NMR (DMSO-D₆, 300 MHz): δ 6.68 (s, 1H), 4.72 (m, 1H), 3.8-4.20 (m, 2H), 3.3-3.60 (m, 2H), 2.67 (m, 1H), 2.50-2.80 (m, 2H), 2.10 (m, 1H), 2.16 (s, 6H), 1.75-1.90 (m, 3H), 1.33&1.18 (2s, 9H), 1.11 (d, J=8.0 Hz, 6H); Mass (ESI): 351.39 [M+H]⁺.

Step 4: Synthesis of (S)-2-(4-isopropyl-2-(pyrrolidin-2-yl)-1H-imidazol-1-yl)-N,N-dimethyl ethanamine 2,2,2-trifluoroacetate To a solution of (S)-tert-butyl 2-(1-(2-(dimethylamino)ethyl)-4-isopropyl-1H-imidazol-2-yl)pyrrolidine-1-carboxylate (step 3, 1.50 g, 4.28 mmol) in dichloromethane (30 ml) was added trifluoroacetic acid (10 ml) and stirred at room temperature for about 4 hours. After completion of the reaction (monitored by TLC), the solvents were evaporated under reduced pressure to afford the title compound (1.50 g, Yield: 96%). H¹ NMR (DMSO-D₆, 300 MHz): δ 10.0 (broad peak, 1H), 7.17 (s, 1H), 4.86 (m, 1H), 4.30-4.55 (m, 2H), 3.25-3.60 (m, 4H), 2.85 (s, 6H), 2.83 (m, 1H), 1.95-2.20 (m, 4H), 1.20 (d, J=8.0 Hz, 6H).

Intermediate 14: Preparation of 2-((2S,4R)-4-(2-methoxyethoxy)pyrrolidin-2-yl)-4-phenyl-1H-imidazole

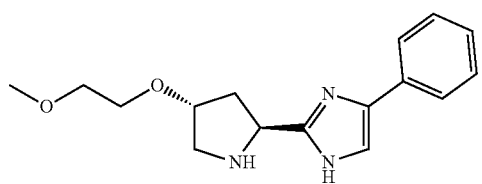 [SMILES: COCCO[C@H]1CN[C@H](c2nc(-c3ccccc3)c[nH]2)C1]

Step 1: Synthesis of (2S,4R)-1-(tert-butoxycarbonyl)-4-hydroxypyrrolidine-2-carboxylic acid

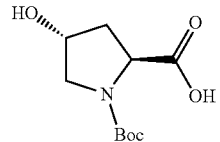 [SMILES: CC(C)(C)OC(=O)N1C[C@H](O)C[C@H]1C(=O)O]

To a stirred solution of (2S,4R)-4-hydroxypyrrolidine-2-carboxylic acid (50.0 g, 381.3 mmol) in 1,4-dioxane (250 ml) at 0° C. was added aqueous NaHCO₃ (96.10 g dissolved in 500 ml of H₂O, 1144 mmol). After stirring about 10 minutes at 0° C., the reaction mixture was treated with di-tert-butyl dicarbonate (99.86 g, 457.5 mmol) and the resulting solution was stirred at room temperature for about 18 hours. TLC indicated starting material was consumed and the desired product was observed. The reaction mixture was poured into ice cold water, the solution pH was adjusted to 2 to 3 by addition of 4N HCl (Note: the temperature of reaction mixture should be 5-10° C.). The aqueous layer was extracted with ethyl acetate (2×500 ml), combined organic layer was washed with brine, dried over Na₂SO₄, filtered and solvent was evaporated under reduced pressure to provide the title compound (85.0 g, yield: 96%).

Step 2: Synthesis of (2S,4R)-1-(tert-butoxycarbonyl)-4-(2-methoxyethoxy)pyrrolidine-2-carboxylic acid

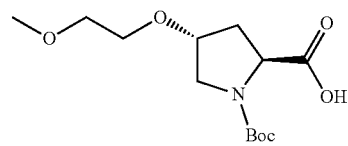 [SMILES: COCCO[C@@H]1C[C@@H](C(=O)O)N(C(=O)OC(C)(C)C)C1]

A solution of (2S,4R)-1-(tert-butoxycarbonyl)-4-hydroxypyrrolidine-2-carboxylic acid (step 1, 20.0 g, 86.9 mmol) in DMF (200 ml) was treated with sodium hydride (8.43 g, 347.8 mmol) at 0° C. After stirring about 15 minutes at 0° C., 1-bromo-2-methoxyethane (24.2 g, 174.0 mmol) was added and stirred at ambient temperature for about 18 hours. TLC indicated starting material was consumed and the desired product was observed. The reaction mixture was cooled to 0° C. then added 400 ml water slowly over about 30 minutes and stirred at room temperature for about 4 hours. Ethyl acetate (200 ml) was added to the reaction mixture and the two layers were separated. Aqueous layer was acidified (pH~5) with 6N HCl, extracted with ethyl acetate (2×300 ml), washed with brine, dried over Na₂SO₄, filtered and concentrated to afford the title compound (14.50 g, yield: 58%). H¹ NMR (DMSO-D₆, 300 MHz): δ 12.58 (bs, 1H), 4.05 (m, 2H), 3.50 (m, 2H), 3.41 (m, 4H), 3.23 (s, 1H), 2.26 (m, 1H), 1.97 (m, 1H), 1.39 & 1.34 (2s, 9H).

Step 3: Synthesis of 2-((2S,4R)-4-(2-methoxy-ethoxy)pyrrolidin-2-yl)-4-phenyl-1H-imidazole

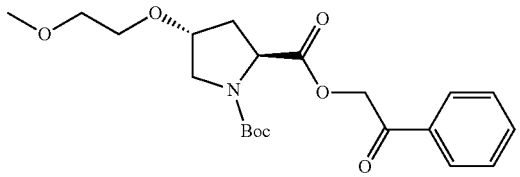 [SMILES: COCCO[C@@H]1C[C@@H](C(=O)OCC(=O)c2ccccc2)N(C(=O)OC(C)(C)C)C1]

To a stirred solution of (2S,4R)-1-(tert-butoxycarbonyl)-4-(2-methoxyethoxy) pyrrolidine-2-carboxylic acid (step 2, 3.20 g, 11.07 mmol) in DCM (50 ml) was added DIPEA (3.80 ml, 22.14 mmol) at 0° C. After stirring about 10 minutes 2-bromo-1-phenylethanone (2.20 g, 11.07 mmol) was added and the reaction mixture was allowed to stir at room temperature for about 18 hours. After completion of the reaction (monitored by TLC), the reaction mixture was diluted with dichloromethane (200 ml) and washed with water (200 ml), brine solution (100 ml) and the organic layer was concentrated under reduced pressure to afford the crude product (4.5 g) which was used in the next step without further purification. H$^1$ NMR (DMSO-D$_6$, 300 MHz): δ 7.96 (d, J=8.0 Hz, 2H), 7.70 (t, J=8.0 Hz, 1H), 7.56 (t, J=8.0 Hz, 2H), 5.56 (s, 2H), 4.35 (m, 1H), 4.15 (m, 1H), 3.57 (m, 2H), 3.44 (m, 4H), 3.23 (s, 3H), 2.41 (m, 1H), 2.26 (m, 1H), 1.36 & 1.25 (2s, 9H).

Step 4: Synthesis of (2S,4R)-tert-butyl 4-(2-methoxyethoxy)-2-(4-phenyl-1H-imidazol-2-yl)pyrrolidine-1-carboxylate

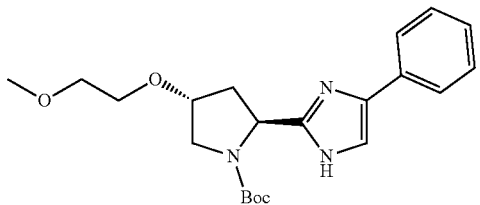 [SMILES: COCCO[C@@H]1C[C@@H](c2nc(-c3ccccc3)c[nH]2)N(C(=O)OC(C)(C)C)C1]

To a stirred solution of (2S,4R)-1-tert-butyl 2-(2-oxo-2-phenylethyl)4-(2-methoxyethoxy) pyrrolidine-1,2-dicarboxylate (step 3, 4.5 g, 11.05 mmol) in toluene (50 ml), ammonium acetate (8.52 g, 110.56 mmol) was added at room temperature and refluxed for about 18 hours. After completion of the reaction (monitored by TLC), the reaction mixture was diluted with water, extracted with ethyl acetate (200 ml) and the organic layer was washed with 1N HCl (2×100 ml). Aqueous layer was basified with 2N NaOH (pH~8 to 9), the product was extracted with ethyl acetate (2×100 ml), washed with brine, dried over Na$_2$SO$_4$, filtered and concentrated to afford the title compound (4.0 g, yield: 93%). H$^1$ NMR (DMSO-D$_6$, 300 MHz): δ 11.91 (bs, 1H), 7.71 (d, J=8.0 Hz, 2H), 7.48 (s, 1H), 7.31 (t, J=8.0 Hz, 2H), 7.15 (t, J=8.0 Hz, 1H), 4.75 (m, 1H), 4.18 (m, 1H), 3.4-3.60 (m, 6H), 3.26 (s, 3H), 2.34 (m, 1H), 2.08 (m, 1H), 1.38 & 1.20 (2s, 9H).

Step 5: Synthesis of 2-((2S,4R)-4-(2-methoxy-ethoxy)pyrrolidin-2-yl)-4-phenyl-1H-imidazole To a solution of (2S,4R)-tert-butyl 4-(2-methoxyethoxy)-2-(4-phenyl-1H-imidazol-2-yl)pyrrolidine-1-carboxylate (step 4, 4.0 g, 10.36 mmol) in DCM (40 ml) was added trifluoroacetic acid (10 ml) and stirred at room temperature for about 4 hours. After completion of the reaction (monitored by TLC), the solvents were evaporated and aqueous sodium bicarbonate was added to the residue. The product was extracted with dichloromethane (2×100 ml), washed with brine, dried over Na$_2$SO$_4$, filtered and the solvents were evaporated under reduced pressure to afford the title compound (2.1 g, yield: 69%). H$^1$ NMR (DMSO-D$_6$, 300 MHz): δ 11.86 (bs, 1H), 7.72 (d, J=8.0 Hz, 2H), 7.44 (s, 1H), 7.31 (t, J=8.0 Hz, 2H), 7.30 (m, 1H), 7.15 (t, J=8.0 Hz, 1H), 4.28 (t, J=8.6 Hz, 1H), 4.10 (m, 1H), 3.4-3.60 (m, 4H), 3.26 (s, 3H), 3.13 (m, 1H), 2.87 (m, 1H), 2.15 (m, 2H).

The below intermediate was prepared by the procedure similar to the one described in the synthesis of Intermediate-14 with appropriate variations in reactants and quantities of reagents. The characterization data of the intermediate is summarized herein below table.

| Intermediate no | Intermediate Structure | Characterization data |
| --- | --- | --- |
| 15. | | H$^1$ NMR (DMSO-D$_6$, 300 MHz): δ 9.90 (bs, 1H), 9.19 (bs, 1H), 7.82 (s, 1H), 7.61 (m, 2H), 7.41 (s, 1H), 7.08 (m, 1H), 4.81 (m, 1H), 4.41 (m, 1H), 3.3-3.60 (m, 6H), 3.27 (s, 3H), 2.3-2.60 (m, 2H). |

Intermediate 16: Preparation of (S)-2-(pyrrolidin-2-yl)-1H-benzo[d]imidazole TFA salt

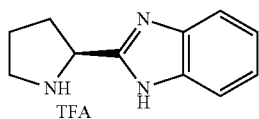 [SMILES: c1ccc2[nH]c([C@@H]3CCCN3)nc2c1]

Step 1: Synthesis of (S)-tert-butyl 2-(1H-benzo[d]imidazol-2-yl)pyrrolidine-1-carboxylate

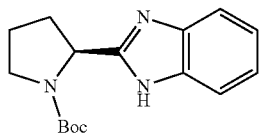 [SMILES: CC(C)(C)OC(=O)N1CCC[C@H]1c1nc2ccccc2[nH]1]

To a stirred solution (S)-1-(tert-butoxycarbonyl)pyrrolidine-2-carboxylic acid (7.13 g, 33.3 mmol) in DMF (50 ml) were added DIPEA (19.6 ml, 110.8 mmol), EDC (6.4 g, 33.3 mmol) and HOBt (4.47 g, 33.3 mmol). After stirring about 10 minutes, o-phenylenediamine (5.0 g, 27.7 mmol) was added and the reaction mixture was stirred at room temperature for about 18 hours, then at 100° C. for about 6 hours. After completion of the reaction (monitored by TLC), the reaction mixture was diluted with water, extracted with ethyl acetate (200 ml), washed with saturated brine (100 ml) and the organic layer was concentrated under reduced pressure to afford title compound (2.0 g, yield: 21%). The crude product was used in the next step without further purification. $H^1$ NMR (DMSO-$D_6$, 300 MHz): δ 12.22 (broad s, 1H), 7.47 (m, 2H), 7.11 (m, 2H), 4.92 (m, 1H), 3.60 (m, 1H), 3.39 (m, 1H), 2.30 (m, 1H), 1.85-2.03 (m, 3H), 1.39 & 1.06 (2s, 9H).

Step 2: Synthesis of (S)-2-(pyrrolidin-2-yl)-1H-benzo[d]imidazole TFA salt

To a solution of (S)-tert-butyl 2-(1H-benzo[d]imidazol-2-yl)pyrrolidine-1-carboxylate (step 1, 2.0 g, 6.90 mmol) in DCM (20 ml) was added trifluoroacetic acid (2.6 ml, 34.84 mmol) and stirred at room temperature for about 2 hours. After completion of the reaction (monitored by TLC), the solvents were evaporated under reduced pressure to afford title compound (2.0 g, yield: 100%) as a TFA salt. $H^1$ NMR (DMSO-$D_6$, 300 MHz): δ 9.8 (bs, 1H), 9.0 (broad peak, 1H), 7.63 (m, 2H), 7.27 (m, 2H), 4.98 (m, 1H), 3.3-3.45 (m, 2H), 2.05-2.25 (m, 4H).

Intermediate 17: Preparation of (S)-2-(4,5-dimethyl-2-(pyrrolidin-2-yl)-1H-imidazol-1-yl)-N,N-dimethylethane-1-amine TFA salt

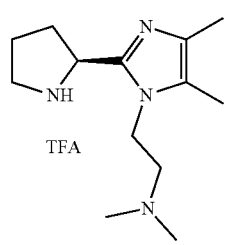 [SMILES: Cc1nc([C@@H]2CCCN2)n(CCN(C)C)c1C]

Step 1: Synthesis of tert-butyl (S)-2-(hydroxymethyl)pyrrolidine-1-carboxylate

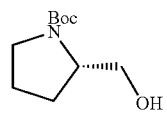

To a suspension of lithium aluminium hydride (17.6 g, 0.46 mmol, 2.0 eq) in THF (500 ml) at 0° C., (tert-butoxycarbonyl)-L-proline (50 g, 0.23 mmol, 1.0 eq) in THF (500 ml) was added dropwise over a period of about 1 hour. The reaction was allowed to stir at room temperature for about 90 minutes. After completion of the reaction (monitored by TLC), the reaction mass was quenched at 0° C. using saturated sodium sulphate, followed by addition of ethylacetate. The reaction mass was filtered over celite. The organic layer from the filtrate was separated and compound was extracted from water layer with ethylacetate. Combined organic layers were dried over anhydrous $Na_2SO_4$ and concentrated under reduced pressure. The crude compound was purified by column chromatographic technique to afford the desired compound (24 g, yield: 51%), which was used for the next step without further purification. $^1$H NMR (DMSO, 300 MHz): δ 4.67 (t, 1H, J=5.5 Hz), 3.65 (bs, 1H), 3.50-3.43 (m, 1H), 3.26-3.18 (m, 3H), 1.82-1.70 (m, 4H), 1.39 (s, 9H).

Step 2: Synthesis of tert-butyl (S)-2-formylpyrrolidine-1-carboxylate

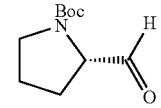

DMSO (1.9 ml, 24.87 mmol, 2 eq) dissolved in $CH_2Cl_2$ (10 ml) was slowly added in about 40 minutes to a solution of oxalyl chloride (1.4 ml, 11.65 mmol, 1.2 eq) in $CH_2Cl_2$ (20 ml) at −78° C. Afterwards a solution of tert-butyl (S)-2-(hydroxymethyl)pyrrolidine-1-carboxylate (step 1, 2.75 g, 13.68 mmol, 1 eq) in $CH_2Cl_2$ (30 ml) was added to the mixture. After stirring for about 75 minutes, DIPEA (10.0 ml, 77.51 mmol, 4 eq) was added and the mixture was allowed to warm to room temperature. After completion of the reaction (monitored by TLC), the reaction mixture was washed 3 times with 0.5M HCl (aq, 40 ml), 3 times with water (70 ml) and once with saturated NaCl solution (70 ml). The organic layer was dried over anhydrous $Na_2SO_4$ and concentrated to afford the desired compound (1.6 g, yield: 58.8%) as a white solid. $^1$H NMR (CDCl$_3$, 300 MHz): δ 1.52 (s, 9H), 1.92-2.16 (m, 4H), 3.42-3.60 (m, 1H), 4.00-4.20 (m, 1H), 9.45-9.55 (m, 1H); MS(ESI): m/z 199 (M+H)$^+$.

Step 3: Synthesis of (S)-tert-butyl 2-(4,5-dimethyl-1H-imidazol-2-yl)pyrrolidine-1-carboxylate

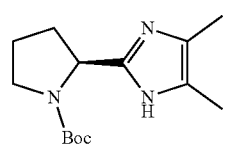 [SMILES: Cc1nc([C@@H]2CCCN2C(=O)OC(C)(C)C)[nH]c1C]

To a stirred solution of (S)-tert-butyl 2-formylpyrrolidine-1-carboxylate (step 2, 3.0 g, 15.07 mmol) in toluene (30 ml) was added 2,3-butanedione (1.29 g, 15.07 mmol), ammonium acetate (12.76 g, 165.8 mmol) and acetic acid (0.2 ml). The resulting reaction mixture was refluxed for about 16 hours. After completion of the reaction (monitored by TLC), the reaction mixture was cooled to room temperature, aq. NaHCO$_3$ solution was added, extracted with ethyl acetate (2×100 ml), combined organic layer was washed with brine, dried over Na$_2$SO$_4$, filtered and concentrated to afford the title compound (3.72 g, yield: 93%). H$^1$ NMR (DMSO-D$_6$, 300 MHz): δ 11.16 (broad s, 1H), 4.59 (m, 1H), 3.27-3.42 (m, 2H), 1.78-2.10 (m, 4H), 1.98 (s, 6H), 1.39 & 1.17 (2s, 9H).

Step 4: Synthesis of tert-butyl (S)-2-(1-(2-(dimethylamino)ethyl)-4,5-dimethyl-1H-imidazol-2-yl)pyrrolidine-1-carboxylate

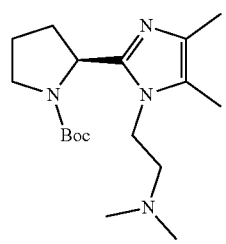 [SMILES: Cc1nc([C@@H]2CCCN2C(=O)OC(C)(C)C)n(CCN(C)C)c1C]

A solution of tert-butyl (S)-2-(4,5-dimethyl-1H-imidazol-2-yl)pyrrolidine-1-carboxylate (step 3, 3.0 g, 11.36 mmol) in DMF (40 ml) was treated with sodium hydride (60% in oil, 818 mg, 34.09 mmol) at 0° C. After stirring about 15 minutes at 0° C., a solution of 2-(dimethylamino)ethyl chloride hydrochloride (2.45 g, 17.01 mmol) and triethyl amine (2.50 ml, 17.01 mmol) in DMF (5 ml) was added and stirred at ambient temperature for about 20 hours. After completion of the reaction (monitored by TLC), the reaction was quenched with ice water, extracted with ethyl acetate (2×100 ml), and washed with brine, dried over Na$_2$SO$_4$ and concentrated to afford to afford the title compound (3.12 g, yield: 82%). H$^1$ NMR (CDCl$_3$, 300 MHz): δ 4.70-4.87 (m, 1H), 4.0 & 4.30 (m, 1H), 3.70-3.90 (m, 1H), 3.35-3.70 (m, 2H), 2.35-260 (m, 2H), 2.29 (s, 6H), 2.0-2.30 (m, 2H), 2.10 (s, 6H), 1.80-2.0 (m, 2H), 1.25 & 1.40 (2s, 9H); Mass (ESI): 337.18 [M+H]$^+$.

Step 5: Synthesis of (S)-2-(4,5-dimethyl-2-(pyrrolidin-2-yl)-1H-imidazol-1-yl)-N,N-dimethyl ethan-1-amine TFA salt To a solution of tert-butyl (S)-2-(1-(2-(dimethylamino)ethyl)-4,5-dimethyl-1H-imidazol-2-yl)pyrrolidine-1-carboxylate (step 4, 3.10 g, 9.19 mmol) in dichloromethane (30 ml) was added trifluoroacetic acid (10.51 g, 91.98 mmol) and stirred at room temperature for about 18 hours. After completion of the reaction (monitored by TLC), the solvents were evaporated under reduced pressure to afford the title compound as TFA salt (4.15 g, yield: 100%); Mass (ESI): 237.18 [M+H]$^+$.

EXAMPLES

Example 1: Preparation of (1R,3S)-2,2-dimethyl-3-(((((1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl) pyrrolidine-1-carbonyl)-1-(prop-1-en-2-yl)icosahydro-1H-cyclopenta[a]chrysen-9-yl)oxy)carbonyl) cyclobutane-1-carboxylic acid

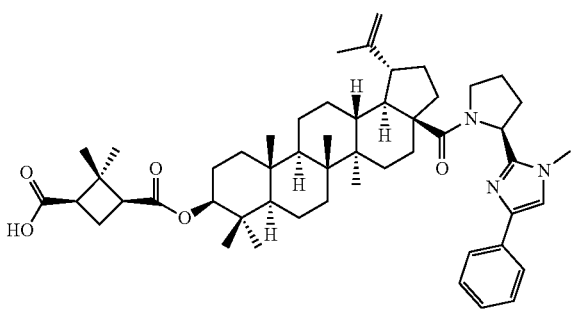

Step 1: Synthesis of (1R,3aS,5aR,5bR,7aR,9S,11aR,11bR,13aR,13bR)-5a,5b,8,8,11a-penta methyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl acetate

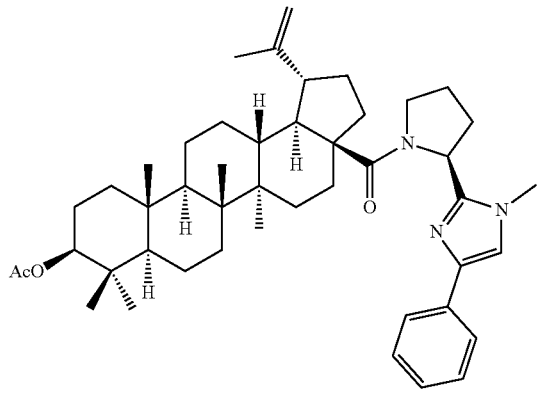

To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysen-3a-carboxylic acid (prepared as described in *J. Med. Chem.* 2009, 52, 3248-3258, 2.0 g, 4.01 mmol) in DCM (20 ml), Oxalyl chloride (1.7 ml, 20.05 mmol) was added at 0° C. and stirred at room temperature for about 3 hours. After completion of the reaction (monitored by TLC), the solvent was evaporated under nitrogen atmosphere and the residue was dissolved in DCM (20 ml) which was then added to a stirred solution of (S)-1-methyl-4-phenyl-2-(pyrrolidin-2-yl)-1H-imidazole (Intermediate 1, 900 mg, 4.01 mmol) and triethyl amine (2.0 ml, 8.02 mmol) in DCM (20 ml) at 0° C. and allowed to stir at room temperature for about 18 hours. After completion of the reaction (monitored by TLC), the reaction mixture was diluted with dichloromethane (150 ml) and washed with water, brine and organic layer was dried over $Na_2SO_4$ and filtered. The solvent was evaporated and the residue was purified on silica gel column (100-200 mesh, eluted in 30% ethyl acetate/hexanes) to afford the title compound (2.3 g, yield: 80%) as an off white solid. $H^1$ NMR (DMSO-$D_6$, 300 MHz): δ 7.64 (d, J=7.5 Hz, 2H), 7.42 (s, 1H), 7.27 (t, J=7.5 Hz, 2H), 7.11 (t, J=7.5, 1H), 5.11 (m, 1H), 4.50 (s, 1H), 4.43 (s, 1H), 4.35 (m, 1H), 3.85 (m, 1H), 3.68 (s, 3H), 3.65 (m, 1H), 2.75 (m, 1H), 2.10-2.50 (m, 3H), 1.99 (s, 3H), 0.70-2.0 (m, 43H).

Step 2: Synthesis of a 1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(1-methyl-4-phenyl-1H-imidazol-2-yl)pyrrolidin-1-yl)methanone

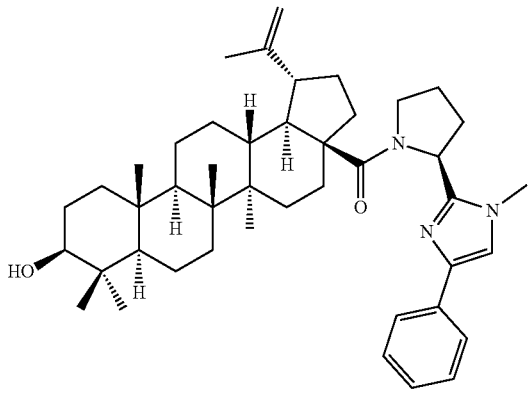

To a stirred solution of (1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl acetate (step 1, 2.3 g, 3.25 mmol) in MeOH:THF (1:1, 20 ml) was added potassium carbonate (890 mg, 6.49 mmol) and allowed to stir at room temperature for about 36 hours. After completion of the reaction (monitored by TLC), the reaction mixture was filtered and filtrate was evaporated. The residue was extracted with ethyl acetate (2×100 ml) and the organic layer was washed with water, followed by brine solution and dried over $Na_2SO_4$. The solvent was evaporated to obtain the crude compound (1.80 g, Yield: 83%), which was used in the next reaction without further purification. $H^1$ NMR (DMSO-$D_6$, 300 MHz): δ 7.64 (d, J=7.5 Hz, 2H), 7.42 (s, 1H), 7.27 (t, J=7.5 Hz, 2H), 7.11 (t, J=7.5, 1H), 5.11 (m, 1H), 4.50 (s, 1H), 4.43 (s, 1H), 4.25 (m, 1H), 3.85 (m, 1H), 3.68 (s, 3H), 3.65 (m, 1H), 2.95 (br peak, 1H), 2.75 (m, 1H), 2.10-2.60 (m, 4H), 0.70-2.0 (m, 42H).

Step 3: Synthesis of 1-benzyl 3-((1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl) (1R,3S)-2,2-dimethyl cyclobutane-1,3-dicarboxylate

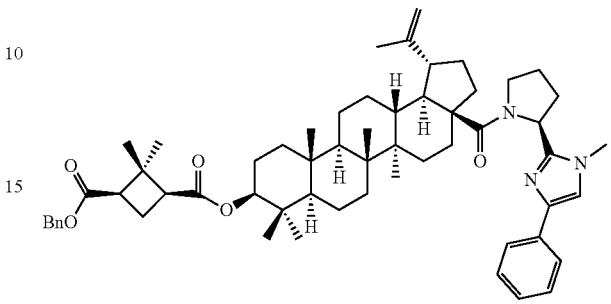

(1S,3R)-3-(benzyloxycarbonyl)-2,2-dimethylcyclobutanecarboxylic-2,4,6-trichloro benzoic anhydride (prepared as described in WO 2013/160810 A2, 528 mg, 1.12 mmol) was added to a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl) ((S)-2-(1-methyl-4-phenyl-1H-imidazol-2-yl)pyrrolidin-1-yl)methanone (step 2, 500 mg, 0.75 mmol) and DMAP (183 mg, 1.50 mmol) in toluene (30 ml) at room temperature and heated at 90° C., refluxed for about 16 hours. After completion of the reaction (monitored by TLC), the reaction mixture was diluted with ethyl acetate (200 ml) and then washed with water followed by 1N HCl, and brine solution. The solvents were dried over $Na_2SO_4$, filtered and evaporated under reduced pressure. The residue was purified on silica gel column (100-200 mesh, eluted in 15-20% ethyl acetate/hexanes) to afford the title compound (420 mg, Yield: 61%) as an off white solid. $H^1$ NMR (DMSO-$D_6$, 300 MHz): δ 7.64 (d, J=7.5 Hz, 2H), 7.42 (s, 1H), 7.34 (m, 5H), 7.27 (t, J=7.5 Hz, 2H), 7.11 (t, J=7.5, 1H), 5.11 (m, 3H), 4.50 (s, 1H), 4.43 (s, 1H), 4.32 (m, 1H), 3.85 (m, 1H), 3.68 (s, 3H), 3.65 (m, 1H), 2.90 (m, 2H), 2.10-2.60 (m, 7H), 0.70-2.0 (m, 48H).

Step 4: Synthesis of (1R,3S)-2,2-dimethyl-3-((((1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl)oxy)carbonyl) cyclobutane-1-carboxylic acid To a stirred solution of 1-benzyl 3-((1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl) (1R,3S)-2,2-dimethyl cyclobutane-1,3-dicarboxylate (step 3, 420 mg, 0.46 mmol) and ammonium formate (145 mg, 2.30 mmol) in MeOH:EtOAc (1:1, 40 ml) was added 10% Pd/C (130 mg) and stirred at ambient temperature for about 4 hours. After completion of the reaction (monitored by TLC), the catalyst was filtered through Celite bed and the filtrate was evaporated to dryness. Water was added and extracted with DCM, washed with brine, dried over $Na_2SO_4$ and concentrated. The residue was purified on silica gel column (100-200 mesh, eluted in 50-60% ethyl acetate/hexanes) to afford the title compound (220 mg, yield: 58%) as an off white solid. $H^1$ NMR (DMSO-$D_6$, 300 MHz): δ 12.15 (s, 1H), 7.64

(d, J=7.5 Hz, 2H), 7.42 (s, 1H), 7.27 (t, J=7.5 Hz, 2H), 7.11 (t, J=7.5, 1H), 5.11 (m, 1H), 4.50 (s, 1H), 4.43 (s, 1H), 4.35 (m, 1H), 3.85 (m, 1H), 3.68 (s, 3H), 3.65 (m, 1H), 2.75 (m, 2H), 2.10-2.60 (m, 7H), 0.70-2.0 (m, 48H); Mass (ESI): 820.71 [M+H]+; HPLC: 94.27%.

The below examples were prepared by the procedure similar to the one described in the synthesis of example-1 with appropriate variations in reactants and quantities of reagents. The characterization data of the examples are summarized herein below table.

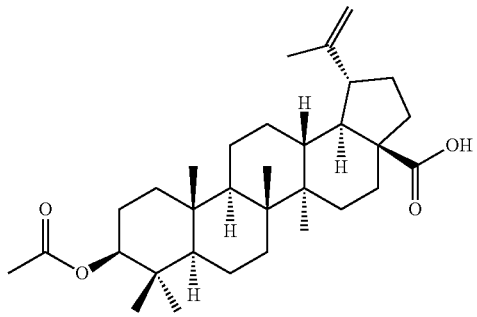

(Starting material)

| Example no | Intermediate no | Structure | Characterization data |
|---|---|---|---|
| 2. | ![imidazole intermediate] | ![example 2 structure] | H¹ NMR (DMSO-D₆, 300 MHz): δ 12.15 (s, 1H), 7.64 (d, J = 7.5 Hz, 2H), 7.46 (s, 1H), 7.27 (t, J = 7.5 Hz, 2H), 7.11 (t, J = 7.5, 1H), 5.11 (m, 1H), 4.50 (s, 1H), 4.43 (s, 1H), 4.10-4.35 (m, 3H), 3.7-3.85 (m, 3H), 3.4-3.70 (m, 5H), 3.23 (s, 3H), 2.75 (m, 2H), 2.10-2.60 (m, 7H), 0.70-2.0 (m, 48H); Mass (ESI): 908.81 [M + H]+; HPLC: 90.65%. |
| 3. | ![morpholine intermediate] | ![example 3 structure] | H¹ NMR (DMSO-D₆, 300 MHz): δ 12.12 (s, 1H), 7.65 (d, J = 7.5 Hz, 2H), 7.50 (s, 1H), 7.28 (t, J = 7.5 Hz, 2H), 7.11 (t, J = 7.5, 1H), 5.12 (m, 1H), 4.50 (s, 1H), 4.43 (s, 1H), 4.33 (m, 1H), 4.17 (m, 2H), 3.85 (m, 1H), 3.4-3.70 (m, 5H), 2.75 (m, 6H), 2.10-2.60 (m, 7H), 0.70-2.0 (m, 50H); Mass (ESI): 919.28 [M + H]+; HPLC: 88.80%. |

US 9,868,758 B2

39                                                                                       40
-continued

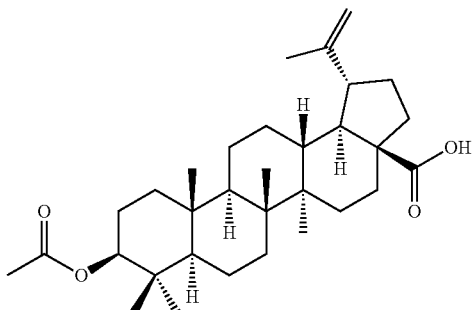

(Starting material)

| Example no | Intermediate no | Structure | Characterization data |
|---|---|---|---|
| 4. | (2-(1-(2-methoxyethyl)-4-phenyl-1H-imidazol-2-yl)pyrrolidine) | (betulinic acid derivative with cyclobutane dicarboxylate linker and 2-(1-(2-methoxyethyl)-4-phenyl-1H-imidazol-2-yl)pyrrolidine amide) | H$^1$ NMR (DMSO-D$_6$, 300 MHz): δ 12.15 (s, 1H), 7.65 (d, J = 7.5 Hz, 2H), 7.44 (s, 1H), 7.28 (t, J = 7.5 Hz, 2H), 7.11 (t, J = 7.5, 1H), 5.11 (m, 1H), 4.49 (s, 1H), 4.41 (s, 1H), 4.10-4.35 (m, 3H), 3.85 (m, 1H), 3.65 (m, 3H), 3.28 (s, 3H), 2.75 (m, 2H), 2.10-2.60 (m, 7H), 0.70-2.0 (m, 48H); Mass (ESI): 865.56 [M + H]$^+$; HPLC: 93.15%. |
| 5. | (2-(1-(2-(dimethylamino)ethyl)-4-phenyl-1H-imidazol-2-yl)pyrrolidine TFA) | (betulinic acid derivative with cyclobutane dicarboxylate linker and dimethylaminoethyl-phenyl-imidazolyl-pyrrolidine amide) | H$^1$ NMR (DMSO-D$_6$, 300 MHz): δ 12.15 (bs, 1H), 7.65 (d, J = 7.5 Hz, 2H), 7.48 (s, 1H), 7.28 (t, J = 7.5 Hz, 2H), 7.11 (t, J = 7.5, 1H), 5.11 (m, 1H), 4.49 (s, 1H), 4.42 (s, 1H), 4.33 (m, 1H), 4.10 (m, 2H), 3.85 (m, 1H), 3.67 (m, 1H), 2.70-2.75 (m, 3H), 2.23 (s, 6H), 2.10-2.60 (m, 6H), 0.70-2.0 (m, 50H); Mass (ESI): 878.67 [M + H]$^+$; HPLC: 95.12%. |
| 6. | (2-(1-(2-(dimethylamino)ethyl)-4-(pyridin-3-yl)-1H-imidazol-2-yl)pyrrolidine TFA) | (betulinic acid derivative with cyclobutane dicarboxylate linker and dimethylaminoethyl-pyridyl-imidazolyl-pyrrolidine amide) | H$^1$ NMR (DMSO-D$_6$, 300 MHz): δ 12.15 (bs, 1H), 8.86 (s, 1H), 8.32 (d, J = 4.0 Hz, 1H), 7.93 (d, J = 8.6 Hz, 1H), 7.65 (s, 1H), 7.30 (dd, J = 8.6, 4.0 Hz, 1H), 5.11 (m, 1H), 4.48 (s, 1H), 4.42 (s, 1H), 4.32 (m, 1H), 4.21 (m, 2H), 3.86 (m, 1H), 3.67 (m, 1H), 3.07 (m, 1H), 2.7-2.95 (m, 3H), 2.29 |

-continued

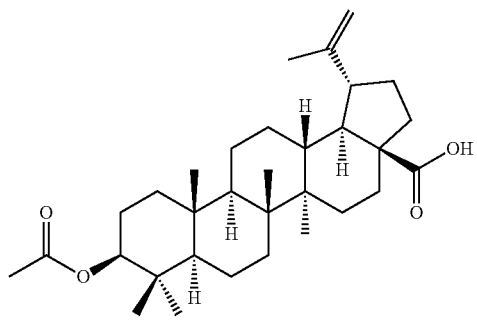

(Starting material)

| Example no | Intermediate no | Structure | Characterization data |
|---|---|---|---|
| | | | (s, 6H), 2.10-2.60 (m, 5H), 0.70-2.0 (m, 50H); Mass (ESI): 878.74 [M + H]⁺; HPLC: 92.20%. |
| 7. | (structure of pyrrolidine-imidazole-4-fluorophenyl with dimethylaminoethyl, TFA salt) | (betulinic acid derivative with dimethyl cyclobutane dicarboxylate linker and 2-(pyrrolidin-2-yl)-4-(4-fluorophenyl)imidazole-N-ethyl-dimethylamine amide) | H¹ NMR (DMSO-D₆ + D₂O, 300 MHz): δ 12.05 (br peak, 1H), 7.67 (m, 2H), 7.46 (s, 1H), 7.11 (m, 2H), 5.10 (m, 1H), 4.49 (s, 1H), 4.42 (s, 1H), 4.35 (m, 1H), 4.15 (m, 2H), 3.84 (m, 1H), 3.67 (m, 1H), 2.70-2.95 (m, 4H), 2.10-2.60 (m, 5H), 2.23 (s, 6H), 0.70-2.0 (m, 50H); Mass (ESI): 895.70 [M + H]⁺; HPLC: 95.19%. |
| 8. | (structure of pyrrolidine-imidazole-4-pyridyl with dimethylaminoethyl, TFA salt) | (betulinic acid derivative with dimethyl cyclobutane dicarboxylate linker and 2-(pyrrolidin-2-yl)-4-(pyridin-4-yl)imidazole-N-ethyl-dimethylamine amide) | H¹ NMR (DMSO-D₆, 300 MHz): δ 12.15 (bs, 1H), 8.86 (s, 1H), 8.32 (d, J = 4.0 Hz, 1H), 7.93 (d, J = 8.6 Hz, 1H), 7.65 (s, 1H), 7.30 (dd, J = 8.6, 4.0 Hz, 1H), 5.11 (m, 1H), 4.48 (s, 1H), 4.42 (s, 1H), 4.32 (m, 1H), 4.21 (m, 2H), 3.86 (m, 1H), 3.67 (m, 1H), 3.07 (m, 1H), 2.7-2.95 (m, 3H), 2.29 (s, 6H), 2.10-2.60 (m, 5H), 0.70-2.0 (m, 50H); Mass (ESI): 878.74 [M + H]⁺; HPLC: 92.20%. |

-continued

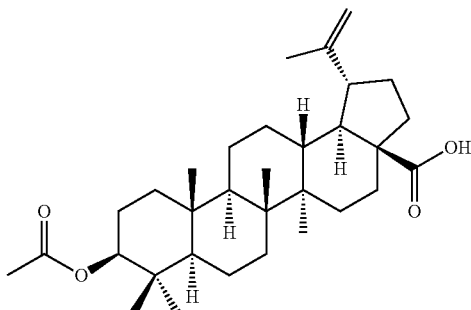
(Starting material)

| Example no | Intermediate no | Structure | Characterization data |
|---|---|---|---|
| 9. | (pyrrolidinyl-imidazole-pyridine intermediate) TFA | (betulinic acid derivative structure) | H$^1$ NMR (DMSO-D$_6$, 300 MHz): δ 12.15 (bs, 1H), 8.44 (d, J = 6.3 Hz, 2H), 7.80 (s, 1H), 7.57 (d, J = 6.3 Hz, 2H), 5.11 (m, 1H), 4.47 (s, 1H), 4.42 (s, 1H), 4.32 (m, 1H), 4.21 (m, 2H), 3.86 (m, 1H), 3.67 (m, 1H), 2.5-2.95 (m, 7H), 2.10-2.50 (m, 6H), 0.70-2.0 (m, 54H); Mass (ESI): 904.68 [M + H]$^+$; HPLC: 87.55%. |
| 10. | (pyrrolidinyl-imidazole-phenyl intermediate) TFA | (betulinic acid derivative structure) | H$^1$ NMR (DMSO-D$_6$, 300 MHz): δ 12.17 (bs, 1H), 7.65 (d, J = 8.3 Hz, 2H), 7.50 (s, 1H), 7.28 (t, J = 8.0 Hz, 2H), 7.11 (t, J = 8.0, 1H), 5.11 (m, 1H), 4.49 (s, 1H), 4.42 (s, 1H), 4.33 (m, 1H), 4.18 (m, 2H), 3.85 (m, 1H), 3.67 (m, 1H), 2.50-3.0 (m, 6H), 2.10-2.60 (m, 6H), 0.70-2.0 (m, 55H); Mass (ESI): 903.68 [M + H]$^+$; HPLC: 93.69%. |
| 11. | (pyrrolidinyl-imidazole-tBu intermediate) TFA | (betulinic acid derivative structure) | H$^1$ NMR (DMSO-D$_6$, 300 MHz): δ 12.05 (broad peak, 1H), 6.62 (s, 1H), 5.01 (m, 1H), 4.52 (s, 1H), 4.46 (s, 1H), 4.32 (m, 1H), 4.0 (m, 2H), 3.75 (m, 1H), 3.62 (m, 1H), 2.70-2.85 (m, 2H), 2.0-2.5 (m, 6H), 2.20 (s, 6H), 0.70-2.0 (m, 60H); Mass (ESI): 857.78 [M + H]$^+$; HPLC: 90.14%. |

-continued

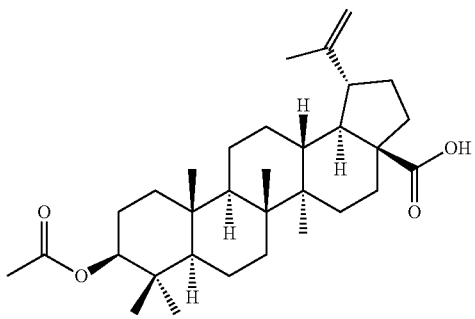

(Starting material)

| Example no | Intermediate no | Structure | Characterization data |
|---|---|---|---|
| 12. | (pyrrolidine-imidazole-3-fluorophenyl intermediate with N,N-dimethyl ethylamine, TFA salt) | (betulinic acid derivative with cyclobutane dicarboxylate ester at 3-position and pyrrolidinyl amide with 4-(3-fluorophenyl)imidazole at 28-position) | H$^1$ NMR (DMSO-D$_6$ + D$_2$O, 300 MHz): δ 11.77 (br peak, 1H), 7.59 (s, 1H), 7.45 (d, J = 8.7 Hz, 1H), 7.25-7.42 (m, 2H), 6.92 (t, J = 8.7 Hz, 1H), 5.11 (m, 1H), 4.49 (s, 1H), 4.42 (s, 1H), 4.32 (m, 1H), 4.13 (m, 2H), 3.85 (m, 1H), 3.67 (m, 1H), 2.6-2.90 (m, 4H), 2.22 (s, 6H), 2.0-2.4 (m, 4H), 0.70-2.0 (m, 51H); Mass (ESI): 895.63 [M + H]$^+$; HPLC: 92.37%. |
| 13. | (pyrrolidine-imidazole-isopropyl intermediate with N,N-dimethyl ethylamine, TFA salt) | (betulinic acid derivative with cyclobutane dicarboxylate ester and pyrrolidinyl amide with 4-isopropylimidazole) | H$^1$ NMR (DMSO-D$_6$, 300 MHz): δ 12.05 (broad peak, 1H), 6.62 (s, 1H), 5.01 (m, 1H), 4.52 (s, 1H), 4.46 (s, 1H), 4.32 (m, 1H), 4.0 (m, 2H), 3.75 (m, 1H), 3.62 (m, 1H), 2.70-2.85 (m, 3H), 2.0-2.5 (m, 6H), 2.20 (s, 6H), 0.70-2.0 (m, 57H); Mass (ESI): 843.72 [M + H]$^+$; HPLC: 91.31%. |
| 14 | (pyrrolidine-4,5-dimethylimidazole intermediate with N,N-dimethyl ethylamine, TFA salt) | (betulinic acid derivative with cyclobutane dicarboxylate ester and pyrrolidinyl amide with 4,5-dimethylimidazole) | H$^1$ NMR (DMSO-D$_6$, 300 MHz): δ 12.13 (bs, 1H), 4.97 (m, 1H), 4.56 (s, 1H), 4.48 (s, 1H), 4.33 (m, 2H), 4.08 (m, 1H), 3.74 (m, 1H), 3.66 (m, 1H), 2.70-2.75 (m, 4H), 2.0-2.35 (m, 20H), 0.70-2.0 (m, 47H); Mass (ESI): 829.61 [M + H]$^+$; HPLC: 98.54%. |

Example 15: Preparation of 2,2-dimethyl-4-oxo-4-(((1R,3aS,5aR,5bR,7aR,9S,11aR,11bR,13aR,13bR)-5a,5b,8,8,11a-pentamethyl-3a-((S)-2-(1-methyl-4-phenyl-1H-imidazol-2-yl) pyrrolidine-1-carbonyl)-1-(prop-1-en-2-yl)icosahydro-1H-cyclopenta[a]chrysen-9-yl)oxy)butanoic acid

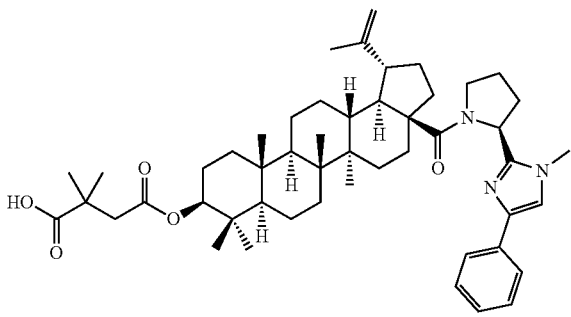

2,2-Dimethylsuccinic anhydride (385 mg, 3.0 mmol) was added to a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(1-methyl-4-phenyl-1H-imidazol-2-yl)pyrrolidin-1-yl)methanone (Example 1-step 2, 500 mg, 0.75 mmol) and DMAP (183 mg, 1.49 mmol) in pyridine (8 ml) at room temperature and heated at 90° C. for about 24 hours. After completion of the reaction (monitored by TLC), the reaction mixture was diluted with dichloromethane, washed with 20% HCl and brine solution. The residue was dried over $Na_2SO_4$, filtered, the solvent was evaporated under reduced pressure and purified on silica gel column (100-200 mesh, elution 36-40% ethyl acetate/hexanes) to afford the title compound (240 mg, Yield: 40%) as an off white solid. $H^1$ NMR (DMSO-$D_6$, 300 MHz): δ 12.15 (s, 1H), 7.64 (d, J=7.5 Hz, 2H), 7.42 (s, 1H), 7.27 (t, J=7.5 Hz, 2H), 7.11 (t, J=7.5, 1H), 5.11 (m, 1H), 4.50 (s, 1H), 4.43 (s, 1H), 4.35 (m, 1H), 3.85 (m, 1H), 3.68 (s, 3H), 3.65 (m, 1H), 2.75 (m, 1H), 2.10-2.60 (m, 6H), 0.70-2.0 (m, 48H); Mass (ESI): 794.55 $[M+H]^+$; HPLC: 92.60%.

The below examples were prepared by the procedure similar to the one described in the synthesis of example-15 with appropriate variations in reactants and quantities of reagents. The characterization data of the examples are summarized herein below table.

| Example no | Structure | Characterization data |
|---|---|---|
| 16. | 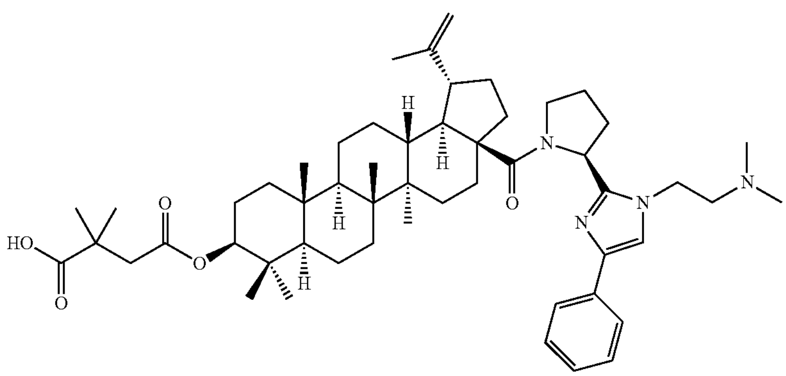 | $H^1$ NMR (DMSO-$D_6$, 300 MHz): δ 12.15 (bs, 1H), 7.65 (d, J = 7.5 Hz, 2H), 7.48 (s, 1H), 7.28 (t, J = 7.5 Hz, 2H), 7.11 (t, J = 7.5, 1H), 5.11 (m, 1H), 4.49 (s, 1H), 4.42 (s, 1H), 4.33 (m, 1H), 4.10 (m, 2H), 3.85 (m, 1H), 3.67 (m, 1H), 2.70-2.75 (m, 2H), 2.23 (s, 6H), 2.10-2.60 (m, 5H), 0.70-2.0 (m, 50H); Mass (ESI): 851.66 $[M + H]^+$; HPLC: 90.28 %. |
| 17. | 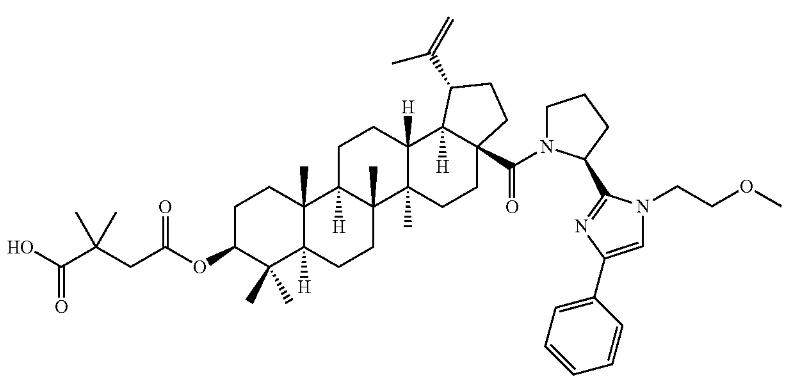 | $H^1$ NMR (DMSO-$D_6$, 300 MHz): δ 12.10 (bs, 1H), 7.65 (d, J = 7.5 Hz, 2H), 7.44 (s, 1H), 7.28 (t, J = 7.5 Hz, 2H), 7.11 (t, J = 7.5, 1H), 5.11 (m, 1H), 4.49 (s, 1H), 4.42 (s, 1H), 4.30 (m, 2H), 4.10 (m, 1H), 3.85 (m, 1H), 3.67 (m, 3H), 3.28 (s, 3H), 2.55-2.75 (m, 2H), 2.10-2.60 (m, 5H), 0.70-2.0 (m, 48H); Mass (ESI): 838.62 $[M + H]^+$; HPLC: 86.72%. |

| Example no | Structure | Characterization data |
|---|---|---|
| 18. | 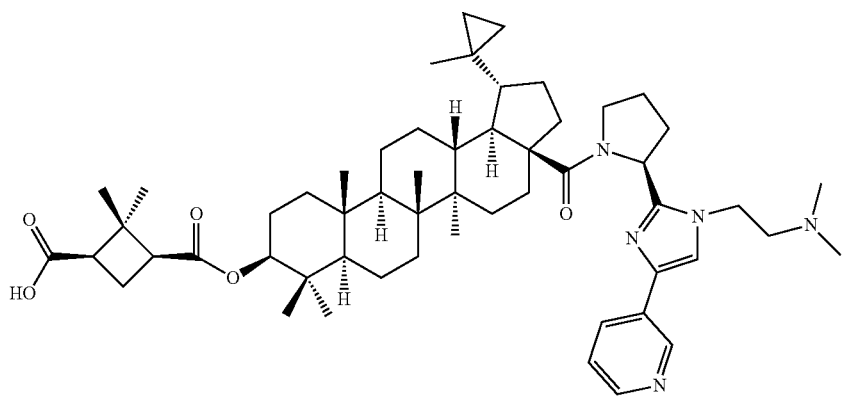 | H¹ NMR (DMSO-D$_6$, 300 MHz): δ 12.16 (bs, 1H), 8.90 (s, 1H), 8.38 (d, J = 4.0 Hz, 1H), 7.97 (d, J = 8.6 Hz, 1H), 7.84 (s, 1H), 7.36 (m, 1H), 5.95 (m, 1H), 4.65 (s, 1H), 4.52 (s, 1H), 4.38 (m, 1H), 2.90-4.30 (m, 4H), 2.7-2.95 (m, 2H), 2.29 (s, 6H), 2.11-2.60 (m, 3H), 0.70-2.0 (m, 54H); Mass (ESI): 852.65 [M + H]$^+$; HPLC: 96.34%. |

Example 19: Preparation of (1R,3S)-3-(((((1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl)oxy)carbonyl)-2,2-dimethylcyclobutane-1-carboxylic acid Step 1: Synthesis of (1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl acetate

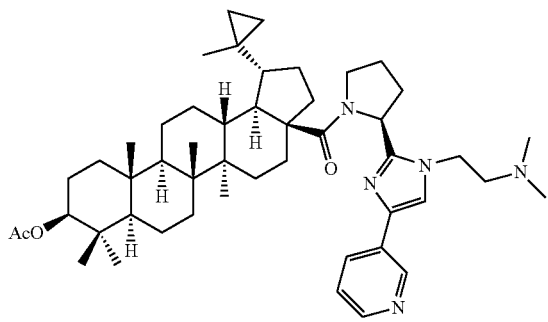

To a stirred solution of (1R,3aS,5aR,5bR,7aR,9S,11aR,11bR,13aR,13bR)-9-acetoxy-5a,5b,8,8,11a-pentamethyl-1-(1-methylcyclopropyl)icosahydro-1H-cyclopenta[a]chrysene-3a-carboxylic acid (prepared as described in WO 2013/160810 A2, 3.0 g, 5.88 mmol) in DCM (40 ml), Oxalyl chloride (2.4 ml, 29.4 mmol) was added at 0° C. and stirred at room temperature for about 3 hours. After completion of the reaction (monitored by TLC), the solvent was evaporated under nitrogen atmosphere and the residue was dissolved in DCM (10 ml) which was then added to a stirred solution of (S)—N,N-dimethyl-2-(4-(pyridin-3-yl)-2-(pyrrolidin-2-yl)-1H-imidazol-1-yl) ethanamine 2,2,2-trifluoroacetate (Intermediate 9, 2.34 g, 5.88 mmol) and triethyl amine (5.4 ml, 41.1 mmol) in DCM (30 ml) at 0° C. and continued to stir at room temperature for about 18 hours. After completion of the reaction (monitored by TLC), the reaction mixture was diluted with dichloromethane (200 ml), washed with water, brine and then dried over Na₂SO₄. The solvent was evaporated and purified on silica gel column (100-200 mesh, eluted with 6% methanol/dichloromethane) to afford the title compound (3.5 g, Yield: 76%) as an off white solid. H¹ NMR (DMSO-D₆, 300 MHz): δ 8.85 (s, 1H), 8.33 (d, J=4.0 Hz, 1H), 7.93 (d, J=8.7 Hz, 1H), 7.60 (s, 1H), 7.30 (dd, J=8.6, 4.0 Hz, 1H), 5.06 (m, 1H), 4.36 (m, 1H), 4.10 (m, 2H), 3.83 (m, 1H), 3.64 (m, 1H), 2.65 (m, 2H), 2.22 (s, 6H), 2.10-2.60 (m, 3H), 1.99 (s, 3H), 0.70-2.0 (m, 44H), 0.20 (m, 2H), 0.05 (m, 1H), −0.80 (m, 1H); Mass (ESI): 780.67 [M+H]⁺.

Step 2: Synthesis of a S)-2-(1-(2-(dimethylamino)ethyl)-4-(pyridin-3-yl)-1H-imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(1-methylcyclopropyl)icosahydro-3aH-cyclopenta[a]chrysen-3a-yl) methanone

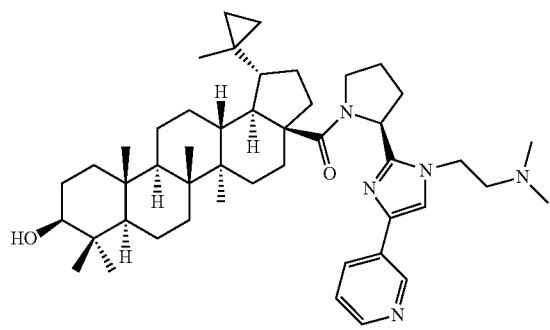

To a stirred solution of (1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl acetate (step 1, 3.5 g, 4.40 mmol) in MeOH:THF:H₂O (1:1:1, 45 ml) was added lithium hydroxide monohydrate (1.80 g, 44.9 mmol) and allowed to stir at room temperature for about 24 hours. After completion of the reaction (monitored by TLC), the solvents were evaporated, the product was extracted with ethyl acetate (2×100 ml), dried over Na₂SO₄ and filtered. The solvent was evaporated to afford the crude compound (780 mg, Yield: 24%), which was used in the next reaction without further purification. H¹ NMR (DMSO-D₆, 300 MHz): δ 8.86 (s, 1H), 8.32 (d, J=4.0 Hz, 1H), 7.93 (d, J=8.7 Hz, 1H), 7.60 (s, 1H), 7.30 (dd, J=8.6, 4.0 Hz, 1H), 5.06 (m, 1H), 4.28 (m, 1H), 4.10 (m, 2H), 3.83 (m, 1H), 3.64 (m, 1H), 2.97 (m, 1H), 2.65 (m, 2H), 2.22 (s, 6H), 2.10-2.60 (m, 3H), 0.70-2.0 (m, 44H), 0.20 (m, 2H), 0.05 (m, 1H), −0.80 (m, 1H); Mass (ESI): 738.62 [M+H]⁺.

Step 3: Synthesis of 1-benzyl 3-((1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl)(1R,3S)-2,2-dimethylcyclobutane-1,3-dicarboxylate

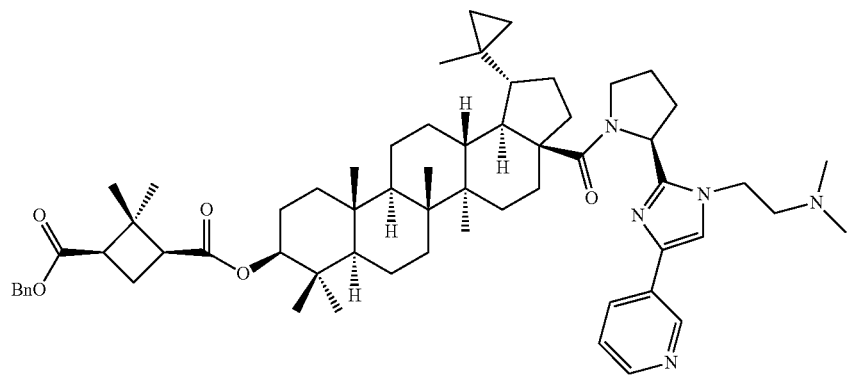

To a stirred solution of (1S,3R)-3-(benzyloxycarbonyl)-2,2-dimethylcyclobutane carboxylic acid (prepared as described in WO 2013/160810 A2, 550 mg, 2.09 mmol) in THF (30 ml) at 0° C. was added DIPEA (809 mg, 6.2 mmol) followed 2,4,6-trichlorobenzoyl chloride (558 mg, 2.3 mmol). The mixture was stirred at ambient temperature for about 4 hours and concentrated under reduced pressure. The obtained mixed anhydride was dissolved in toluene (30 ml), then added to a stirred solution of ((S)-2-(1-(2-(dimethylamino)ethyl)-4-(pyridin-3-yl)-1H-imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(1-methylcyclopropyl)icosahydro-3aH-cyclopenta[a]chrysen-3a-yl)methanone (step 2, 770 mg, 1.04 mmol) and DMAP (510 mg, 4.1 mmol) in toluene (20 ml) at room temperature and heated at 90° C. for about 18 hours. After completion of the reaction (monitored by TLC), the reaction mixture was diluted with ethyl acetate (2×100 ml), washed with water followed by brine solution. The organic layer was dried over Na$_2$SO$_4$, filtered, the solvent was evaporated under reduced pressure and purified on silica gel column (100-200 mesh, eluted with 3% methanol/dichloromethane) to afford the title compound (800 mg, Yield: 78%) as an off white solid. H$^1$ NMR (DMSO-D$_6$, 300 MHz): δ 8.86 (s, 1H), 8.32 (d, J=4.0 Hz, 1H), 7.93 (d, J=8.7 Hz, 1H), 7.60 (s, 1H), 7.36 (m, 6H), 5.12 (m, 3H), 4.36 (m, 1H), 4.10 (m, 2H), 3.83 (m, 1H), 3.64 (m, 1H), 2.60-2.96 (m, 5H), 2.22 (s, 6H), 2.10-2.60 (m, 4H), 0.70-2.0 (m, 50H), 0.20 (m, 2H), 0.05 (m, 1H), −0.80 (m, 1H); Mass (ESI): 982.70 [M+H]$^+$.

Step 4: Synthesis of (1R,3S)-3-((((1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl) oxy)carbonyl)-2,2-dimethylcyclobutane-1-carboxylic acid To a stirred solution of 1-benzyl 3-((1R,3aS,5aR,5bR,7aR,9S,11aR,11bR,13aR,13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl) (1R,3S)-2,2-dimethylcyclobutane-1,3-dicarboxylate (step 3, 800 mg, 0.81 mmol) and ammonium formate (256 mg, 4.0 mmol) in MeOH: EtOAc (1:1, 30 ml) was added 10% Pd/C (150 mg) and stirred at ambient temperature for about 3 hours. After completion of the reaction (monitored by TLC), the catalyst was filtered through Celite bed and the filtrate was evaporated to dryness. The residue was purified by silica gel column chromatography using 4% methanol/dichloromethane as an eluent to afford the title compound (350 mg, Yield: 48%). H$^1$ NMR (DMSO-D$_6$, 300 MHz): δ 12.12 (br peak, 1H), 8.86 (s, 1H), 8.32 (d, J=4.0 Hz, 1H), 7.93 (d, J=8.7 Hz, 1H), 7.60 (s, 1H), 7.30 (dd, J=8.6, 4.0 Hz, 1H), 5.06 (m, 1H), 4.35 (m, 1H), 4.10 (m, 2H), 3.83 (m, 1H), 3.64 (m, 1H), 2.60-2.96 (m, 5H), 2.22 (s, 6H), 2.10-2.60 (m, 4H), 0.70-2.0 (m, 50H), 0.20 (m, 2H), 0.05 (m, 1H), −0.80 (m, 1H); Mass (ESI): 892.70 [M+H]$^+$; HPLC: 91.02%.

The below examples were prepared by the procedure similar to the one described in the synthesis of example-19 with appropriate variations in reactants and quantities of reagents. The characterization data of the examples are summarized herein below table.

| Example no | Structure | Characterization data |
|---|---|---|
| 20. | 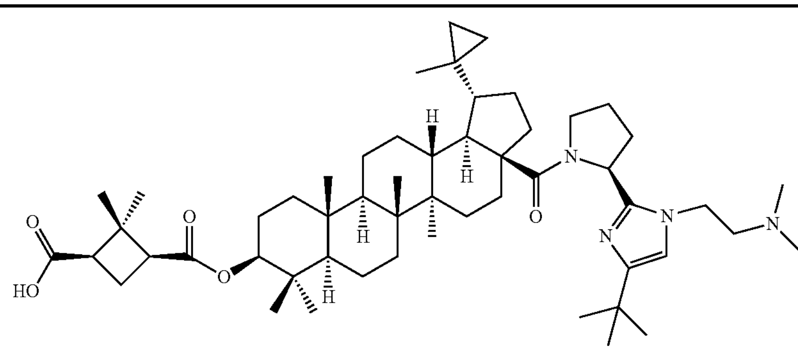 | H$^1$ NMR (DMSO-D$_6$, 300 MHz): δ 12.13 (broad peak, 1H), 6.60 (s, 1H), 4.97 (m, 1H), 4.32 (m, 1H), 3.95 (m, 2H), 3.73 (m, 1H), 3.60 (m, 1H), 2.70-2.85 (m, 2H), 2.0-2.5 (m, 6H), 2.20 (s, 6H), 0.70-2.0 (m, 60H), 0.1-0.3 (m, 3H), −0.09 (m, 1H); Mass (ESI): 871.69 [M +H]$^+$; HPLC: 90.16%. |
| 21. | 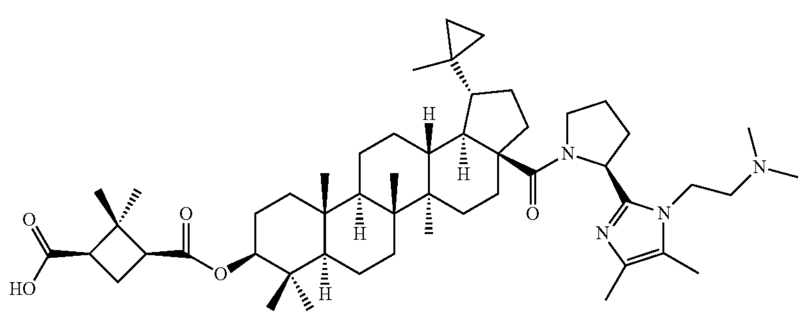 | H$^1$ NMR (CDCl$_3$, 300 MHz): δ 4.95 (m, 1H), 4.46 (m, 1H), 4.22 (m, 1H), 3.95 (m, 2H), 3.73 (m, 1H), 2.90-3.20 (m, 3H), 2.78 (m, 4H), 2.56 (m, 2H), 2.34 (s, 6H), 2.09 (s, 6H), 1.80-2.25 (m, 5H), 0.70-1.80 (m, 45H), 0.34 (m, 1H), 0.24 (m, 1H), 0.12 (m, 2H); Mass (ESI): 843.62 [M + H]$^+$; HPLC: 94.39%. |

Example 22: Preparation of (1R,3S)-3-((((1R,3aS,5aR,5bR,7aR,9S,11aR,11bR,13aR,13bR)-3a-((S)-2-(1-(2-(diethoxyphosphoryl)ethyl)-4-phenyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethylcyclobutane-1-carboxylic acid

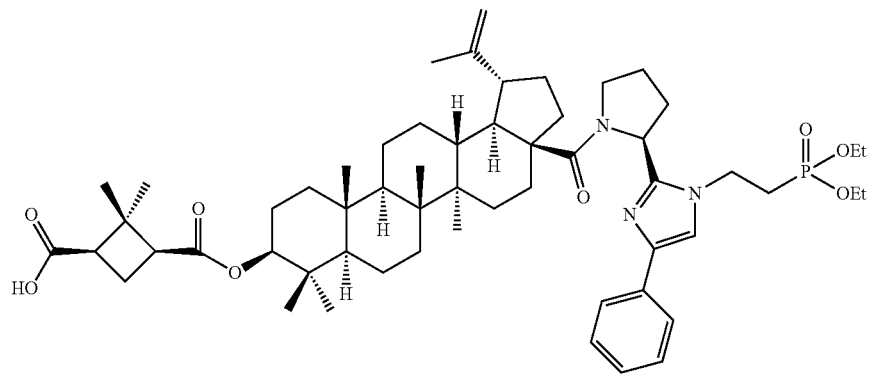

Step 1: Synthesis of (S)-5-phenyl-2-(pyrrolidin-2-yl)-1H-imidazole TFA salt

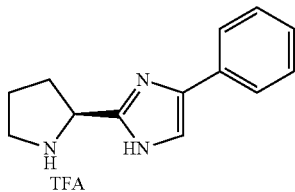 [SMILES: c1ccc(-c2c[nH]c([C@@H]3CCCN3)n2)cc1]

A solution of (S)-tert-butyl 2-(4-phenyl-1H-imidazol-2-yl)pyrrolidine-1-carboxylate (Intermediate 1-step 2, 2.0 g, 6.6 mmol) in TFA:DCM (1:2, 15 mL) was stirred at 0° C.-room temperature for about 1 hour. After completion of the reaction (monitored by TLC), the solvent was evaporated and the crude product was used in the next step without further purification (2.1 g).

Step 2: Synthesis of (1R,3aS,5aR,5bR,7aR,9S,11aR,11bR,13aR,13bR)-5a,5b,8,8,11a-penta methyl-3a-((S)-2-(4-phenyl-1H-imidazol-2-yl)pyrrolidine-1-carbonyl)-1-(prop-1-en-2-yl) icosahydro-1H-cyclopenta[a]chrysen-9-yl acetate To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in WO 2013/160810 A2, 3.0 g, 6.02 mmol) in DCM (30 mL), Oxalyl chloride (3 mL, 23.6 mmol) in DCM (5 mL) was added at 0° C. and stirred at room temperature for about 3 hours. After completion of the reaction (monitored by TLC), the solvent was evaporated under nitrogen atmosphere and dissolved in DCM (4 mL) which was then added to the above stirred solution of (S)-4-phenyl-2-(pyrrolidin-2-yl)-1H-imidazole TFA salt (step 1, 2.01 g, 6.42 mmol) and Triethylamine (1.94 g, 19.26 mmol) at 0° C. and allowed to stir at room temperature for about 16 hours. After completion of the reaction (monitored by TLC), the reaction mixture was diluted with dichloromethane, washed with water, 1N HCl, brine and dried over $Na_2SO_4$. The solvent was evaporated and purified by silica gel column (100-200 mesh, eluted in 30% ethyl acetate/hexane) to afford the title compound (3.0 g, yield: 71%) as an off white solid. $^1$H NMR (300 MHz, $CDCl_3$): δ 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 693 [M+1]$^+$ 694 (100%).

Step 3: Synthesis of a 1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(4-phenyl-1H-imidazol-2-yl)pyrrolidin-1-yl)methanone

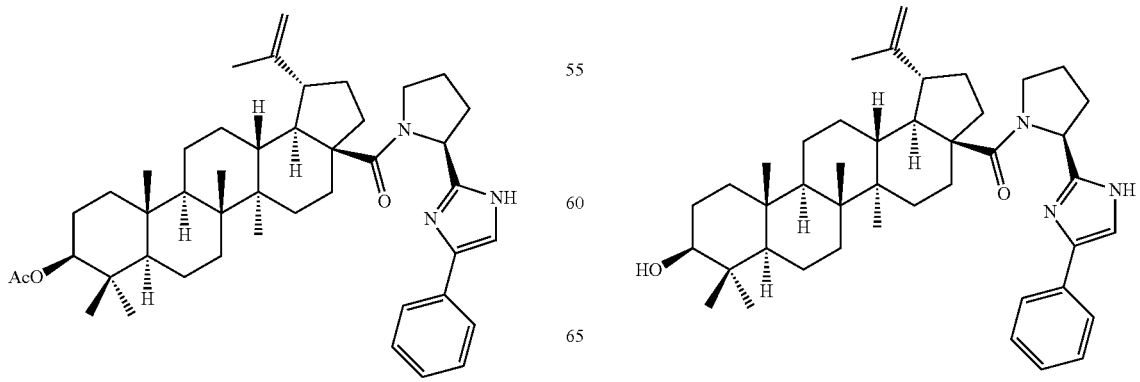

To a stirred solution of (1R,3aS,5aR,5bR,7aR,9S,11aR, 11bR,13aR,13bR)-5a,5b,8,8,11a-pentamethyl-3a-((S)-2-(4-phenyl-1H-imidazol-2-yl)pyrrolidine-1-carbonyl)-1-(prop-1-en-2-yl) icosahydro-1H-cyclopenta[a]chrysen-9-yl acetate (step 2, 2.4 g, 3.46 mmol) in MeOH (50 mL) was added potassium carbonate (3.3 g, 24.2 mmol) at 0° C. and allowed to stir at room temperature for about 16 hours. After completion of the reaction (monitored by TLC), the volatile was evaporated, the aqueous layer was extracted with ethyl acetate, the organic layer was washed with water, brine and dried over $Na_2SO_4$. Then the solvent was evaporated and the resulting crude was purified by silica gel column (100-200 mesh, eluted with 15% ethyl acetate/hexane) to afford the title compound (1.8 g, yield: 80%) as an off white solid. $^1$H NMR (300 MHz, $CDCl_3$): δ 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 651 $[M+1]^+$ 652 (100%).

Step 4: Synthesis of 1-benzyl 3-((1R,3aS,5aR,5bR, 7aR,9S,11aR,11bR,13aR,13bR)-5a,5b,8,8,11a-pentamethyl-3a-((S)-2-(4-phenyl-1H-imidazol-2-yl) pyrrolidine-1-carbonyl)-1-(prop-1-en-2-yl) icosahydro-1H-cyclopenta[a]chrysen-9-yl) (1R,3S)-2,2-dimethylcyclobutane-1,3-dicarboxylate

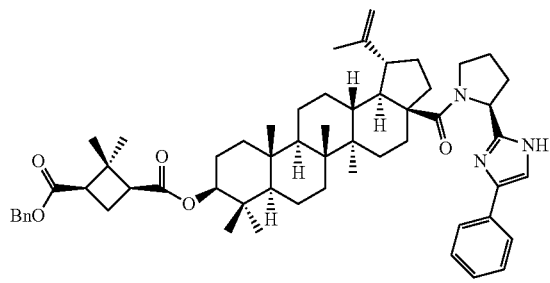

To a stirred solution of ((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysen-3a-yl)((S)-2-(4-phenyl-1H-imidazol-2-yl)pyrrolidin-1-yl) methanone (step 3, 1.4 g, 2.24 mmol, 1.0 eq) in pyridine (50 mL) was added DMAP (0.54 g, 4.42 mmol, 2.0 eq) and (1S,3R)-3-(benz yloxycarbonyl)-2,2-dimethylcyclobutanecarboxylic 2,4,6-trichlorobenzoic anhydride (prepared as described in WO 2013/160810 A2, 1.6 g, 3.2 mmol). The reaction mixture was heated to 90° C. for overnight. TLC indicated starting material was consumed and the desired product was observed. The reaction mixture was evaporated under reduced pressure and diluted with water. The aqueous layer was extracted with dichloromethane (2×50 mL). The combined organic layers were dried over $Na_2SO_4$, filtered and evaporated under reduced pressure. The crude residue was purified by silica gel column chromatography by using 1.5% methanol/dichloromethane as an eluent to obtain the title compound (1.3 g) as a white solid. $^1$H NMR (300 MHz, $CDCl_3$): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35

(m, 1H), 7.01-7.11 (m, 3H), 7.12-7.13 (m, 2H), 7.22-7.60 (m, 3H), 7.70-7.88 (m, 2H), 10.50 (s, 1H); Mass: 895 $[M+1]^+$ 896 (100%).

Step 5: Synthesis of (1R,3S)-2,2-dimethyl-3-(((((1R, 3aS,5aR,5bR,7aR,9S,11aR,11bR,13aR,13bR)-5a,5b, 8,8,11a-pentamethyl-3a-((S)-2-(4-phenyl-1H-imidazol-2-yl)pyrrolidine-1-carbonyl)-1-(prop-1-en-2-yl) icosahydro-1H-cyclopenta[a]chrysen-9-yl)oxy) carbonyl) cyclobutane-1-carboxylic acid

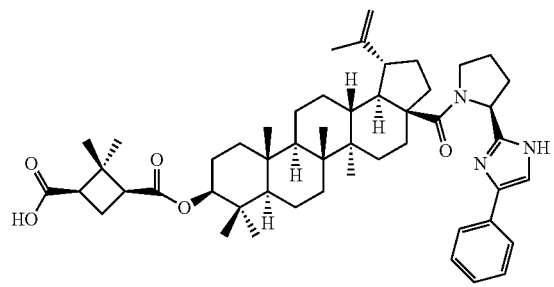

To a solution of 1-benzyl 3-((1R,3aS,5aR,5bR,7aR,9S, 11aR,11bR,13aR,13bR)-5a,5b,8,8,11a-pentamethyl-3a-((S)-2-(4-phenyl-1H-imidazol-2-yl)pyrrolidine-1-carbonyl)-1-(prop-1-en-2-yl)icosahydro-1H-cyclopenta[a] chrysen-9-yl)(1R,3S)-2,2-dimethylcyclobutane-1,3-dicarboxylate (step 4, 1.3 g, 1.45 mmol, 1.0 eq) in dichloromethane (30 mL) was added palladium (II) acetate (30 mg), Triethyl amine (0.29 g, 2.87 mmol, 3.0 eq) and triethylsilane (0.56 g, 4.87 mmol, 3.0 eq). The mixture was flushed with $N_2$ and was heated to reflux for about 48 hours. TLC indicated starting material was consumed and the desired product was observed, the reaction mixture was cooled to room temperature, filtered through a pad of celite and was washed with dichloromethane (50 mL). The filtrate was evaporated under reduced pressure, cooled to 0° C., diluted with water (10 mL), acidified to pH 5.0 with 1N HCl and extracted with $CH_2Cl_2$ (2×200 mL). The combined organic layers were dried over $Na_2SO_4$, filtered and evaporated under reduced pressure. The crude residue was purified by silica gel column chromatography by using 6% methanol/dichloromethane as an eluent to afford the title compound (0.55 g) as a white solid. $^1$H NMR (300 MHz, $CDCl_3$): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.60 (m, 3H), 7.70-7.88 (m, 2H), 10.50 (s, 1H); Mass: 805 $[M+1]^+$ 806 (100%); HPLC Purity: 92.6%.

Step 6: Synthesis of (1R,3S)-3-(((((1R,3aS,5aR,5bR, 7aR,9S,11aR,11bR,13aR,13bR)-3a-((S)-2-(1-(2-(diethoxyphosphoryl)ethyl)-4-phenyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethylcyclobutane-1-carboxylic acid To a stirred solution of (1R,3S)-2,2-dimethyl-3-(((((1R, 3aS,5aR,5bR,7aR,9S,11aR,11bR,13aR,13bR)-5a,5b,8,8, 11a-pentamethyl-3a-((S)-2-(4-phenyl-1H-imidazol-2-yl) pyrrolidine-1-carbonyl)-1-(prop-1-en-2-yl)icosahydro-1H- cyclopenta[a]chrysen-9-yl)oxy) carbonyl)cyclo butane-1-carboxylic acid (step 5, 600 mg, 0.74 mmol), $Cs_2CO_3$ (1.46 g, 4.45 mmol) in DMF (10 ml) at 0° C. was added diethyl vinylphosphonate (183 mg, 1.11 mmol) and stirred for about 2 days at room temperature. After completion of the reaction (monitored by TLC), the reaction mixture was poured onto ice water (100 ml) and washed with diethyl ether (2×75 ml). Aqueous phase pH was adjusted to 5 with 1N HCl, extracted with ethyl acetate (2×75 ml), dried over $Na_2SO_4$ and concentrated in vacuo. The residue was triturated with diethyl ether (50 ml), filtered and dried to afford the title compound (450 mg, yield: 62%). $H^1$ NMR (DMSO-$D_6$, 300 MHz): δ 12.14 (bs, 1H), 7.65 (d, J=7.5 Hz, 2H), 7.52 (s, 1H), 7.29 (t, J=7.5 Hz, 2H), 7.11 (t, J=7.5, 1H), 5.11 (m, 1H), 4.48 (s, 1H), 4.42 (s, 1H), 4.33 (m, 1H), 4.25 (m, 2H), 4.05 (m, 4H), 3.85 (m, 1H), 3.67 (m, 1H), 2.70-2.75 (m, 3H), 2.10-2.60 (m, 6H), 0.70-2.0 (m, 56H); Mass (ESI): 970.53 $[M+H]^+$; HPLC: 91.41%.

Example 23: Preparation of (1R,3S)-2,2-dimethyl-3-((((1R,3aS,5aR,5bR,7aR,9S,11aR,11bR,13aR,13bR)-5a,5b,8,8,11a-pentamethyl-3a-((S)-2-(4-phenyl-1-(2-phosphonoethyl)-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid icosahydro-1H-cyclopenta[a]chrysen-9-yl)oxy)carbonyl)-2,2-dimethylcyclobutane-1-carboxylic acid (Example 22-step 6, 140 mg, 0.144 mmol) in dichloromethane (5 mL) at 0° C. was added trimethylsilyl bromide (442 mg, 2.88 mmol) and the resulting mixture was stirred for about 2 days at room temperature. After completion of the reaction (monitored by TLC), the reaction was quenched with water and extracted with dichloromethane (2×50 ml). The organic layer was washed with brine (50 ml), dried over $Na_2SO_4$ and concentrated in vacuo. The residue was triturated with methanol: ethyl acetate (30 ml, 1:9), filtered and dried to afford the title compound (60 mg, Yield: 45%). $H^1$ NMR (DMSO-$D_6$, 300 MHz): δ 7.67 (m, 3H), 7.29 (m, 2H), 7.15 (s, 1H), 5.92 and 5.76 (2 bs, 2H), 4.48 (s, 1H), 4.42 (s, 1H), 4.33 (m, 2H), 4.18 (m, 2H), 3.7-3.91 (m, 2H), 2.70-2.75 (m, 3H), 2.10-2.60 (m, 6H), 0.70-2.0 (m, 50H); Mass (ESI): 914.60 $[M+H]^+$; HPLC: 90.04%.

Example 24: Preparation of (1R,3S)-3-((((1R,3aS,5aR,5bR,7aR,9S,11aR,11bR,13aR,13bR)-3a-((S)-2-(1-(2-(diethoxyphosphoryl)ethyl)-4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid

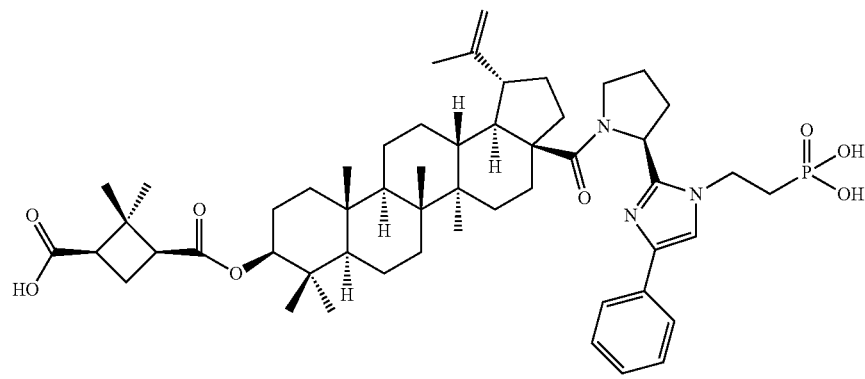

To a solution of (1R,3S)-3-((((1R,3aS,5aR,5bR,7aR,9S,11aR,11bR,13aR,13bR)-3a-((S)-2-(1-(2-(diethoxyphosphoryl)ethyl)-4-phenyl-1H-imidazol-2-yl)pyrrolidine-1-carbonyl)-5a,5b,8,8,11a-pentamethyl-1-(prop-1-en-2-yl)

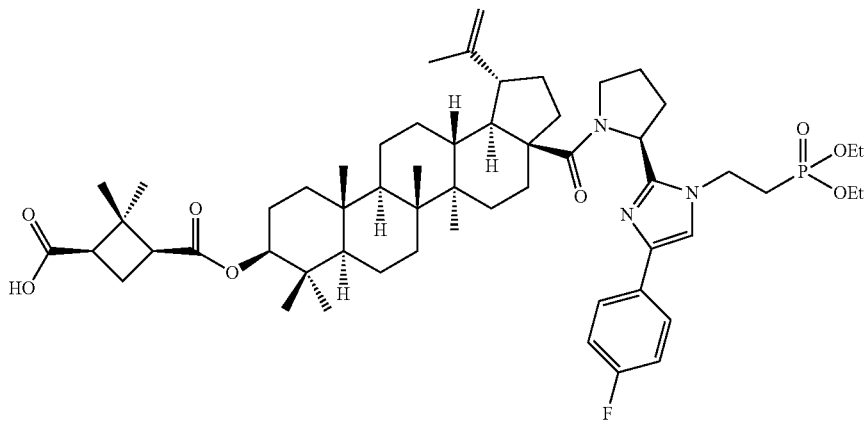

Step 1: Synthesis of (S)-1-tert-butyl 2-(2-(4-fluorophenyl)-2-oxoethyl)pyrrolidine-1,2-dicarboxylate

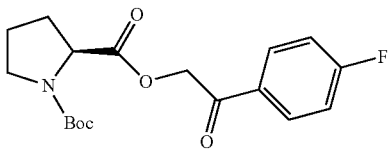 [SMILES: CC(C)(C)OC(=O)N1CCC[C@H]1C(=O)OCC(=O)c1ccc(F)cc1]

To a stirred solution of (S)-1-(tert-butoxycarbonyl)pyrrolidine-2-carboxylic acid (5.0 g, 23.2 mmol) in DCM (50 ml) at 0° C. was added DIPEA (8.0 ml, 46.51 mmol). After 10 minutes 2-bromo-1-(4-fluorophenyl)ethanone (5.0 g, 23.2 mmol) was added and the reaction mixture was allowed to stir at room temperature for about 18 hours. After completion of the reaction (monitored by TLC), the reaction mixture was diluted with dichloromethane (200 ml) and washed with water (200 ml), saturated brine (100 ml) and the organic layer was concentrated under reduced pressure to afford the title compound (6.0 g, Yield: 74%). The crude product was used in the next step without further purification. H$^1$ NMR (CDCl$_3$, 300 MHz): δ 7.96 (m, 1H), 7.48 (m, 1H), 7.16 (t, J=9.7 Hz, 1H), 7.06 (t, J=9.7 Hz, 1H), 5.35 (ABq, 2H), 4.45 (m, 1H), 3.35-3.70 (m, 2H), 2.32 (m, 2H), 1.85-2.10 (m, 2H), 1.45 (s, 9H).

Step 2: Synthesis of (S)-tert-butyl 2-(4-(4-fluorophenyl)-1H-imidazol-2-yl)pyrrolidine-1-carboxylate

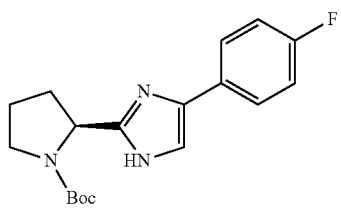 [SMILES: CC(C)(C)OC(=O)N1CCC[C@H]1c1nc(-c2ccc(F)cc2)c[nH]1]

To a stirred solution of (S)-1-tert-butyl 2-(2-(4-fluorophenyl)-2-oxoethyl)pyrrolidine-1,2-dicarboxylate (step 1, 6.0 g, 17.09 mmol) in toluene (60 ml), ammonium acetate (11.84 g, 153.81 mmol) was added at room temperature and refluxed for about 20 hours. After completion of the reaction (monitored by TLC), the reaction mixture was diluted with ethyl acetate (300 ml) and the organic layer was washed with 1 N HCl (2×100 ml). Aqueous layer was basified with 2N NaOH (200 ml), product was extracted with ethyl acetate (2×250 ml), washed with brine, dried over Na$_2$SO$_4$, filtered and concentrated to afford the title compound (2.20 g, yield: 39%) as an off white solid. H$^1$ NMR (CDCl$_3$, 300 MHz): δ 7.63 (m, 2H), 7.14 (s, 1H), 7.04 (t, J=9.7 Hz, 1H), 4.96 (m, 1H), 3.41 (m, 2H), 1.90-2.20 (m, 4H), 1.49 (s, 9H).

Step 3: Synthesis of (S)-5-(4-fluorophenyl)-2-(pyrrolidin-2-yl)-1H-imidazole TFA salt

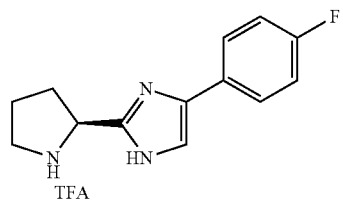 [SMILES: Fc1ccc(-c2c[nH]c([C@@H]3CCCN3)n2)cc1]

A solution of (S)-tert-butyl 2-(4-(4-fluorophenyl)-1H-imidazol-2-yl)pyrrolidine-1-carboxylate (step 2, 2.1 g, 6.4 mmol) in TFA:DCM (1:2, 30 mL) stirred at 0° C.-room temperature for about 1 hour. After completion of the reaction (monitored by TLC), the solvent was evaporated and the crude product was used in the next step without further purification (2.3 g).

Step 4: Synthesis of (1R,3aS,5aR,5bR,7aR,9S,11aR,11bR,13aR,13bR)-3a-((S)-2-(4-(4-fluoro phenyl)-1H-imidazol-2-yl)pyrrolidine-1-carbonyl)-5a,5b,8,8,11a-pentamethyl-1-(prop-1-en-2-yl) icosahydro-1H-cyclopenta[a]chrysen-9-yl acetate

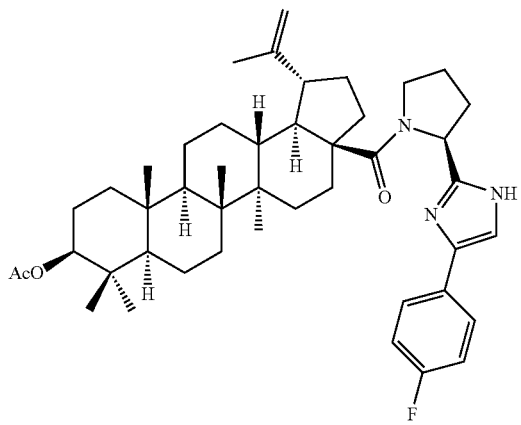

To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in WO 2013/160810 A2, 3.3 g, 6.62 mmol) in DCM (30 mL), Oxalyl chloride (2.4 mL, 18.9 mmol) in DCM (50 mL) was added at 0° C. and stirred at room temperature for about 3 hours. After completion of the reaction (monitored by TLC), the solvent was evaporated under nitrogen atmosphere and dissolved in dichloromethane (50 mL), which was then added to the above stirred solution of (S)-tert-butyl 2-(4-(4-fluorophenyl)-1H-imidazol-2-yl)pyrrolidine-1-carboxylate TFA salt (step 3, 2.3 g, 6.66 mmol) and triethylamine (2.01 g, 20.0 mmol) at 0° C. and allowed to stir at room temperature for about 16 hours. After completion of the reaction (monitored by TLC), the reaction mixture was diluted with dichloromethane, washed with water, 1N HCl, brine solution and dried over Na$_2$SO$_4$. The solvent was evaporated and purified by silica gel column (100-200 mesh, eluted 30% ethyl acetate in hexane) to afford the title compound (2.5 g, yield: 53%) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (s, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 711[M+1]$^+$ 712 (100%).

Step 5: Synthesis of ((S)-2-(4-(4-fluorophenyl)-1H-imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(prop-1-en-2-yl) icosahydro-3aH-cyclopenta[a]chrysen-3a-yl)methanone

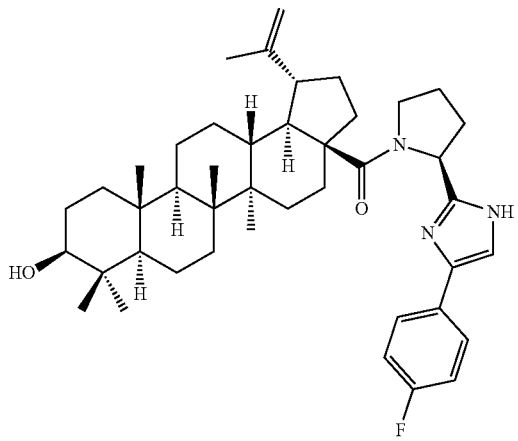

To a stirred solution of (1R,3aS,5aR,5bR,7aR,9S,11aR,11bR,13aR,13bR)-3a-((S)-2-(4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl acetate (step 4, 2.2 g, 3.3 mmol) in MeOH (30 mL) was added potassium carbonate (2.9 g, 21.65 mmol) at 0° C. and allowed to stir at room temperature for about 16 hours. After completion of the reaction (monitored by TLC), the volatile was evaporated and diluted with water, the aqueous layer was extracted with ethyl acetate. The organic layer was washed with water, brine and dried over $Na_2SO_4$, then the solvent was evaporated and the resulting crude was purified by silica gel column (100-200 mesh, eluted in 5% methanol/dichloromethane) to afford the title compound (1.8 g, yield: 87%) as an off white solid. $^1$H NMR (300 MHz, $CDCl_3$): δ 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 669 [M+1]$^+$ 670 (100%).

Step 6: Synthesis of 1-benzyl 3-((1R,3aS,5aR,5bR,7aR,9S,11aR,11bR,13aR,13bR)-3a-((S)-2-(4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate

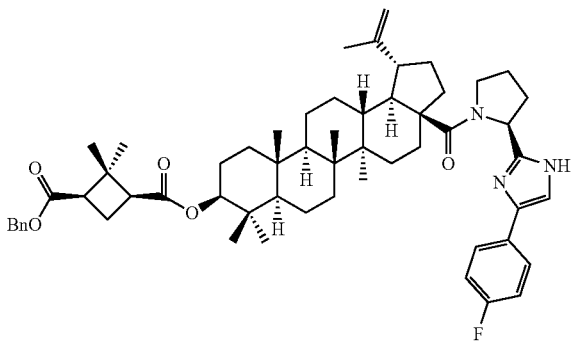

To a stirred solution of ((S)-2-(4-(4-fluorophenyl)-1H-imidazol-2-yl)pyrrolidin-1-yl) ((1R,3aS,5aR,5bR,7aR,9S,11aR,11bR,13aR,13bR)-9-hydroxy-5a,5b,8,8,11a-pentamethyl-1-(prop-1-en-2-yl) icosahydro-3aH-cyclopenta[a]chrysen-3a-yl)methanone (step 5, 6.5 g, 9.68 mmol, 1.0 eq) in pyridine (100 ml) was added DMAP (3.5 g, 28.68 mmol, 2.0 eq) and (1S,3R)-3-(benzyloxycarbonyl)-2,2-dimethylcyclobutanecarboxylic 2,4,6-trichlorobenzoic anhydride (prepared as described in WO 2013/160810 A2, 6.6 g, 13.2 mmol). The reaction mixture was heated to 90° C. for overnight. TLC indicated starting material was consumed and the desired product was observed. The reaction mixture was evaporated under reduced pressure and diluted with water. The aqueous layer was extracted with dichloromethane (2×500 ml). The combined organic layers were dried over $Na_2SO_4$, filtered and evaporated under reduced pressure. The crude residue was purified by silica gel column chromatography by using 1.5% methanol: dichloromethane as an eluent to obtain the title compound (4.5 g, yield: 50%) as a white solid. $^1$H NMR (300 MHz, $CDCl_3$): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.60 (m, 3H), 7.8-8.1 (s, 1H), 10.50 (s, 1H); Mass: 913 [M+1]$^+$ 914 (100%).

Step 7: Synthesis of (1R,3S)-3-((((1R,3aS,5aR,5bR,7aR,9S,11aR,11bR,13aR,13bR)-3a-((S)-2-(4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethyl cyclobutane-1-carboxylic acid

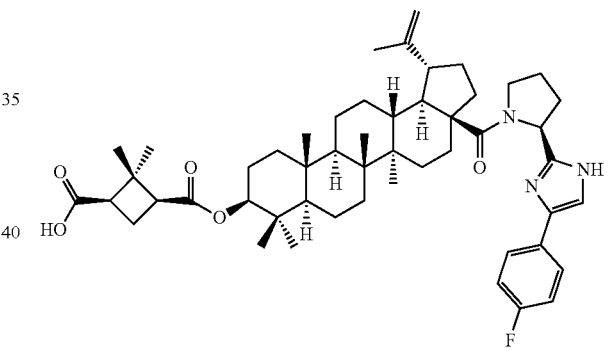

To a solution of 1-benzyl 3-((1R,3aS,5aR,5bR,7aR,9S,11aR,11bR,13aR,13bR)-3a-((S)-2-(4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl) (1R,3S)-2,2-dimethyl cyclobutane-1,3-dicarboxylate (step 6, 4.5 g, 4.9 mmol, 1.0 eq) dissolved in EtOAc: MeOH (1:1), added 2 g of Pd/C (wet 10%) under $N_2$ atmosphere and was added (1.5 g, 24.61 mmol) of ammonium formate at room temperature and stirred for about 2 hours. TLC indicated starting material was consumed and the desired product was observed. The reaction mixture was filtered through a pad of Celite and was washed with hot EtOAc: MeOH (1:1, 50 mL). The filtrate was evaporated under reduced pressure, diluted with water (10 ml), extracted with dichloromethane (2×200 ml) and brine wash. The combined organic layers were dried over $Na_2SO_4$, filtered and evaporated under reduced pressure. The crude residue was purified by silica gel column chromatography by using 6% methanol: dichloromethane as an eluent to afford the title compound (1.8 g, Yield: 44%) as a white solid. $^1$H NMR (300 MHz, DMSO-d6): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.70 (m, 3H), 10.50 (s, 1H); Mass: 823 [M+1]+ 824 (100%); HPLC Purity: 96%.

Step 8: Synthesis of (1R,3S)-3-((((1R,3aS,5aR,5bR,7aR,9S,11aR,11bR,13aR,13bR)-3a-((S)-2-(1-(2-(diethoxyphosphoryl)ethyl)-4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid To a stirred solution of (1R,3S)-3-((((1R,3aS,5aR,5bR,7aR,9S,11aR,11bR,13aR,13bR)-3a-((S)-2-(4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (step 7, 300 mg, 0.36 mmol) and Cs$_2$CO$_3$ (716 mg, 2.18 mmol) in DMF (10 ml) at 0° C. was added diethyl vinylphosphonate (89 mg, 0.54 mmol) and stirred for about 2 days at room temperature. TLC indicated starting material was consumed and the desired product was observed. The reaction mixture was poured onto ice water (100 ml) and washed with diethyl ether (2×75 ml). Aqueous phase pH was adjusted to 5 with 1N HCl and extracted with ethyl acetate (2×75 ml), dried over Na$_2$SO$_4$ and concentrated in vacuo. The residue was purified by column chromatography using ethyl acetate in hexanes to afford the title compound (190 mg). The compound was further purified by Prep TLC to get the pure compound (60 mg, Yield: 17%). H$^1$ NMR (DMSO-D$_6$, 300 MHz): δ 12.10 (bs, 1H), 7.65 (dd, J=6.3, 9.3 Hz, 2H), 7.50 (s, 1H), 7.29 (t, J=9.3 Hz, 2H), 5.05 (m, 1H), 4.48 (s, 1H), 4.42 (s, 1H), 4.33 (m, 1H), 4.25 (m, 2H), 4.05 (m, 4H), 3.85 (m, 1H), 3.67 (m, 1H), 2.70-2.75 (m, 3H), 2.10-2.60 (m, 6H), 0.70-2.0 (m, 56H); Mass (ESI): 988.62.53 [M+H]+; HPLC: 96.54%.

Example 25: Preparation of (1R,3S)-3-((((1R,3aS,5aR,5bR,7aR,9S,11aR,11bR,13aR,13bR)-3a-((2S,4R)-2-(1-(2-(dimethylamino)ethyl)-4-phenyl-1H-imidazol-2-yl)-4-(2-methoxy ethoxy)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid Step 1: Synthesis of (1R,3aS,5aR,5bR,7aR,9S,11aR,11bR,13aR,13bR)-3a-((2S,4R)-4-(2-methoxyethoxy)-2-(4-phenyl-1H-imidazol-2-yl)pyrrolidine-1-carbonyl)-5a,5b,8,8,11a-penta methyl-1-(prop-1-en-2-yl)icosahydro-1H-cyclopenta[a]chrysen-9-yl acetate

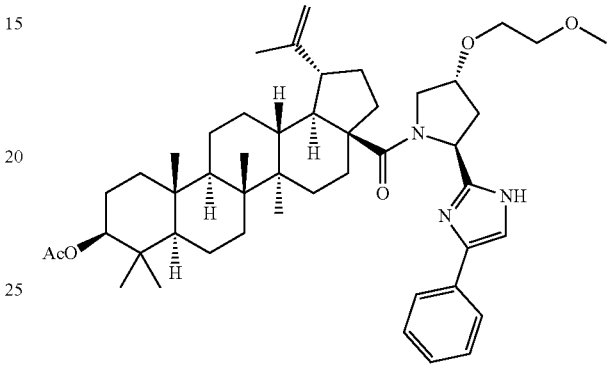

To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in *J. Med. Chem.* 2009, 52, 3248-3258, 3.0 g, 6.02 mmol) in DCM (50 ml), Oxalyl chloride (3.90 g, 30.12 mmol) was added at 0° C. and stirred at room temperature for about 3 hours. After completion of the reaction (monitored by TLC), the solvent was evaporated under nitrogen atmosphere, the residue was dissolved in DCM (10 ml) which was then added to a stirred solution of 2-((2S,4R)-4-(2-methoxyethoxy)pyrrolidin-2-

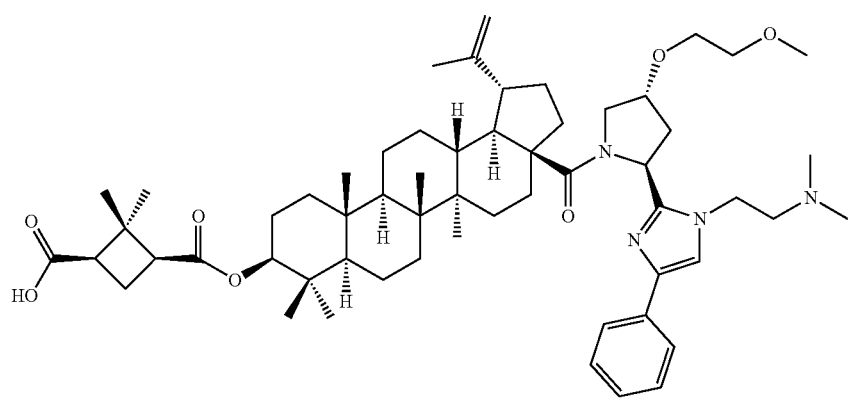

yl)-4-phenyl-1H-imidazole (Intermediate 14, 2.10 g, 7.31 mmol), triethyl amine (2.0 ml, 14.63 mmol) in DCM (40 ml) at 0° C. and allowed to stir at room temperature for about 16 hours. After completion of the reaction (monitored by TLC), the reaction mixture was diluted with dichloromethane (150 ml), washed with water, brine solution, dried over $Na_2SO_4$ and filtered. The solvent was evaporated and the residue was purified on silica gel column (100-200 mesh, eluted in 20% ethyl acetate/hexanes) to afford the title compound (2.90 g, yield: 62%) as an off white solid. $H^1$ NMR (DMSO-$D_6$, 300 MHz): δ 11.66 (bs, 1H), 7.70 (d, J=7.5 Hz, 2H), 7.44 (s, 1H), 7.29 (t, J=7.5 Hz, 2H), 7.13 (t, J=7.5, 1H), 5.13 (m, 1H), 4.54 (s, 1H), 4.46 (s, 1H), 4.33 (m, 2H), 3.80 (m, 2H), 3.56 (m, 2H), 3.42 (m, 2H), 3.24 (s, 3H), 2.95 (m, 1H), 2.15 (m, 2H), 1.99 (s, 3H), 0.70-2.0 (m, 42H); Mass (ESI): 768.63 (M+H)$^+$.

Step 2: Synthesis of a 1R,3aS,5aR,5bR,7aR,9S, 11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((2S,4R)-4-(2-methoxyethoxy)-2-(4-phenyl-1H-imidazol-2-yl)pyrrolidin-1-yl)methanone

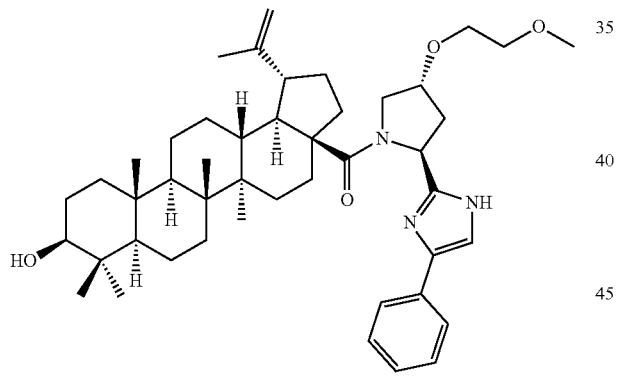

To a stirred solution of (1R,3aS,5aR,5bR,7aR,9S,11aR, 11bR,13aR,13bR)-3a-((2S,4R)-4-(2-methoxyethoxy)-2-(4-phenyl-1H-imidazol-2-yl)pyrrolidine-1-carbonyl)-5a,5b,8, 8,11a-pentamethyl-1-(prop-1-en-2-yl)icosahydro-1H-cyclopenta[a]chrysen-9-yl acetate (step 1, 1.50 g, 1.95 mmol) in MeOH:THF:$H_2O$ (1:1:1, 60 ml) was added lithium hydroxide monohydrate (492 mg, 11.73 mmol) and allowed to stir at room temperature for about 20 hours. After completion of the reaction (monitored by TLC), the solvents were evaporated, water was added and the product was extracted with ethyl acetate (2×100 ml). The combined organic layer was washed with brine solution, dried over $Na_2SO_4$, filtered and solvent was evaporated to afford the crude compound (1.21 g, yield: 86%) which was used in the next reaction without further purification. $H^1$ NMR (DMSO-$D_6$, 300 MHz): δ 11.64 (bs, 1H), 7.70 (d, J=8.0 Hz, 2H), 7.43 (s, 1H), 7.29 (t, J=8.0 Hz, 2H), 7.13 (t, J=8.0, 1H), 5.13 (m, 1H), 4.54 (s, 1H), 4.46 (s, 1H), 4.33 (m, 2H), 3.78 (m, 2H), 3.56 (m, 2H), 3.42 (m, 2H), 3.24 (s, 3H), 2.95 (m, 2H), 2.15 (m, 2H), 0.70-2.0 (m, 42H); Mass (ESI); 726.51 (M+H).

Step 3: Synthesis of ((2S,4R)-2-(1-(2-(dimethylamino)ethyl)-4-phenyl-1H-imidazol-2-yl)-4-(2-methoxyethoxy)pyrrolidin-1-yl)((1R,3aS,5aR,5bR, 7aR,9S,11aR,11bR,13aR,13bR)-9-hydroxy-5a,5b,8, 8,11a-pentamethyl-1-(prop-1-en-2-yl)icosahydro-3aH-cyclopenta[a]chrysen-3a-yl) methanone

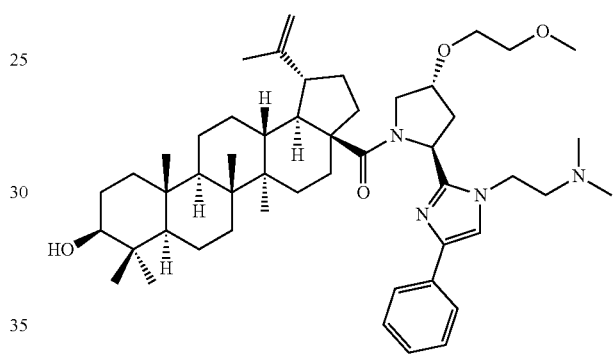

A stirred solution of ((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-3aH-cyclopenta[a]chrysen-3a-yl)((2S,4R)-4-(2-methoxyethoxy)-2-(4-phenyl-1H-imidazol-2-yl)pyrrolidin-1-yl)methanone (step 2, 350 mg, 0.48 mmol) in DMF (10 ml) was treated with sodium hydride (23 mg, 0.96 mmol) at 0° C. After stirring about 15 minutes at 0° C., a solution of 2-(dimethylamino)ethyl chloride hydrochloride (104 mg, 0.72 mmol), triethyl amine (0.10 ml, 0.72 mmol) in DMF (3 ml) was added and stirred at ambient temperature for about 24 hours. After completion of the reaction (monitored by TLC), the reaction was quenched with ice water, extracted with ethyl acetate (2×75 ml), washed with brine, dried over $Na_2SO_4$ and concentrated to afford the title compound (310 mg, yield: 81%). $H^1$ NMR (CDCl$_3$, 300 MHz): δ 7.70 (d, J=8.0 Hz, 2H), 7.29 (t, J=8.0 Hz, 2H), 7.16 (t, J=8.0, 1H), 7.08 (s, 1H), 5.29 (m, 1H), 4.62 (m, 1H), 4.58 (s, 1H), 4.47 (s, 1H), 4.30 (m, 1H), 4.22 (m, 1H), 4.16 (m, 2H), 3.83 (m, 1H), 3.65 (m, 2H), 3.55 (m, 2H), 3.39 (s, 3H), 3.17 (m, 1H), 2.6-2.80 (m, 3H), 2.34 (s, 6H), 2.15 (m, 2H), 0.70-2.0 (m, 42H).

Step 4: Synthesis of 1-benzyl 3-((1R,3aS,5aR,5bR, 7aR,9S,11aR,11bR,13aR,13bR)-3a-((2S,4R)-2-(1-(2-(dimethylamino)ethyl)-4-phenyl-1H-imidazol-2-yl)-4-(2-methoxyethoxy) pyrrolidine-1-carbonyl)-5a,5b, 8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate off white solid. $H^1$ NMR (CDCl$_3$, 300 MHz): δ 7.67 (d, J=7.5 Hz, 2H), 7.2-7.38 (m, 7H), 7.16 (m, 1H), 7.07 (s, 1H), 5.30 (m, 1H), 5.12 (m, 2H), 4.62 (m, 1H), 4.58 (s, 1H), 4.47 (s, 1H), 4.42 (m, 1H), 4.30 (m, 1H), 4.12 (m, 2H), 3.85 (m, 1H), 3.66 (m, 2H), 3.55 (m, 2H), 3.39 (s, 3H), 2.6-2.90 (m, 5H), 2.34 (s, 6H), 2.10-2.50 (m, 2H), 0.70-2.0 (m, 50H); Mass (ESI): 1041 [M+H]$^+$.

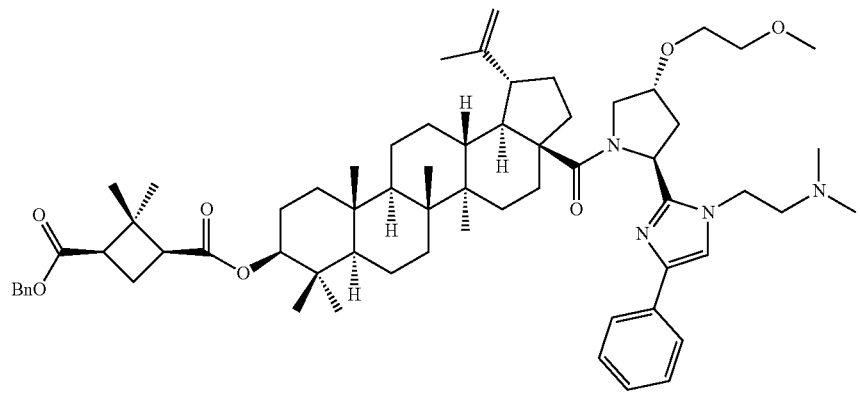

To a stirred solution of (1S,3R)-3-(benzyloxycarbonyl)-2,2-dimethylcyclobutane carboxylic acid (prepared as described in WO 2013/160810 A2, 200 mg, 0.76 mmol) in THF (10 ml) at 0° C. was added DIPEA (0.40 ml, 2.28 mmol) followed by 2,4,6-trichlorobenzoyl chloride (246 mg, 0.83 mmol). The mixture was stirred at ambient temperature for about 3 hours and concentrated under reduced pressure. The obtained mixed anhydride was dissolved in toluene (5 ml) and added to a stirred solution of ((2S,4R)-2-(1-(2-(dimethylamino)ethyl)-4-phenyl-1H-imidazol-2-yl)-4-(2-methoxyethoxy)pyrrolidin-1-yl)((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl) methanone (step 3, 302 mg, 0.38 mmol), DMAP (185 mg, 1.52 mmol) in toluene (20 ml) at room temperature and heated at 90° C. for about 18 hours. After completion of the reaction (monitored by TLC), the reaction mixture was diluted with ethyl acetate (200 ml) and then washed with brine solution. The organic layer was dried over Na$_2$SO$_4$, filtered and solvent was evaporated under reduced pressure. The residue was purified on silica gel column (100-200 mesh, eluted with 4-6% methanol/dichloromethane) to afford the title compound (150 mg, yield: 38%) as an Step 5: Synthesis of (1R,3S)-3-(((((1R,3aS,5aR,5bR, 7aR,9S,11aR,11bR,13aR,13bR)-3a-((2S,4R)-2-(1-(2-(dimethylamino)ethyl)-4-phenyl-1H-imidazol-2-yl)-4-(2-methoxyethoxy) pyrrolidine-1-carbonyl)-5a,5b, 8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid To a stirred solution of 1-benzyl 3-((1R,3aS,5aR,5bR, 7aR,9S,11aR,11bR,13aR,13bR)-3a-((2S,4R)-2-(1-(2-(dimethylamino)ethyl)-4-phenyl-1H-imidazol-2-yl)-4-(2-methoxy ethoxy)pyrrolidine-1-carbonyl)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate (step 4, 150 mg, 0.14 mmol) in MeOH:EtOAc (1:1, 16 ml) was added ammonium formate (45 mg, 0.72 mmol) followed by 10% Pd/C (30 mg) and stirred at ambient temperature for about 4 hours. After completion of the reaction (monitored by TLC), the catalyst was filtered through Celite bed and the filtrate was evaporated to dryness. The residue was purified by silica gel column chromatography using 8% methanol/dichloromethane as an eluent to afford the title compound (80 mg, yield: 59%). $H^1$ NMR (DMSO-D$_6$, 300 MHz): δ 12.13 (bs, 1H), 7.65 (d, J=8.0 Hz, 2H), 7.47 (s, 1H), 7.29 (t, J=8.0 Hz, 2H), 7.13 (t, J=8.0, 1H), 5.18 (m, 1H), 4.49 (s, 1H), 4.43 (s, 1H), 4.33 (m, 2H), 4.16 (m, 2H), 3.87 (m, 2H), 3.56 (m, 2H), 3.42 (m, 2H), 3.24 (s, 3H), 2.95 (m, 1H), 2.6-2.90 (m, 4H), 2.27 (s, 6H), 2.1-2.50 (m, 2H), 0.70-2.0 (m, 50H); Mass (ESI): 951.80 [M+H]$^+$; HPLC: 93.39%.

The below examples were prepared by the procedure similar to the one described in the synthesis of example-25 with appropriate variations in reactants and quantities of reagents. The characterization data of the examples are summarized herein below table.

| Example no | Structure | Characterization data |
|---|---|---|
| 26. | 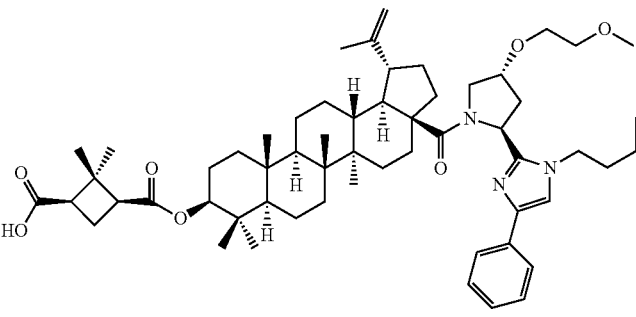 | H¹ NMR (DMSO-D$_6$, 300 MHz): δ 12.15 (bs, 1H), 7.66 (d, J = 8.0 Hz, 2H), 7.49 (s, 1H), 7.28 (t, J = 8.0 Hz, 2H), 7.12 (t, J = 8.0, 1H), 5.17 (m, 1H), 4.48 (s, 1H), 4.43 (s, 1H), 4.33 (m, 2H), 4.06 (m, 2H), 3.86 (m, 2H), 3.56 (m, 2H), 3.42 (m, 2H), 3.24 (s, 3H), 2.80-2.95 (m, 3H), 2.0-2.25 (m, 3H), 0.70-2.0 (m, 58H); Mass (ESI): 950.72 [M + H]$^+$; HPLC: 95.04%. |
| 27. | 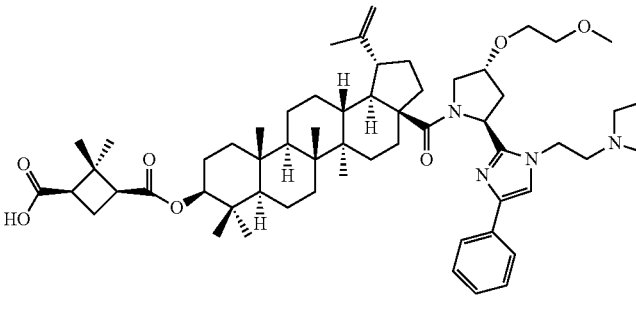 | H¹ NMR (DMSO-D$_6$, 300 MHz): δ 12.10 (broad peak, 1H), 7.65 (d, J = 8.1 Hz, 2H), 7.50 (s, 1H), 7.29 (t, J = 8.3 Hz, 2H), 7.13 (t, J = 8.1, 1H), 5.20 (m, 1H), 4.49 (s, 1H), 4.43 (s, 1H), 4.35 (m, 2H), 4.21 (m, 2H), 3.86 (m, 2H), 3.55 (m, 2H), 3.42 (m, 4H), 3.24 (s, 3H), 2.6-2.90 (m, 6H), 2.08-2.40 (m, 4H), 0.70-2.0 (m, 53H); Mass (ESI): 977.80 [M + H]$^+$; HPLC: 91.31%. |
| 28. | 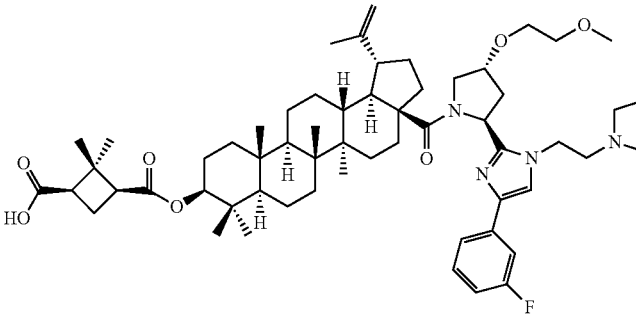 | H¹ NMR (DMSO-d$_6$, 300 MHz): δ 12.10 (broad peak, 1H), 7.60 (s, 1H), 7.28-7.50 (m, 3H), 6.93 (m, 1H), 5.02-5.20 (m, 1H), 4.49 (s, 1H), 4.43 (s, 1H), 4.35 (m, 2H), 4.21 (m, 2H), 3.86 (m, 2H), 3.55 (m, 2H), 3.42 (m, 4H), 3.24 (s, 3H), 2.60-2.96 (m, 6H), 2.08-2.40 (m, 4H), 0.65-1.72 (m, 53H); Mass (ESI): 995.83 [M + H]$^+$; HPLC: 98.18%. |

Example 29: Preparation of (1R,3S)-3-((((1R,3aS, 5aR,5bR,7aR,9S,11aR,11bR,13aR,13bR)-3a-((S)-2-(1-(2-(dimethylamino)ethyl)-1H-benzo[d]imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethylcyclobutane-1-carboxylic acid silica gel column (100-200 mesh, eluted in 30% ethyl acetate/hexane) to afford the title compound (1.20 g, yield: 26%). $H^1$ NMR (DMSO-$D_6$, 300 MHz): δ 12.05 (bs, 1H), 7.45 (m, 2H), 7.11 (m, 2H), 5.15 (m, 1H), 4.50 (s, 1H), 4.44 (s, 1H), 4.33 (m, 1H), 3.83 (m, 1H), 3.65 (m, 1H), 2.75 (m, 1H), 2.0-2.35 (m, 4H), 1.99 (s, 3H), 0.70-2.0 (m, 42H); Mass (ESI): 668.51 (M+H).

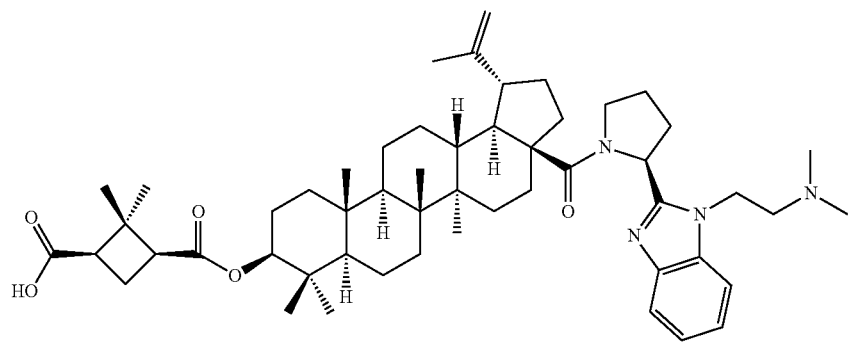

Step 1: Synthesis of (1R,3aS,5aR,5bR,7aR,9S,11aR, 11bR,13aR,13bR)-3a-((S)-2-(1H-benzo[d]imidazol-2-yl)pyrrolidine-1-carbonyl)-5a,5b,8,8,11a-pentamethyl-1-(prop-1-en-2-yl) icosahydro-1H-cyclopenta[a]chrysen-9-yl acetate Step 2: Synthesis of ((S)-2-(1H-benzo[d]imidazol-2-yl)pyrrolidin-1-yl)((1R,3aS,5aR,5bR,7aR,9S,11aR, 11bR,13aR,13bR)-9-hydroxy-5a,5b,8,8,11a-pentamethyl-1-(prop-1-en-2-yl) icosahydro-1H-cyclopenta[a chrysen-3a-yl)methanone

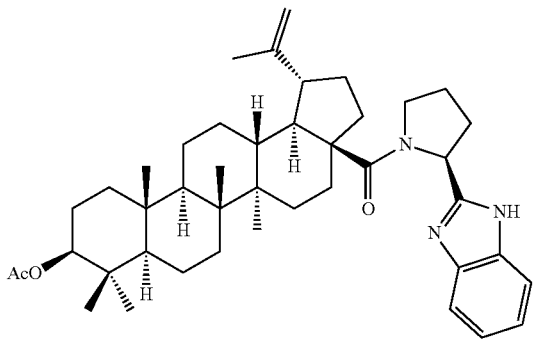

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in *J. Med. Chem.* 2009, 52, 3248-3258, 3.47 g, 6.9 mmol) in DCM (20 ml), oxalyl chloride (2.9 g, 34.8 mmol) was added at 0° C. and stirred at room temperature for about 3 hours. After completion of the reaction (monitored by TLC), the solvent was evaporated under nitrogen atmosphere and the residue was dissolved in DCM (10 ml) which was then added to a stirred solution of (S)-2-(pyrrolidin-2-yl)-1H-benzo[d]imidazole TFA salt (Intermediate 16, 2.0 g, 6.9 mmol) and triethyl amine (4.8 ml, 34.8 mmol) in DCM (20 ml) at 0° C. and allowed to stir at room temperature for about 16 hours. The reaction mixture was diluted with water, extracted dichloromethane (150 ml) and washed with brine and then dried over $Na_2SO_4$. The solvent was evaporated and purified on To a stirred solution of (1R,3aS,5aR,5bR,7aR,9S,11aR, 11bR,13aR,13bR)-3a-((S)-2-(1H-benzo[d]imidazol-2-yl) pyrrolidine-1-carbonyl)-5a,5b,8,8,11a-pentamethyl-1-(prop-1-en-2-yl) icosahydro-1H-cyclopenta[a]chrysen-9-yl acetate (step 1, 1.2 g, 1.79 mmol) in MeOH:THF:$H_2O$ (1:1:0.5, 30 ml) was added lithium hydroxide monohydrate (750 mg, 17.99 mmol) and allowed to stir at room temperature for about 18 hours. The solvents were evaporated, water was added and the product was extracted with ethyl acetate (2×100 ml) and the organic layer was washed with brine solution and dried over $Na_2SO_4$. The solvent was evaporated to afford the crude compound (650 mg, yield: 58%) which was used in the next reaction without further purification. $H^1$ NMR (DMSO-$D_6$, 300 MHz): δ 12.05 (bs, 1H), 7.45 (m, 2H), 7.10 (m, 2H), 5.14 (m, 1H), 4.49 (s, 1H), 4.44 (s, 1H), 4.26 (m, 1H), 3.83 (m, 1H), 3.65 (m, 1H), 2.95 (m, 1H), 2.70 (m, 1H), 2.0-2.35 (m, 4H), 0.70-2.0 (m, 42H); Mass (ESI): 626.48 (M+H).

Step 3: Synthesis of ((S)-2-(1-(2-(dimethylamino)ethyl)-1H-benzo[d]imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)methanone

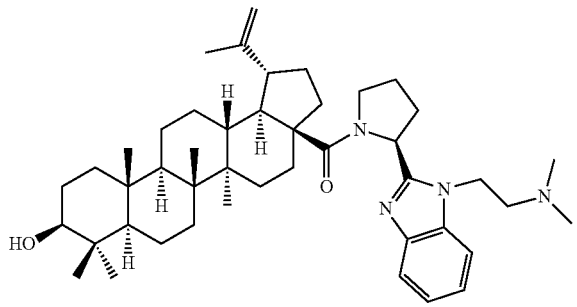

A solution of ((S)-2-(1H-benzo[d]imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(prop-1-en-2-yl) icosahydro-1H-cyclopenta[a]chrysen-3a-yl) methanone (step 2, 600 mg, 0.96 mmol) in DMF (10 ml) was treated with sodium hydride (60%, 115 mg, 4.7 mmol) at 0° C. After stirring about 15 minutes 0° C., a solution of 2-(dimethylamino)ethyl chloride hydrochloride (276 mg, 1.91 mmol) and triethyl amine (0.26 ml, 1.88 mmol) in DMF (2 ml) was added and stirred at ambient temperature for about 36 hours. After completion of the reaction (monitored by TLC), the reaction mixture was quenched with ice water, extracted with ethyl acetate (2×20 ml), and washed with brine, dried over $Na_2SO_4$ and concentrated to afford the title compound (490 mg, yield: 74%). $H^1$ NMR (DMSO-$D_6$, 300 MHz): δ 7.49 (t, 2H), 7.15 (m, 2H), 5.18 (m, 1H), 4.44 (s, 1H), 4.41 (s, 1H), 4.3-4.42 (m, 2H), 4.25 (m, 1H), 3.87 (m, 1H), 3.72 (m, 1H), 2.96 (m, 1H), 2.60-2.75 (m, 2H), 2.20-2.35 (m, 2H), 2.19 (s, 6H), 0.65-2.0 (m, 45H); Mass (ESI): 697.51 (M+H).

Step 4: Synthesis of 1-benzyl 3-((1R,3aS,5aR,5bR,7aR,9S,11aR,11bR,13aR,13bR)-3a-((S)-2-(1-(2-(dimethylamino)ethyl)-1H-benzo[d]imidazol-2-yl)pyrrolidine-1-carbonyl)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate To a stirred solution of (1S,3R)-3-(benzyloxycarbonyl)-2,2-dimethylcyclobutane carboxylic acid (prepared as described in WO 2013/160810 A2, 300 mg, 1.14 mmol) in THF (10 ml) at 0° C. was added DIPEA (0.59 ml, 3.42 mmol) followed by 2,4,6-trichlorobenzoyl chloride (0.18 ml, 1.14 mmol). The mixture was stirred at ambient temperature for about 3 hours and concentrated under reduced pressure. The obtained mixed anhydride was dissolved in toluene (10 ml) and added to a stirred solution of ((S)-2-(1-(2-(dimethylamino)ethyl)-1H-benzo[d] imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl) methanone (step 3, 490 mg, 0.70 mmol) and DMAP (171 mg, 1.40 mmol) in toluene (15 ml) at room temperature and heated at 90° C. for about 18 hours. After completion of the reaction (monitored by TLC), the reaction mixture was cooled to room temperature, diluted with ethyl acetate (200 ml) and washed with $NaHCO_3$ solution followed by brine solution. The organic layer was dried over $Na_2SO_4$, filtered and solvent was evaporated under reduced pressure. The residue was purified on silica gel column (100-200 mesh, elution 60% ethyl acetate/hexanes) to afford the title compound (297 mg, yield: 45%). $H^1$ NMR (DMSO-$D_6$, 300 MHz): δ 7.49 (t, 2H), 7.36 (m, 5H), 7.14 (m, 2H), 5.19 (m, 1H), 5.09 (ABq, 2H), 4.45 (s, 1H), 4.41 (s, 1H), 4.25-4.40 (m, 2H), 4.13 (m, 1H), 3.87 (m, 1H), 3.72 (m, 1H), 2.65-2.95 (m, 5H), 2.20-2.40 (m, 2H), 2.23 (s, 6H), 0.70-2.0 (m, 52H); Mass (ESI): 941.64 (M+H).

Step 5: Synthesis of (1R,3S)-3-(((((1R,3aS,5aR,5bR,7aR,9S,11aR,11bR,13aR,13bR)-3a-((S)-2-(1-(2-(dimethylamino)ethyl)-1H-benzo[d]imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid To a stirred solution of 1-benzyl 3-((1R,3aS,5aR,5bR,7aR,9S,11aR,11bR,13aR,13bR)-3a-((S)-2-(1-(2-(dimethylamino)ethyl)-1H-benzo[d]imidazol-2-yl)pyrrolidine-1-carbonyl)-5a,5b,8,8,11a-pentamethyl-1-(prop-1-en-2-yl)icosahydro-1H-cyclopenta[a]chrysen-9-yl) (1R,3S)-2,2-dimethylcyclobutane-1,3-dicarboxylate (step 4, 297 mg, 0.31 mmol) in MeOH:EtOAc (1:1, 10 ml) was added ammonium formate (100 mg, 1.56 mmol) followed by 10% Pd/C (50 mg) and stirred at ambient temperature for about 2 hours. After completion of the reaction (monitored by TLC), the catalyst was filtered through Celite bed and the filtrate was evaporated to dryness. The residue was purified

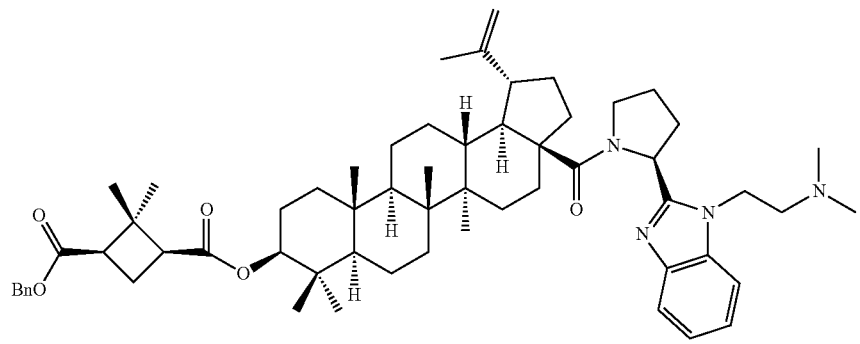

by silica gel column chromatography using 3% methanol/dichloromethane as an eluent to afford the title compound (90 mg, yield: 35%). H¹ NMR (DMSO-D₆, 300 MHz): δ 12.10 (br peak, 1H), 7.49 (t, 2H), 7.07-7.20 (m, 2H), 5.18 (m, 1H), 4.45 (s, 1H), 4.41 (s, 1H), 4.25-4.40 (m, 3H), 3.87 (m, 1H), 3.72 (m, 1H), 2.60-2.83 (m, 5H), 2.20-2.40 (m, 2H), 2.23 (s, 6H), 0.70-2.0 (m, 52H); Mass (ESI): 851.56 [M+H]⁺; HPLC: 95.20%.

The below examples were prepared by the procedure similar to the one described in the synthesis of example-29 with appropriate variations in reactants and quantities of reagents. The characterization data of the examples are summarized herein below table.

| Example no | Structure | Characterization data |
|---|---|---|
| 30. | 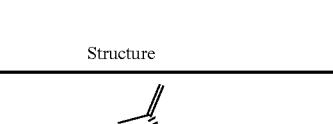 | H¹ NMR (DMSO-D₆, 300 MHz): δ 12.13 (bs, 1H), 7.49 (t, 2H), 7.08-7.20 (m, 2H), 5.21 (m, 1H), 4.30-4.50 (m, 5H), 3.87 (m, 1H), 3.70 (m, 1H), 2.72-2.95 (m, 5H), 2.10-2.50 (m, 6H), 0.70-2.0 (m, 56H); Mass (ESI): 877.64 [M + H]⁺; HPLC: 94.54%. |

Pharmacological Activity

The compounds described herein can be tested for their antiviral activity following procedures known to a person of ordinary skill in the art. For example, the following protocols can be employed for testing the compounds. These protocols are illustrative and do not limit to the scope of the invention.

Example 31: Evaluation of Compounds Antiviral Activity

MT-2 cells were infected with required number of TCID50's of HIV-1 strains, for e.g., 92HT599. The infected cells were plated at the concentration of 30,000 cells per well in a 96 well plate. Test compound was added to the 96 well plate with the final concentration of DMSO (vehicle—not more than 1%). The plates are then incubated in a CO₂ incubator for ~96 hours (~4 days) for viral infection. At the end of incubation period an aliquot from each well was taken for p24 estimation. The quantitation of p24 is an estimated index for antiviral activity of the compound. Percent inhibition was calculated with reference to control values (vehicle controls).

p-24 estimation was carried out using Advance biosciences kit as per the procedure detailed by supplier.

Results:

TABLE 1

| Compound No. | Antiviral activity (% inhibition) | | |
|---|---|---|---|
| | 1 μM | 0.1 μM | 0.01 μM |
| 12 | 99 | 44 | 24 |
| 26 | 99 | 15 | 0 |
| 23 | 66 | 21 | 24 |

TABLE 1-continued

| Compound No. | Antiviral activity (% inhibition) | | |
|---|---|---|---|
| | 1 μM | 0.1 μM | 0.01 μM |
| 27 | 100 | 100 | 0 |
| 28 | 100 | 98 | 13 |
| 29 | 100 | 100 | 0 |
| 30 | 100 | 100 | 71 |

TABLE 1A

| Compound No. | Antiviral activity IC50 (nM) |
|---|---|
| 1 | 6.735 |
| 3 | 112.6 |
| 5 | 73.17 |
| 6 | 2.547 |
| 7 | 75.33 |
| 8 | 12.53 |
| 9 | 10.59 |
| 10 | 7.748 |
| 11 | 3.585 |
| 15 | 7.419 |
| 16 | 8.48 |
| 17 | 0.3 |
| 18 | 80.42 |
| 19 | 7.76 |
| 22 | 14.9 |
| 24 | 0.972 |
| 27 | 34.03 |
| 28 | 39.58 |
| 29 | 9.758 |
| 30 | 10.22 |

Example 32: Evaluation of Compounds Cyto-Toxicity

On day 1 calculate the number of cells required for the assay and seed 3×10⁴ cells in 200 μl per well. Weigh the compound and dissolve it in DMSO to get 10 mM stock which is further diluted to 3 mM and 1 mM. The drugs from these stocks were added to plate to get final concentration of 100 μM, 30 μM and 10 μM. Add DMSO to controls in a way to obtain final concentration of solvent that is not greater than 1%. Incubate for 4 days in 5% CO₂ incubator at 37° C. On day 4, 100 μl of medium was removed from each well without disturbing the cells. Add 10 μl of MTT reagent and incubate for 4 hours at 5% $CO_2$ incubator at 37° C. for formation of crystals. Add 200 μl of 0.1N acidic isopropanol to dissolve the crystals and read the plate at 590 nm.

Results:

TABLE 2

| Compound No. | Cytotoxicity % viability | | |
|---|---|---|---|
| | 100 μM | 30 μM | 10 μM |
| 12 | 5 | 31 | 42 |
| 26 | 9 | 54 | 77 |
| 23 | 66 | 77 | 88 |

TABLE 2A

| Compound No. | Cytotoxicity % viability | | |
|---|---|---|---|
| | 1 uM | 0.1 uM | 0.01 uM |
| 27 | 8 | 24 | 60 |
| 28 | 6 | 19 | 65 |
| 29 | 5 | 1 | 31 |
| 30 | 5 | 3 | 33 |

Example 33: Evaluation of Compounds Single Dose Oral Pharmacokinetic Study

The test item was administered through oral route to animals (rat/mice) at 30 mg/kg dose in a suitable vehicle at 10 ml/kg dose volume. Blood samples (~50 uL at each time point) were collected from retro-orbital plexus using K3 EDTA as anticoagulant in eppendorf tubes at defined time intervals under light ether anesthesia. The samples were centrifuged at 3500×g to separate plasma and stored at −80° C. until analysis.

Sample analysis: Test samples were analyzed using LC-MS-MS after developing fit-for-purpose method for each of test compound.

Results:

TABLE 3

| Compound No. | Mice oral PK @30 mg/kg | |
|---|---|---|
| | Cmax μg/mL | AUC 0-t μg · hr/mL |
| 1 | 8.545 | 249.781 |
| 2 | 11.396 | 334.593 |
| 3 | 14.671 | 407.21 |
| 4 | 9.217 | 291.037 |
| 5 | 10.4065 | 292.3775 |
| 6 | 9.455 | 211.787 |
| 8 | 9.078 | 243.381 |
| 9 | 6.898 | 259.627 |
| 10 | 4.638 | 144.713 |
| 11 | 18.11 | 755.212 |
| 15 | 15.337 | 376.271 |
| 16 | 9.027 | 293.588 |
| 17 | 13.007 | 270.838 |
| 18 | 0.648 | 3.007 |
| 19 | 4.262 | 97.399 |
| 22 | 5.833 | 215.293 |
| 24 | 2.554 | 89.393 |
| 25 | 17.58 | 617.413 |
| 27 | 10.9 | 355.2 |
| 28 | 7.3 | 293.1 |

TABLE 3-continued

| Compound No. | Mice oral PK @30 mg/kg | |
|---|---|---|
| | Cmax μg/mL | AUC 0-t μg · hr/mL |
| 29 | 14.9 | 490.8 |
| 30 | 14.8 | 546.3 |
| — | — | — |
| — | — | — |
| — | — | — |
| — | — | — |

REFERENCES

1. Antiviral methods and protocols (Eds: D Kinchington and R F Schinazi) Humana Press Inc., 2000
2. HIV protocols (Eds: N L Michael and J H Kim) Humana Press Inc, 1999
3. DAIDS Virology manual for HIV laboratories, Publication NIH-97-3838, 1997
4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

We claim:
1. A Compound of the formula (1):

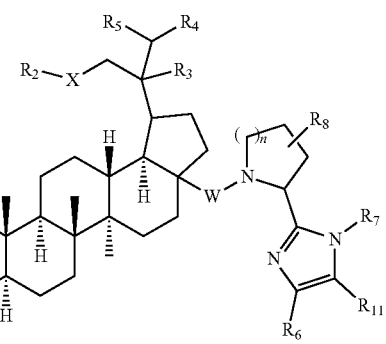

Formula (1)

wherein,
$R_1$ is substituted or unsubstituted alkyl,

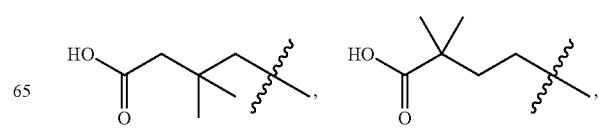

-continued

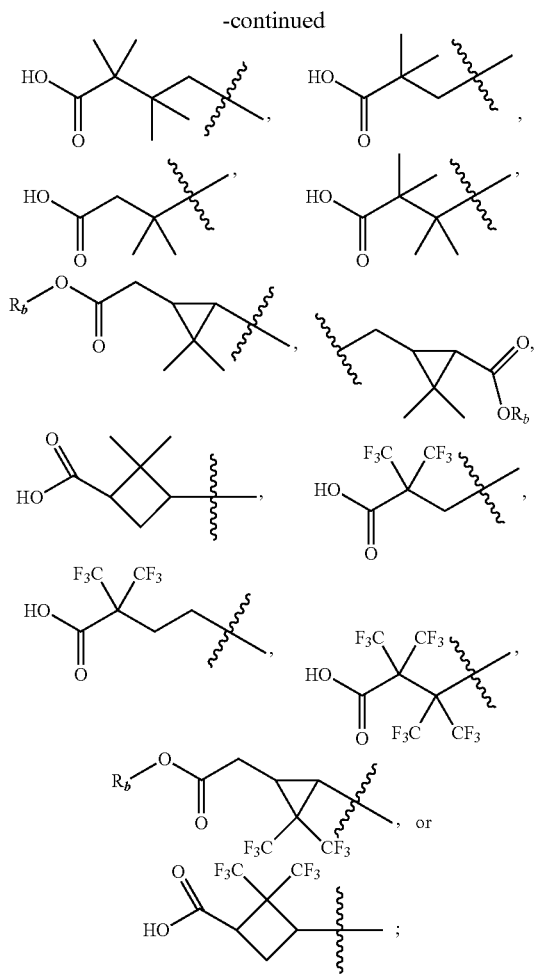

wherein $R_b$ is H, substituted or unsubstituted alkyl, or substituted or unsubstituted cycloalkyl;

$R_2$ is H, substituted or unsubstituted alkyl, substituted or unsubstituted aminoacids, substituted or unsubstituted alkoxy, or substituted or unsubstituted cycloalkyl;

X is absent, O, S, $CH_2$ or $NR_a$, wherein $R_a$ is H, substituted or unsubstituted alkyl, substituted or unsubstituted cycloalkyl, or $R_a$ is with their adjacent N and Carbon together form N-contained heterocycle;

$R_3$ and $R_4$ are independently selected from H, OH, substituted or unsubstituted alkyl, substituted or unsubstituted alkoxy, substituted or unsubstituted alkoxylalkoxy, or substituted or unsubstituted aminoacids, or $R_3$ and $R_4$ are together with their adjacent carbons to form a bond or $R_3$ and $R_4$ are together with their adjacent carbons to form cyclopropyl or $R_3$ and $R_4$ are together with their adjacent carbons to form epoxide;

W is C(O), C(S), or $CR_9R_{10}$;

$R_6$ is substituted or unsubstituted alkyl, substituted or unsubstituted cycloalkyl, substituted or unsubstituted aryl, substituted or unsubstituted heterocyclyl, or substituted or unsubstituted heteroaryl;

$R_7$ is independently selected from substituted or unsubstituted alkyl and substituted or unsubstituted alkoxy;

$R_8$ is independently selected from H, hydroxy, substituted or unsubstituted alkyl, or substituted or unsubstituted alkoxy;

$R_5$, $R_9$ and $R_{10}$ are independently selected from H, $CO_2R_d$ (wherein $R_d$ is H, substituted or unsubstituted alkyl, or substituted or unsubstituted cycloalkyl), or substituted or unsubstituted alkyl;

$R_{11}$ is H or substituted or unsubstituted alkyl;

alternatively $R_6$ and $R_{11}$ may be taken together with carbon atoms to which they are attached to form a substituted or unsubstituted aryl;

n is an integer from 1 to 3; including pharmaceutically acceptable salts, pharmaceutically acceptable solvates, pharmaceutically acceptable hydrates, tautomers, stereoisomers, or combination thereof.

2. The compound of claim 1, wherein W is —C(O)—.

3. A compound of the formula (1A):

Formula (1A)

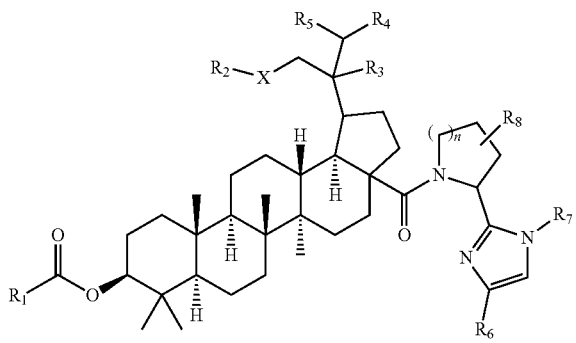

wherein $R_1$, $R_2$, $R_3$, $R_4$, $R_5$, $R_6$, $R_7$, $R_8$, X and n are as defined in claim 1; including pharmaceutically acceptable salts, pharmaceutically acceptable solvates, pharmaceutically acceptable hydrates, tautomers, stereoisomers, or combination thereof.

4. The compound of claim 1, wherein when $R_3$, $R_4$, or both are substituted amino acid, the amino acid is substituted by substituted or unsubstituted alkyl, or phosphoric acid.

5. A compound selected from the group consisting of:
(1R,3S)-2,2-dimethyl-3-(((((1R,3aS,5aR,5bR,7aR,9S, 11aR,11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid,
(1R,3S)-3-(((((1R,3aS,5aR,5bR,7aR,9S,11aR,11bR,13aR, 13bR)-3a-((S)-2-(1-(2-(2-methoxyethoxy)ethyl)-4-phenyl-1H-imidazol-2-yl)pyrrolidine-1-carbonyl)-5a, 5b,8,8,11a-penta methyl-1-(prop-1-en-2-yl) icosahydro-1H-cyclopenta[a]chrysen-9-yl)oxy) carbonyl)-2,2-dimethyl cyclobutane-1-carboxylic acid,
(1R,3S)-2,2-dimethyl-3-(((((1R,3aS,5aR,5bR,7aR,9S, 11aR,11bR,13aR,13bR)-5a,5b,8,8,11a-pentamethyl-3a-((S)-2-(1-(2-morpholinoethyl)-4-phenyl-1H-imidazol-2-yl)pyrrolidine-1-carbonyl)-1-(prop-1-en-2-yl) icosahydro-1H-cyclopenta[a]chrysen-9-yl)oxy) carbonyl)cyclo butane-1-carboxylic acid,
(1R,3S)-3-(((((1R,3aS,5aR,5bR,7aR,9S,11aR,11bR,13aR, 13bR)-3a-((S)-2-(1-(2-methoxyethyl)-4-phenyl-1H-imidazol-2-yl)pyrrolidine-1-carbonyl)-5a,5b,8,8,11a-penta methyl-1-(prop-1-en-2-yl)icosahydro-1H-cyclopenta[a]chrysen-9-yl)oxy)carbonyl)-2,2-dimethylcyclobutane-1-carboxylic acid,
(1R,3S)-3-(((((1R,3aS,5aR,5bR,7aR,9S,11aR,11bR,13aR, 13bR)-3a-((S)-2-(1-(2-(dimethylamino)ethyl)-4-phenyl-1H-imidazol-2-yl)pyrrolidine-1-carbonyl)-5a,5b,8, 8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, (1R,3S)-3-(((((1R,3aS,5aR,5bR,7aR,9S,11aR,11bR,13aR, 13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid, (1R,3S)-3-(((((1R,3aS,5aR,5bR,7aR,9S,11aR,11bR,13aR, 13bR)-3a-((S)-2-(1-(2-(dimethylamino)ethyl)-4-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid, (1R,3S)-3-(((((1R,3aS,5aR,5bR,7aR,9S,11aR,11bR,13aR, 13bR)-3a-((S)-2-(1-(2-(dimethylamino)ethyl)-4-(pyridin-4-yl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid, (1R,3S)-2,2-dimethyl-3-(((((1R,3aS,5aR,5bR,7aR,9S, 11aR,11bR,13aR,13bR)-5a,5b,8,8,11a-pentamethyl-1-(prop-1-en-2-yl)-3a-((S)-2-(4-(pyridin-4-yl)-1-(2-(pyrrolidin-1-yl) ethyl)-1H-imidazol-2-yl)pyrrolidine-1-carbonyl)icosahydro-1H-cyclopenta[a]chrysen-9-yl)oxy)carbonyl) cyclobutane-1-carboxylic acid, (1R,3S)-2,2-dimethyl-3-(((((1R,3aS,5aR,5bR,7aR,9S, 11aR,11bR,13aR,13bR)-5a,5b,8,8,11a-pentamethyl-3a-((S)-2-(4-phenyl-1-(2-(pyrrolidin-1-yl)ethyl)-1H-imidazol-2-yl) pyrrolidine-1-carbonyl)-1-(prop-1-en-2-yl)icosahydro-1H-cyclopenta[a]chrysen-9-yl)oxy) carbonyl)cyclo butane-1-carboxylic acid, (1R,3S)-3-(((((1R,3aS,5aR,5bR,7aR,9S,11aR,11bR,13aR, 13bR)-3a-((S)-2-(4-(tert-butyl)-1-(2-(dimethylamino) ethyl)-1H-imidazol-2-yl)pyrrolidine-1-carbonyl)-5a, 5b,8,8,11a-penta methyl-1-(prop-1-en-2-yl)icosahydro-1H-cyclopenta[a]chrysen-9-yl)oxy) carbonyl)-2,2-dimethyl cyclobutane-1-carboxylic acid, (1R,3S)-3-(((((1R,3aS,5aR,5bR,7aR,9S,11aR,11bR,13aR, 13bR)-3a-((S)-2-(1-(2-(dimethylamino)ethyl)-4-(3-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid, (1R,3S)-3-(((((1R,3aS,5aR,5bR,7aR,9S,11aR,11bR,13aR, 13bR)-3a-((S)-2-(1-(2-(dimethylamino)ethyl)-4-isopropyl-1H-imidazol-2-yl)pyrrolidine-1-carbonyl)-5a, 5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, (1R,3S)-3-(((((1R,3aS,5aR,5bR,7aR,9S,11aR,11bR,13aR, 13bR)-3a-((S)-2-(1-(2-(dimethylamino)ethyl)-4,5-dimethyl-1H-imidazol-2-yl)pyrrolidine-1-carbonyl)-5a, 5b,8,8,11a-pentamethyl-1-(prop-1-en-2-yl)icosahydro-1H-cyclopenta[a]chrysen-9-yl)oxy)carbonyl)-2,2-dimethyl cyclobutane-1-carboxylic acid, 2,2-dimethyl-4-oxo-4-(((1R,3aS,5aR,5bR,7aR,9S,11aR, 11bR,13aR,13bR)-5a,5b,8,8,11a-pentamethyl-3a-((S)-2-(1-methyl-4-phenyl-1H-imidazol-2-yl)pyrrolidine-1-carbonyl)-1-(prop-1-en-2-yl)icosahydro-1H-cyclopenta[a]chrysen-9-yl)oxy)butanoic acid, 4-(((1R,3aS,5aR,5bR,7aR,9S,11aR,11bR,13aR,13bR)-3a-((S)-2-(1-(2-(dimethyl amino)ethyl)-4-phenyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxo butanoic acid, 4-((((1R,3aS,5aR,5bR,7aR,9S,11aR,11bR,13aR,13bR)-3a-((S)-2-(1-(2-methoxyethyl)-4-phenyl-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid, 4-(((1R,3aS,5aR,5bR,7aR,9S,11aR,11bR,13aR,13bR)-3a-((S)-2-(1-(2-(dimethyl amino)ethyl)-4-(pyridin-3-yl)-1H-imidazol-2-yl)pyrrolidine-1-carbonyl)-5a,5b,8, 8,11a-pentamethyl-1-(prop-1-en-2-yl)icosahydro-1H-cyclopenta[a]chrysen-9-yl)oxy)-2,2-dimethyl-4-oxobutanoic acid, (1R,3S)-3-(((((1R,3aS,5aR,5bR,7aR,9S,11aR,11bR,13aR, 13bR)-3a-((S)-2-(1-(2-(dimethylamino)ethyl)-4-(pyridin-3-yl)-1H-imidazol-2-yl)pyrrolidine-1-carbonyl)-5a,5b,8,8,11a-pentamethyl-1-(1-methylcyclopropyl) icosahydro-1H-cyclopenta[a]chrysen-9-yl)oxy) carbonyl)-2,2-dimethylcyclobutane-1-carboxylic acid, (1R,3S)-3-(((((1R,3aS,5aR,5bR,7aR,9S,11aR,11bR,13aR, 13bR)-3a-((S)-2-(4-(tert-butyl)-1-(2-(dimethylamino) ethyl)-1H-imidazol-2-yl)pyrrolidine-1-carbonyl)-5a, 5b,8,8,11a-pentamethyl-1-(1-methylcyclopropyl) icosahydro-1H-cyclopenta[a]chrysen-9-yl)oxy) carbonyl)-2,2-dimethylcyclobutane-1-carboxylic acid, (1R,3S)-3-(((((1R,3aS,5aR,5bR,7aR,9S,11aR,11bR,13aR, 13bR)-3a-((S)-2-(1-(2-(dimethylamino)ethyl)-4,5-dimethyl-1H-imidazol-2-yl)pyrrolidine-1-carbonyl)-5a, 5b,8,8,11a-pentamethyl-1-(1-methylcyclopropyl) icosahydro-1H-cyclopenta[a]chrysen-9-yl)oxy) carbonyl)-2,2-dimethyl cyclobutane-1-carboxylic acid, (1R,3S)-3-(((((1R,3aS,5aR,5bR,7aR,9S,11aR,11bR,13aR, 13bR)-3a-((S)-2-(1-(2-(diethoxyphosphoryl)ethyl)-4-phenyl-1H-imidazol-2-yl)pyrrolidine-1-carbonyl)-5a, 5b,8,8,11a-pentamethyl-1-(prop-1-en-2-yl)icosahydro-1H-cyclopenta[a]chrysen-9-yl)oxy) carbonyl)-2,2-dimethyl cyclobutane-1-carboxylic acid, (1R,3S)-2,2-dimethyl-3-(((((1R,3aS,5aR,5bR,7aR,9S, 11aR,11bR,13aR,13bR)-5a,5b,8,8,11a-pentamethyl-3a-((S)-2-(4-phenyl-1-(2-phosphonoethyl)-1H-imidazol-2-yl)pyrrolidine-1-carbonyl)-1-(prop-1-en-2-yl)icosahydro-1H-cyclopenta[a]chrysen-9-yl)oxy) carbonyl)cyclo butane-1-carboxylic acid, (1R,3S)-3-((((1R,3aS,5aR,5bR,7aR,9S,11aR,11bR,13aR, 13bR)-3a-((S)-2-(1-(2-(diethoxyphosphoryl)ethyl)-4-(4-fluorophenyl)-1H-imidazol-2-yl)pyrrolidine-1-carbonyl)-5a,5b,8,8,11a-pentamethyl-1-(prop-1-en-2-yl) icosahydro-1H-cyclopenta[a]chrysen-9-yl) oxy) carbonyl)-2,2-dimethylcyclobutane-1-carboxylic acid, (1R,3S)-3-(((((1R,3aS,5aR,5bR,7aR,9S,11aR,11bR,13aR, 13bR)-3a-((2S,4R)-2-(1-(2-(dimethylamino)ethyl)-4-phenyl-1H-imidazol-2-yl)-4-(2-methoxyethoxy)pyrrolidine-1-carbonyl)-5a,5b,8,8,11a-pentamethyl-1-(prop-1-en-2-yl)icosahydro-1H-cyclopenta[a]chrysen-9-yl) oxy)carbonyl)-2,2-dimethylcyclobutane-1-carboxylic acid, (1R,3S)-3-(((((1R,3aS,5aR,5bR,7aR,9S,11aR,11bR,13aR, 13bR)-3a-((2S,4R)-2-(1-isopentyl-4-phenyl-1H-imidazol-2-yl)-4-(2-methoxyethoxy)pyrrolidine-1-carbonyl)-5a,5b,8,8,11a-pentamethyl-1-(prop-1-en-2-yl) icosahydro-1H-cyclopenta[a]chrysen-9-yl)oxy) carbonyl)-2,2-dimethylcyclobutane-1-carboxylic acid, (1R,3S)-3-(((((1R,3aS,5aR,5bR,7aR,9S,11aR,11bR,13aR, 13bR)-3a-((2S,4R)-4-(2-methoxyethoxy)-2-(4-phenyl-1-(2-(pyrrolidin-1-yl)ethyl)-1H-imidazol-2-yl)pyrrolidine-1-carbonyl)-5a,5b,8,8,11a-pentamethyl-1-(prop- 1-en-2-yl)icosahydro-1H-cyclopenta[a]chrysen-9-yl) oxy)carbonyl)-2,2-dimethylcyclobutane-1-carboxylic acid, (1R,3S)-3-((((1R,3aS,5aR,5bR,7aR,9S,11aR,11bR,13aR, 13bR)-3a-((2S,4R)-2-(4-(3-fluorophenyl)-1-(2-(pyrrolidin-1-yl)ethyl)-1H-imidazol-2-yl)-4-(2-methoxyethoxy) pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, (1R,3S)-3-((((1R,3aS,5aR,5bR,7aR,9S,11aR,11bR,13aR, 13bR)-3a-((S)-2-(1-(2-(dimethylamino)ethyl)-1H-benzo[d]imidazol-2-yl)pyrrolidine-1-carbonyl)-5a,5b, 8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, and (1R,3S)-2,2-dimethyl-3-((((1R,3aS,5aR,5bR,7aR,9S, 11aR,11bR,13aR,13bR)-5a,5b, 8,8,11a-pentamethyl-1-(prop-1-en-2-yl)-3a-((S)-2-(1-(2-(pyrrolidin-1-yl) ethyl)-1H-benzo[d]imidazol-2-yl)pyrrolidine-1-carbonyl)icosahydro-1H-cyclopenta[a]chrysen-9-yl) oxy) carbonyl)cyclobutane-1-carboxylic acid, or pharmaceutically acceptable salts, pharmaceutically acceptable solvates, pharmaceutically acceptable hydrates, tautomers, stereoisomers, or combination thereof.

6. A pharmaceutical composition comprising a compound according to claim 1 and at least one pharmaceutically acceptable excipient.

7. The pharmaceutical composition according to claim 6, wherein the pharmaceutically acceptable excipient is a carrier or diluent.

8. A method of treating HIV in a subject in need thereof comprising administering to the subject a therapeutically effective amount of a compound according to claim 1.

9. A method for treating an HIV mediated disease in a subject in need thereof comprising administering to the subject a therapeutically effective amount of a pharmaceutical composition according to claim 6.

10. A pharmaceutical composition comprising a compound according to claim 5 and at least one pharmaceutically acceptable excipient.

11. A method of treating HIV in a subject in need thereof comprising administering to the subject a therapeutically effective amount of a compound according to claim 5.

12. The compound of claim 1, wherein X is $NR_a$ wherein $R_a$ is with their adjacent N and Carbon together form pyrrolidine, piperdine, piperzine, or morpholine.

13. The compound of claim 1, wherein $R_6$ is substituted or unsubstituted isopropyl, substituted or unsubstituted butyl, substituted or unsubstituted phenyl, substituted or unsubstituted pyridine, substituted or unsubstituted pyrazine, substituted or unsubstituted pyrimidine, or substituted or unsubstituted chromene.

* * * * *